US011261460B2

(12) United States Patent
Byrne et al.

(10) Patent No.: US 11,261,460 B2
(45) Date of Patent: *Mar. 1, 2022

(54) COMPOSITIONS AND METHODS FOR TREATING DISEASES

(71) Applicant: University of Florida Research Foundation, Incorporated, Gainesville, FL (US)

(72) Inventors: Barry John Byrne, Gainesville, FL (US); Darin J. Falk, Gainesville, FL (US); Christina Pacak, Gainesville, FL (US); Lara Robert DeRuisseau, Syracuse, NY (US); Cathryn Mah, Irvine, CA (US); David D. Fuller, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/994,477

(22) Filed: Jan. 13, 2016

(65) Prior Publication Data

US 2016/0369297 A1     Dec. 22, 2016
US 2018/0051299 A9     Feb. 22, 2018

Related U.S. Application Data

(63) Continuation of application No. 13/527,350, filed on Jun. 19, 2012, now abandoned, which is a continuation-in-part of application No. 12/305,869, filed as application No. PCT/US2008/054911 on Feb. 25, 2008, now abandoned.

(60) Provisional application No. 60/891,369, filed on Feb. 23, 2007.

(51) Int. Cl.
| | |
|---|---|
| *A61K 35/76* | (2015.01) |
| *A61K 48/00* | (2006.01) |
| *C12N 15/864* | (2006.01) |
| *C12N 9/26* | (2006.01) |
| *A61K 38/47* | (2006.01) |
| *C12N 15/86* | (2006.01) |
| *C12N 7/00* | (2006.01) |
| *A61K 45/06* | (2006.01) |
| *A61K 9/00* | (2006.01) |

(52) U.S. Cl.
CPC ............ *C12N 15/86* (2013.01); *A61K 9/0019* (2013.01); *A61K 45/06* (2013.01); *A61K 48/0058* (2013.01); *C12N 7/00* (2013.01); *C12Y 302/0102* (2013.01); *A61K 48/0075* (2013.01); *C12N 2710/16644* (2013.01); *C12N 2750/14143* (2013.01); *C12N 2750/14145* (2013.01); *C12N 2750/14151* (2013.01); *C12N 2810/6027* (2013.01); *C12N 2830/008* (2013.01)

(58) Field of Classification Search
None
See application file for complete search history.

(56) References Cited

U.S. PATENT DOCUMENTS

| | | |
|---|---|---|
| 5,962,313 A | 10/1999 | Podsakoff et al. |
| 2003/0100526 A1 | 5/2003 | Souza et al. |
| 2003/0223966 A1 | 12/2003 | Fraites et al. |
| 2004/0038402 A1 | 2/2004 | Antoniou et al. |
| 2004/0248262 A1* | 12/2004 | Koeberl ............... C12N 9/2408 435/69.7 |
| 2005/0014262 A1 | 1/2005 | Gao et al. |
| 2005/0220766 A1* | 10/2005 | Amalfitano ............ A61K 38/47 424/93.2 |
| 2005/0234000 A1 | 10/2005 | Mitchell et al. |
| 2006/0078542 A1* | 4/2006 | Mah ...................... A61K 9/0014 424/93.2 |
| 2007/0059288 A1* | 3/2007 | Dinsmore .......... A01K 67/0271 424/93.2 |
| 2007/0155688 A1 | 7/2007 | Fisher |
| 2008/0269149 A1* | 10/2008 | Bowles ................. C12N 15/86 514/44 R |
| 2009/0099611 A1* | 4/2009 | Sigg ..................... A61K 48/005 514/1.1 |
| 2010/0221225 A1 | 9/2010 | Byrne et al. |
| 2010/0240739 A1 | 9/2010 | Barkats |
| 2010/0305068 A1 | 12/2010 | Bulawa |
| 2012/0082653 A1 | 4/2012 | Koeberl |
| 2012/0141420 A1 | 6/2012 | Schneider et al. |
| 2012/0322861 A1 | 12/2012 | Byrne et al. |

(Continued)

FOREIGN PATENT DOCUMENTS

| | | |
|---|---|---|
| CN | 1922313 A | 2/2007 |
| CN | 101636200 A | 1/2010 |

(Continued)

OTHER PUBLICATIONS

Molnar and Nemeth, Gene therapy in neurology: review of ongoing clinical trials, Clin. Invest. (2012) 2(6), 639-652.*
Mingozzi and High, Therapeutic in vivo gene transfer for genetic disease using AAV: progress and challenges, Nature Reviews, 2011, pp. 341-356.*
Pacak et al, Tissue specific promoters improve specificity of AAV9 mediated transgene expression following intra-vascular gene delivery in neonatal mice, Genetic Vaccines and Therapy 2008, pp. 1-5.*

(Continued)

*Primary Examiner* — Maria Marvich
(74) *Attorney, Agent, or Firm* — Wolf, Greenfield & Sacks, P.C.

(57) ABSTRACT

The present invention provides compositions and methods of use pertaining to rAAV-mediated delivery of therapeutically effective molecules for treatment of diseases such as Pompe disease. These compositions in combination with various routes and methods of administration result in targeted expression of therapeutic molecules in specific organs, tissues and cells.

8 Claims, 51 Drawing Sheets

(56) References Cited

U.S. PATENT DOCUMENTS

| | | |
|---|---|---|
| 2013/0166313 A1 | 6/2013 | Kitfield et al. |
| 2015/0164906 A1 | 6/2015 | Zack |
| 2015/0196671 A1 | 7/2015 | Byrne et al. |
| 2016/0369297 A1 | 12/2016 | Byrne et al. |
| 2017/0028002 A1 | 2/2017 | Byrne et al. |

FOREIGN PATENT DOCUMENTS

| | | |
|---|---|---|
| EP | 1390490 B1 | 4/2009 |
| JP | 2010-540598 A | 12/2010 |
| RU | 2 452 368 C2 | 6/2012 |
| WO | WO 03/092594 A2 | 11/2003 |
| WO | WO 03/092598 A2 | 11/2003 |
| WO | WO 2007/089632 A2 | 8/2007 |
| WO | WO 2008/103993 A2 | 8/2008 |
| WO | WO 2009/043936 A1 | 4/2009 |
| WO | WO 2010/132847 A1 | 11/2010 |
| WO | WO 2011/133933 A2 | 10/2011 |
| WO | WO 2013/192317 A2 | 12/2013 |

OTHER PUBLICATIONS

Flotte and Buning, Severe Toxicity in Nonhuman Primates and Piglets with Systemic High-Dose Administration of Adeno-Associated Virus Serotype 9-Like Vectors: Putting Patients First, Human Gene Therapy, vol. 29, No. 3, 2018, pp. 283-284.*
Byrne, BJ, Safety First: Perspective on Patient-Centered Development of AAV Gene Therapy Products, Molecular Therapy vol. 26 No. 3 Mar. 2018, 669-671.*
Shanks et al, Are animal models predictive for humans?, BioMed Central, 2009, pp. 1-20.*
Colella et al, Emerging Issues in AAV-Mediated In Vivo Gene Therapy, Molecular Therapy: Methods & Clinical Development vol. 8 Mar. 2018, pp. 87-104.*
Duke Protocol No. Pro00088212, A Phase 1 Study of the Safety of AAV2/8-LSPhGAA in Late-onset Pompe disease, 2018, pp. 1-v and 1-32.*
Mendell et al, Single-Dose Gene-Replacement Therapy for Spinal Muscular Atrophy, N Engl J. Med 2017; 377:1713-1722.*
Mendell et al, Single-Dose Gene-Replacement Therapy for Spinal Muscular Atrophy, NEJM, pp. 1-15, 2018.*
Angelini et al., Enzyme replacement therapy for Pompe disease. Curr Neurol Neurosci Rep. Feb. 2012;12(1):70-5. doi: 10.1007/s11910-011-0236-5.
Brenner et al., Overview of gene therapy clinical progress including cancer treatment with gene-modified T cells. Hematology Am Soc Hematol Educ Program. 2009:675-81. doi: 10.1182/asheducation-2009.1.675.
Byrne et al., Pompe disease gene therapy. Hum Mol Genet. Apr. 15, 2011;20(R1):R61-8. doi: 10.1093/hmg/ddr174. Epub Apr. 25, 2011.
Ito et al., Viral vector-mediated [corrected] expression of human collagen Q in cultured cells. Chem Biol Interact. Sep. 25, 2008;175(1-3):346-8. doi: 10.1016/j.cbi.2008.02.003. Epub Feb. 14, 2008.
Kwissa et al., Efficient vaccination by intradermal or intramuscular inoculation of plasmid DNA expressing hepatitis B surface antigen under desmin promoter/enhancer control. Vaccine. May 8, 2000;18(22):2337-44.
Li et al., High level desmin expression depends on a muscle-specific enhancer. J Biol Chem. Apr. 5, 1991;266(10):6562-70.
Pacak et al., Characterization of AAV2/9 mediated gene therapy for the cardiac phenotype in a mouse model of pompe disease, National High magnetic field Laboratory 2005 Research Report.
Pacak et al., rAAV2/9 Mediated Gene Delivery of Acid l[alpha]l-Glucosidase Corrects the Cardiac Phenotype in a Mouse Model of Pompe Disease. Molecular Therapy (2006) 13,IS12; doi: 10.1016/j.ymthe.2006.08.040.
Pacak et al., AAV Vectors for Cardiac Gene Transfer: Experimental Tools and Clinical Opportunities, Molecular Therapy, 2011, vol. 19, pp. 1582-1590.
Raoul et al., ALS, IGF-1 and gene therapy: 'it's never too late to mend', Gene Therapy (2004) 11, 429-430.
Russell, Replicating vectors for gene therapy of cancer: risks, limitations and prospects. Eur J Cancer. 1994;30A(8):1165-71.
Sun et al., Correction of multiple striated muscles in murine Pompe disease through adeno-associated virus-mediated gene therapy. Mol Ther. Aug. 2008;16(8):1366-71. doi: 10.1038/mt.2008.133. Epub Jun. 17, 2008.
Sun et al., Efficacy of an adeno-associated virus 8-pseudotyped vector in glycogen storage disease type II. Mol Ther. Jan. 2005;11(1):57-65.
Thomas et al., Progress and problems with the use of viral vectors for gene therapy. Nat Rev Genet. May 2003;4(5):346-58.
Verma et al., Gene therapy—promises, problems and prospects. Nature. Sep. 18, 1997;389(6648):239-42.
Bercury et al., AAV2/8 Mediated-Efficacy and Immune Tolerance in a Pompe Disease Mouse Model. Molecular Therapy. May 2005; 11(S1):S96-S97.
Manno et al., Successful transduction of liver in hemophilia by AAV-Factor IX and limitations imposed by the host immune response. Nat Med. Mar. 2006;12(3):342-7. Epub Feb. 12, 2006.
Pacak, Gene Delivery Strategies for the Treatment of Cardiac and Skeletal Muscle in Murine Models of Muscular Dystrophy. A Dissertation presented to the Graduate School of the University of Florida in partial fulfillment of the requirements for the Degree of Doctor of Philosophy. 2006; UMI No. 3228798. 151 pages.
Rang et al., Pharmacology: Section 2: Chemical Mediators. Churchill Livingstone. 5$^{th}$ Edition; 2003:156.
Salmon et al., Safety profile of recombinant adeno-associated viral vectors: focus on alipogene tiparvovec (Glybera®). Expert Rev Clin Pharmacol. Jan. 2014;7(1):53-65. doi: 10.1586/17512433.2014. 852065. Epub Nov. 25, 2013.
Weinstein et al., Adeno-associated virus-mediated correction of a canine model of glycogen storage disease type Ia. Hum Gene Ther. Jul. 2010;21(7):903-10. doi: 10.1089/hum.2009.157.
Zhou et al., Progress of research on acetylcholinesterase in neuromuscular junction. Chin. J. Rehabil. Theory Practice. Mar. 2006;12(3): 235-6.
Borselli et al., Functional muscle regeneration with combined delivery of angiogenesis and myogenesis factors. Proc Natl Acad Sci USA. Feb. 23, 2010;107(8):3287-92. doi: 10.1073/pnas. 0903875106. Epub Dec. 4, 2009.
Duan et al., Enhancement of muscle gene delivery with pseudotyped adeno-associated virus type 5 correlates with myoblast differentiation. J Virol. Aug. 2001;75(16):7662-71.
Duan, Systemic AAV Micro-dystrophin Gene Therapy for Duchenne Muscular Dystrophy. Mol Ther. Oct. 3, 2018;26(10):2337-2356. doi: 10.1016/j.ymthe.2018.07.011. Epub Jul. 17, 2018.
Han et al., Low-Dose Liver-Targeted Gene Therapy for Pompe Disease Enhances Therapeutic Efficacy of ERT via Immune Tolerance Induction. Mol Ther Methods Clin Dev. Jan. 11, 2017;4:126-136. doi: 10.1016/j.omtm.2016.12.010. eCollection Mar. 17, 2017.
Kaufmann, AVXS-101, a clinical phase ghe replacement therapy for spinal muscular atrophy. Apr. 23, 2019. National Academy of Medicine, Neuroscience Forum. 17 pages.
Kishnani et al., Liver depot gene therapy for Pompe disease. Ann Transl Med. Jul. 2019;7(13):288. doi: 10.21037/atm.2019.05.02.
Mah et al., Physiological correction of Pompe disease by systemic delivery of adeno-associated virus serotype 1 vectors. Mol Ther. Mar. 2007;15(3):501-7. Epub Jan. 23, 2007.
Robbins et al., Defining the therapeutic window in a severe animal model of spinal muscular atrophy. Hum Mol Genet. Sep. 1, 2014;23(17):4559-68. doi: 10.1093/hmg/ddu169. Epub Apr. 9, 2014.
Todd et al., Correcting Neuromuscular Deficits With Gene Therapy in Pompe Disease. Ann Neurol. Aug. 2015;78(2):222-34. doi: 10.1002/ana.24433. Epub Jun. 30, 2015.
Todd et al., Early Correction of Neuromuscular Deficits in Pompe Disease is Required for Restoration of Strength following Gene Therapy. Mol Ther. May 2015;23(S1):S158.
Tosoloni et al., Motor Neuron Gene Therapy: Lessons from Spinal Muscular Atrophy for Amyotrophic Lateral Sclerosis. Front Mol

(56) References Cited

OTHER PUBLICATIONS

Neurosci. Dec. 7, 2017;10:405. doi: 10.3389/fnmol.2017.00405. eCollection 2017.

* cited by examiner

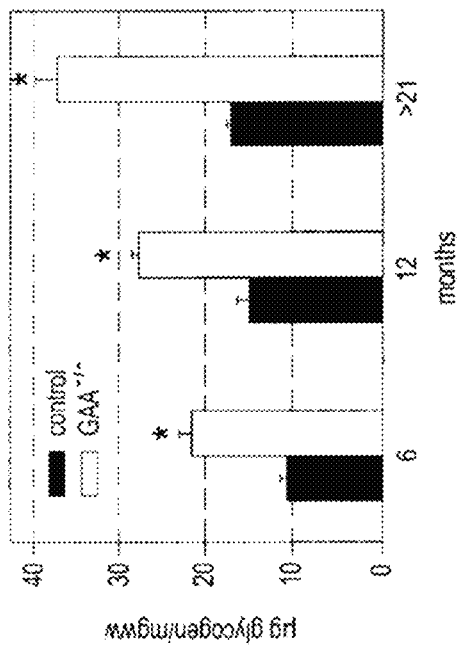
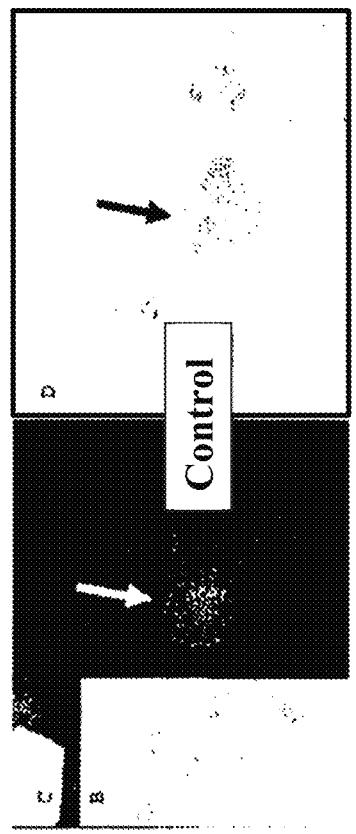 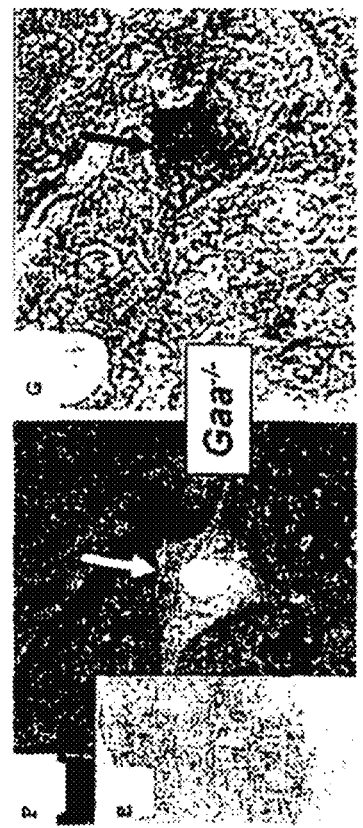
FIG. 17A FIG. 17B FIG. 17C FIG. 17D FIG. 17E FIG. 17F FIG. 17G AAV9 Systemic Body Weight AAV9 Systemic Cardiac Function Wild-type  Gaa -/-

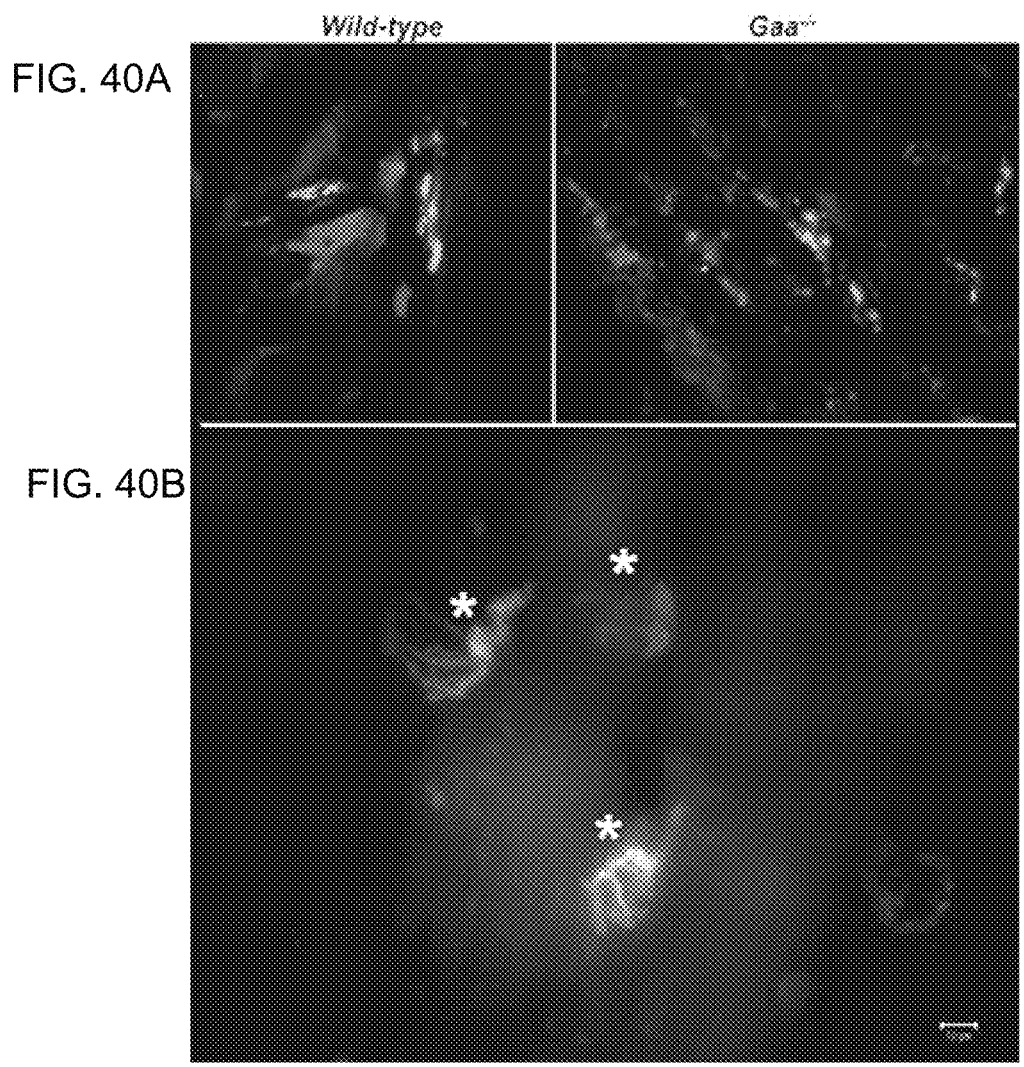

COMPOSITIONS AND METHODS FOR TREATING DISEASES

CROSS-REFERENCE TO RELATED APPLICATIONS

The present application is a continuation-in-part of U.S. application Ser. No. 13/527,350 13/527,350, filed Jun. 19, 2012, now abandoned; which is a continuation-in-part of U.S. application Ser. No. 12/305,869, filed Apr. 12, 2010, now abandoned; which is a § 371 national phase application of International Application No. PCT/US2008/054911, filed Feb. 25, 2008, which claims the priority benefit of U.S. Provisional Application No. 60/891,369, filed Feb. 23, 2007, all of which are incorporated herein by reference in their entirety.

STATEMENT REGARDING FEDERALLY-SPONSORED RESEARCH OR DEVELOPMENT

This invention was made with government support under grant numbers HL059412 and HL095282, awarded by the National Institutes of Health. The government has certain rights in the invention.

FIELD OF THE INVENTION

The invention relates generally to the fields of molecular biology, gene therapy, and medicine. In one embodiment, the invention provides a gene therapy-based treatment for neuromuscular and lysosomal storage diseases.

BACKGROUND

Pompe disease is both a lysosomal and glycogen storage disorder resulting from acid α-glucosidase (GAA) deficiency. GAA is normally active in the lysosome where it degrades excess glycogen by cleaving the α-1,4 and α-1,6 glycosidic bonds. Without adequate GAA activity, massive amounts of glycogen accumulate in all cells. Despite systemic accumulation of lysosomal glycogen in Pompe disease, skeletal and cardiac muscle dysfunction have been traditionally viewed as the principle basis for muscle weakness in this disorder.

SUMMARY

The present invention provides rAAV vectors for delivery of therapeutic genes into various tissues, organs, and cells including skeletal muscle, the heart, and the CNS, for restoration of neuromuscular junction integrity, and/or for treatment of neuromuscular diseases and glycogen storage diseases. Advantageously, the rAAV vectors of the present invention provide long-term, sustained expression of the therapeutic gene of interest in a subject.

In certain embodiments, the present invention provides treatment for neuromuscular diseases including, but not limited to, Pompe disease, amyotrophic lateral sclerosis, spinal muscular atrophy, multiple sclerosis, glycogen storage disease type 1a, limb Girdle muscular dystrophy, Barth syndrome, and myasthenia gravis.

In one embodiment, compositions and methods for treating lysosomal storage diseases (e.g., glycogen storage diseases such as Pompe) are described herein.

Unless otherwise defined, all technical terms used herein have the same meaning as commonly understood by one of ordinary skill in the art to which this invention belongs.

In one embodiment, a method as described herein includes administering to a mammalian subject having an acid alpha-glucosidase deficiency a composition including at least one rAAV virion including a polynucleotide encoding acid alpha-glucosidase, the polynucleotide interposed between a first AAV inverted terminal repeat and second AAV inverted terminal repeat, wherein administration of the composition results in increased motoneuron function in the mammalian subject. The mammalian subject can have Pompe disease. The composition can be administered intravenously intrathecally, or intramuscularly. In one embodiment, the at least one rAAV virion can include serotype 1, 8, 9, and/or rh10 capsid proteins. The composition can be administered to the diaphragm of the mammalian subject and travel to at least one motoneuron by retrograde transport or can be administered directly to the central nervous system.

Another method as described herein includes administering to a mammalian subject having Pompe disease a composition including at least one viral vector encoding acid alpha-glucosidase, wherein administration of the composition results in increased motoneuron function in the mammalian subject and treats Pompe disease. The at least one viral vector can be a rAAV vector. The composition can be administered by intrathecal, intravenous, intramuscular, or parenteral route. In one embodiment, the rAAV vector can be within a rAAV virion including serotype 1, 8, 9, and/or rh10 capsid proteins.

The composition can be administered to the diaphragm of the mammalian subject and travel to at least one motoneuron by retrograde transport, or can be administered to the central nervous system.

Although compositions and methods similar or equivalent to those described herein can be used in the practice or testing of the present invention, suitable compositions and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 1A, FIG. 1B and FIG. 1C show X-Gal-stained cryosections from hearts injected with AAV2/1 (FIG. 1A), AAV2/8 (FIG. 1B), and AAV2/9 (FIG. 1C). FIG. 1D shows β-Galactosidase enzyme levels in hearts (n=5).

FIG. 2A shows the biodistribution across muscle tissues in comparison to myocardium. Ht indicates heart: Di, diaphragm; Qu, quadriceps; So, soleus; ED, extensor digitorum longus; TA, tibialis anterior. FIG. 2B shows the expression biodistribution in nonskeletal muscle. Br indicates brain; Lu, lung; Sm, small intestine; Ki, kidney; Spl, spleen.

FIG. 3A: following delivery of transgene using rAAV2/9, expression levels plateaued in skeletal muscle at 4-weeks post-administration and continued to increase in heart for the 8-week duration of the experiment. FIG. 3B shows vector genomes per cell also continued to increase in cardiac tissue but not skeletal muscle for the duration of the experiment. FIG. 3C shows RNA transcripts also increased in cardiac tissue for the duration of the experiment (n=4 per time point).

FIG. 10A is a graph showing the results of a 30-sec peak amplitude of the moving time average for control and $GAA^{-/-}$ mice. $PaCO_2$ values are similar.

FIG. 17A, FIG. 17B, FIG. 17C, FIG. 17D, FIG. 17E, FIG. 17F and FIG. 17G are a graph (FIG. 17A) and a series of photographs (FIG. 17B-FIG. 17G) of phrenic motoneurons illustrating cervical spinal cord ($C_3$-$C_5$) glycogen content. Biochemical glycogen quantification (μg glycogen/mg wet weight) of the spinal cord in control and $Gaa^{-/-}$ mice at 6, 12 and >21 months of age (FIG. 17A). *=$Gaa^{-/-}$ different from control, p<0.01. †=6 months different from >21 months, p<0.01. Multiple motor pools exhibit positive staining for glycogen in the $Gaa^{-/-}$ mouse cervical spinal cord (FIG. 17E) vs. control (FIG. 17B). Phrenic motoneurons were labeled with Fluoro-Gold® in control (FIG. 17C) and $Gaa^{-/-}$ (FIG. 17F) mice. $Gaa^{-/-}$ labeled phrenic motoneuron exhibits a more intense stain for glycogen (FIG. 17G) vs. a control phrenic motoneuron (FIG. 17D).

(FIG. 26C) GAA activity levels at the site of injection (TA) result in a significant increase in enzymatic level in Gaa$^{-/-}$ mice.

(FIG. 28A) Positive detection of AAV reporter constructs (*) at the site of injection in fixed, intact brain and spinal cord preparations. (FIG. 28B) Cross-sectional epifluorescent detection of AAV-GFP demonstrates transduction of the phrenic motor pool.

(FIG. 34A) shows ejection fraction at three months post-injection. AAV-DES treated animals exhibit significant improvement in ejection fraction. Mean and sem (n=6). (FIG. 34B) shows that all treatments resulted in a significant increase in body weight at one and three months post injection. (FIG. 34C) shows PR intervals at one month and three months post treatment. (FIG. 34D) shows improvement of cardiac function post intravenous injection. (FIG. 34E) shows GAA enzymatic activity in the heart after intravenous administration. (FIG. 34F) In vitro force-frequency measurements of diaphragm of AAV2/9-CMV and AAV2/9-DES-GAA treated animals exhibit increased max titanic force. Mean and sem (n=6). *P value≤0.05 as compared to untreated mice. The AAV2/9-GAA treatment results in an improvement of contractile function at frequencies above 60 Hz. (FIG. 34G) shows GAA enzyme activity in respiratory muscle. (FIG. 34H) shows vector genome copies in the cardiac, diaphragm, and spinal cord after intravenous administration of AAV2/9-CMV and AAV2/9-DES-GAA vectors. (FIG. 34I) shows the GAA expression level after intravenous administration of AAV2/9-CMV and AAV2/9-DES-GAA vectors.

(FIG. 37A) Silver stained PAGE of crude lysate (lane 1), crude lysate after microfluidization (lane 2), AAV2/9-retaining supernatant after pI precipitation (lane 3); (FIG. 37B) Silver stained PAGE of pI-purified rAAV2/9 containing fractions (lanes 2 to 7) after SP Sepharose IEC and concentration.

FIG. 40A and FIG. 40B are an evaluation of neuromuscular junction integrity of the soleus in wild-type and $Gaa^{-/-}$ mice. (FIG. 40A) Longitudinal sections from soleus muscle. Note the marked changes in $Gaa^{-/-}$ where dissociation of the neuromuscular junction is evident. (FIG. 40B) Neuromuscular junction in whole mount of mouse diaphragm. Typical intact neuromuscular junction (arrow) and atypical neuromuscular junction (*) in the $Gaa^{-/-}$ diaphragm. Alpha-bungarotoxin (red) and NeurofilamentH (green).

DETAILED DESCRIPTION

Figure 1A:
FIG. 1A, FIG. 1B and FIG. 1C are scans of photographs of stained heart tissues

The present invention provides rAAV vectors for delivery of therapeutic genes into various tissues, organs, and cells including skeletal muscle, the heart, and the CNS, for restoration of neuromuscular junction integrity, and/or for treatment of neuromuscular diseases. Advantageously, the rAAV vectors of the present invention provide long-term, sustained expression of the therapeutic gene of interest in a subject.

In one embodiment, the present invention provides a recombinant adeno-associated virus (AAV) virion, comprising a rAAV vector that comprises a heterologous nucleic acid molecule (also referred to as a transgene or a therapeutic gene), and the AAV vector is encapsidated by a viral capsid.

In one specific embodiment, the rAAV virion comprises a rAAV vector that comprises a heterologous nucleic acid molecule (also referred to as a transgene or a therapeutic gene) encoding a protein or polypeptide of interest,
wherein the heterologous nucleic acid molecule is operably linked to control elements (e.g., promoter, enhancer) capable of directing in vivo or in vitro expression of the protein or polypeptide of interest,
wherein the heterologous nucleic acid molecule is flanked on each end with an AAV inverted terminal repeat, and
wherein the rAAV vector is encapsidated by a viral capsid.

In a preferred embodiment, the present invention pertains to pseudotyped rAAV vectors. In certain embodiments, the present invention pertains to rAAV2/x vectors, which comprise the vector genome of AAV2 and capsids of AAVx (e.g., AAV1, AAV3, AAV4, AAV5. AAV6, AAV7, AAV8, AAV9, or AAVrh10). In preferred embodiments, the present invention pertains to rAAV2/1 (also referred to in the Figures as rAAV1), rAAV2/5, rAAV2/8 (also referred to in the Figures as rAAV8), and rAAV2/9 (also referred to in the Figures as rAAV9) vectors.

In one embodiment, the rAAV vector comprises a cytomegalovirus (CMV) promoter. In another embodiment, the rAAV vector comprises a desmin (DES) promoter. In one specific embodiment, the rAAV vector comprises regulatory elements for tissue-specific expression of the transgene, such as for example, myocyte specific enhancer factor 2 (MEF2) and myoD enhancer element.

In another embodiment, the present invention provides a method for treating a neuromuscular disease, comprising administering to a subject in need of such treatment, an effective amount of a composition comprising a rAAV vector of the present invention.

In one specific embodiment, the present invention provides a method for restoring neuromuscular junction integrity and/or for improving impaired neuromuscular junction integrity in a subject, wherein the method comprises administering to the subject, an effective amount of a composition comprising a rAAV vector of the present invention. In certain embodiments, the impaired neuromuscular integrity is caused by neuromuscular disease or injury.

In another embodiment, the present invention provides a method for treating a disease by delivery of a therapeutic gene into cells of interest, wherein the method comprises introducing into a cell, an effective amount of a composition comprising a rAAV vector of the present invention.

In certain embodiments, the rAAV vector of the present invention is administered via intravenous, intramuscular, intrathoracic, intrathecal, or intraspinal injection. In certain embodiments, the rAAV vectors are administered to the skeletal muscle, diaphragm, costal, and/or cardiac muscle cells of a subject. In certain embodiments, the rAAV vectors are delivered to neuronal cells in the peripheral and/or central nervous system via direct or retrograde transport.

In certain embodiments, the present invention provides treatment for neuromuscular diseases including, but not limited to, Pompe disease, amyotrophic lateral sclerosis, spinal muscular atrophy, multiple sclerosis, glycogen storage disease type 1a, limb Girdle muscular dystrophy. Barth syndrome, and myasthenia gravis.

In one embodiment, the rAAV vector comprises a therapeutic gene encoding GAA and the rAAV vector is delivered into the central nervous system (e.g., the spinal cord and the brain) to reduce glycogen accumulation in the central nervous system in a subject with Pompe disease.

In another embodiment, the present invention provides treatment for a neuromuscular disease that is not Pompe disease. In another embodiment, the present invention improves impaired neuromuscular junction integrity in a subject that does not have Pompe disease. The animal model of Pompe disease is used as an example to illustrates that the rAAV vectors of the present invention result in effective delivery of the therapeutic gene encoding GAA into cells, tissues and organs of interest. The animal model of Pompe disease is also used as an example to illustrate that the rAAV vectors of the present invention result in improvement of neuromuscular junction integrity. One skilled in the art, in view of these examples, would readily recognize that the rAAV vectors of the present invention can also be used to deliver other therapeutic genes to cells, tissues and organs of interest (e.g., neuronal cells), thereby providing treatment for neuromuscular diseases and/or improving neuromuscular junction integrity in a subject that does not have Pompe disease.

In certain embodiments, compositions and methods including rAAV virions having rAAV vectors expressing GAA for treating a mammalian subject having a GAA deficiency are described herein. In one embodiment, compositions comprising rAAV serotypes (e.g., serotypes 1-10, or derivatives thereof) expressing therapeutic molecules in combination with an intravenous route of administration results in rAAV serotypes that are more readily able to cross the vasculature and efficiently transduce a particular tissue type (e.g., cardiac tissue, diaphragm tissue, central nervous system tissue.

In another embodiment, the AAV are modified to include ligands which are cell and/or tissue specific so that the compositions are administered systemically and absorption into targets is directed and specific.

When taking into consideration those characteristics desirable in a vehicle for gene delivery in a mammal, the (4.7-kb) nonpathogenic parvovirus rAAV emerged as an attractive choice, mainly because of its small size and proven ability to persist for long periods of time in infected cells, rAAV is a single-stranded DNA virus that requires a helper, such as herpes virus or adenovirus, to replicate. With recent discoveries of additional serotypes of rAAV, it has become possible to select those with the most advantageous tropisms to target and/or evade tissues as desired for specific applications. The most optimal gene-delivery system for any therapeutic application will combine a clinically advantageous physical delivery route with the rAAV serotype that has the highest natural affinity for a specifically targeted tissue of interest.

In a typical embodiment, a composition includes a rAAV virion having a rAAV vector encoding GAA that improves phrenic nerve function in a mammalian subject having a GAA deficiency (e.g., Pompe disease). The rAAV virion can be directly transduced into the central nervous system, or can be transduced into other tissue types (e.g., diaphragm) and transported to the central nervous system via retrograde transport. By improving phrenic nerve activity in a mammalian (e.g., human) subject having a GAA deficiency, resulting respiratory deficits may be corrected (e.g., reduced ventilation, reduced cardiac function, etc.)

In another embodiment, administration of the rAAV is performed via intravenous administration (e.g., systemic delivery). In a typical embodiment, systemic delivery is used, as it impacts cardiac, muscle and respiratory aspects of the disease.

Other examples of different therapeutic molecules for treating lysosomal storage diseases (LSDs) include without limitation: Hurler disease: α-L-iduronidase: Hunter disease: iduronate sulfatase; Sanfilippo: heparan N-sulfatase; Morquio A: galactose-6-sulfatase; Morquio B: acid-β-galactosidase; Sly disease: β-glucoronidase: 1-cell disease: N-acetylglucosamine-1-phosphotransferase; Schindler disease: α-N-acetylgalactosaminidase (α-galactosidase B); Wolman disease: acid lipase; Cholesterol ester: acid lipase; storage disease; Farber disease: lysosomal acid ceramidase; Niemann-Pick disease: acid sphingomyelinase; Gaucher's disease: β-glucosidase (glucocerebrosidase); Krabbe disease: galactosylceramidase; Fabry disease: α-galactosidase A; GM1 gangliosidosis: acid β-galactosidase; Galactosialidosis: β-galactosidase and neuraminidase; Tay-Sach's disease: hexaminidase A; Sandhoff disease: hexosaminidase A and B; Neuronal Ceroid: Palmitoyl Protein Thioesterase (PPT); Neuronal Ceroid: Tripeptidyl Aminopeptidase I1 (TPP-I). Heterologous nucleic acid molecules or transgenes encoding the therapeutic molecules of interest can be inserted into to the rAAV vectors of the invention for treatment of lysosomal storage diseases.

Glycogen storage disease type II (GSD II; Pompe disease; acid maltase deficiency) is caused by deficiency of the lysosomal enzyme acid α-glucosidase (acid maltase). Three clinical forms are distinguished: infantile, juvenile and adult. Infantile GSD II has its onset shortly after birth and presents with progressive muscular weakness and cardiac failure. This clinical variant is fatal within the first two years of life. Symptoms in adult and juvenile patients occur later in life, and skeletal muscles and neurons are primarily involved. The patients eventually die due to respiratory insufficiency. Patients may exceptionally survive for more than six decades. There is a good correlation between the severity of the disease and the residual acid α-glucosidase activity, the activity being 10-20% of normal in late onset and less than 2% in early onset forms of the disease.

Pompe disease is an inborn error of metabolism with deficiency of the lysosomal glycogen degrading enzyme acid α-glucosidase (GAA), which ultimately results in glycogen accumulation in all tissues, especially striated muscle. Historically, muscle weakness has been viewed as the major contributor to respiratory deficiency in the patient population, yet other mechanisms have not been investigated. To further evaluate contributing mechanisms of respiratory insufficiency, an animal model of Pompe disease, the $Gaa^{-/-}$ mouse model, was used. Ventilation was quantified in $Gaa^{-/-}$ and control mice during quiet breathing and hypercapnia. All ventilation variables were attenuated in $Gaa^{-/-}$ mice at 6, 12 and >21 months of age and were accompanied by elevated glycogen content of the cervical spinal cord ($C_3$-$C_5$). Transgenic mice that only express Gaa in skeletal muscle had minute ventilation similar to $Gaa^{-/-}$, although diaphragmatic muscle function was normal, demonstrating that a mechanism other than muscle dysfunction was contributing to ventilation impairments. Efferent phrenic nerve inspiratory burst amplitude (mV) was lower in $Gaa^{-/-}$ mice (5.2 f 1.2 mV) compared to controls (49.7±13.9 mV) with similar $PaCO_2$ levels (53.1 & 1.2 vs. 52.2±1.4 mmHg). The data indicate that neural control of ventilation is deficient in Pompe disease and support the following conclusions: 1) $Gaa^{-/-}$ mice recapitulate clinical GSDII respiratory deficits, 2) spinal glycogen accumulation may impair motor output, and 3) respiratory neural control may be impaired in GSDII.

Infantile forms of Pompe have a rapid development of cardiomyopathy and display myopathy and neuorpathy leading to death typically in the first year of life. Using periodic acid-Schiff's reagent (PAS) staining to assess diaphragm sections in mice, the progression of glycogen deposition in $Gaa^{-/-}$ animals is examined. At 12 months of age widespread and diffuse glycogen 5 deposits are apparent in diaphragm sections of $Gaa^{-/-}$ animals. Not only is there a decline in diaphragmatic contractile properties in $Gaa^{-/-}$ animals, there is also a progressive worsening of contractile function with age. In vitro force frequency measurements illustrate a progressive loss of contractile function in $Gaa^{-/-}$ mice at 3, 6, and 12 months of age. The deficiency in GAA leads to inefficient glycogen clearance, leading to a disruption of cellular morphology and function. Biopsies of Pompe patients also show vacuolization, lysosomal glycogen accumulation and consequent respiratory muscle weakness.

In addition, the effect of glycogen accumulation within the central nervous system and its effect on skeletal muscle function have been recently discovered. The present inventors have detected substantial glycogen deposition within the $Gaa^{-/-}$ mouse spinal cord. Specifically, PAS staining shows the degree and localization of glycogen in the motor neuron in cross-sections of spinal cord. The motor neuron appears to be swollen in some cases and varies in the degree across the section. Phrenic nerve recordings in wild-type and Gaa$^{-/-}$ animals display obvious discrepancies in the level of burst amplitude upon hypercapnic challenge. The inventors also discovered that a muscle-specific GAA mouse (expressed GAA in skeletal muscle but not in the CNS) still showed functional respiratory deficits during plethysmography measurements. The results indicate CNS-mediated respiratory dysfunction in Gaa$^{-/-}$ animals and in Pompe patients.

A remarkable characteristic of Pompe disease occurring in the animal model is the severe kyphosis as a result of the drastic skeletal myopathy. Gaa$^{-/-}$ animals develop severe kyphosis at about 9-12 months of age. The development of neutropenia in Pompe affected individuals has been described and this is apparent in the animal model where muscle weakness ultimately affects nutrient intake. Gaa$^{-/-}$ mice treated with AAV-CMV-GAA do not develop kyphosis. With the preservation of skeletal muscle mass and strength, treated animals are able to maintain adequate nutritional intake and therefore function similar to wild-type mice.

The Gaa$^{-/-}$ mouse model shows the progressive pathology associated with glycogen storage in the CNS and skeletal muscle. The present inventors have reported the specific role of the CNS contribution to respiratory dysfunction in the murine model of Pompe disease. In other neuromuscular disorders, adaptations in the NMJ and motor neuron occur as a result of CNS or skeletal muscle abnormalities. It is reported that fatigue is evident in late-onset Pompe patients and may be caused by deficiencies that are neural-based but for the majority remain centered around skeletal muscle defects.

Figures 38A, 38B:
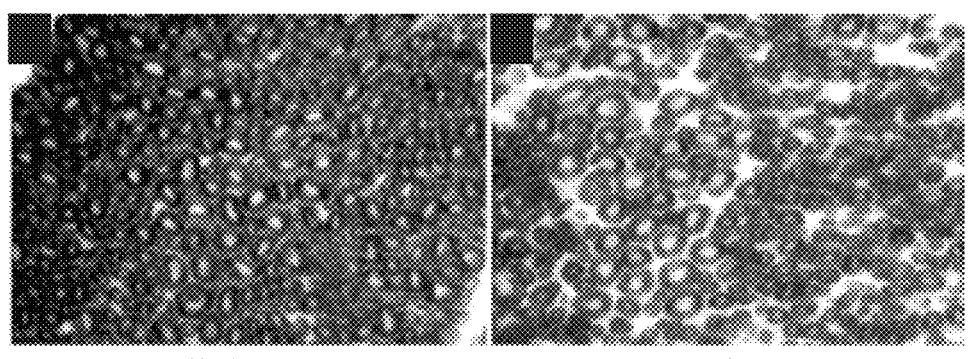
FIG. 38A and FIG. 38B are an evaluation of cross-sections of the sciatic nerve in wild-type (FIG. 38A) and $Gaa^{-/-}$ mice (FIG. 38B). $Gaa^{-/-}$ mice display irregular morphometry and an increase in the amount of extracellular matrix.
Figure 39:
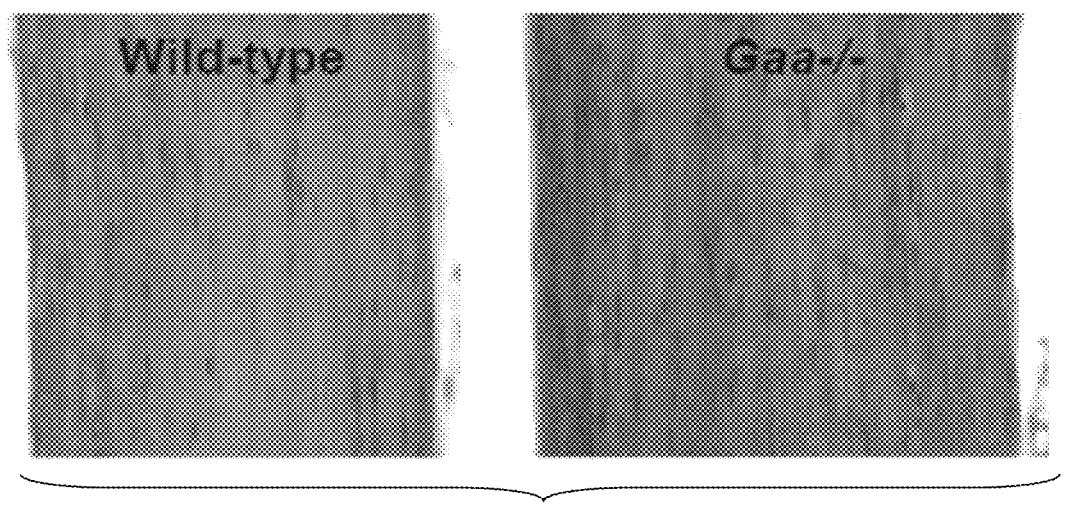
FIG. 39 shows longitudinal nerve section stained for H & E. Comparison of wild-type and $Gaa^{-/-}$ mice reveals an increase in nuclear staining indicates dedifferentiation and proliferation of Schwann cells.

In accordance with the present invention, sciatic nerves were harvested from 18 month old wild-type or Gaa$^{-/-}$ animals. As shown in FIG. 38, nerve cross-sections from Gaa$^{-/-}$ animals appear to vary in the amount and thickness of myelin, the diameter or axons, and show an increase in the amount of extracellular matrix. In addition, longitudinal sections of sciatic nerve from Gaa$^{-/-}$ animals display an increase in nuclear staining, indicting dedifferentiation and proliferation of Schwann cells (FIG. 39). The staining patterns of the sciatic nerve samples in Pompe disease are also observed in traditional neuromuscular diseases such as amyotrophic lateral sclerosis, spinal muscular atrophy, multiple sclerosis, glycogen storage disease type 1a, limb Girdle muscular dystrophy, Barth syndrome, and myasthenia gravis.

The fatigue present in patients with neuromuscular diseases could be due to impairments in E-C coupling and other mechanisms. Upon comparison of the neuromuscular junction in longitudinal sections from the soleus and whole mount diaphragm preparations (FIG. 40), the present inventors noted abrupt changes in association of the neuromuscular junction. The incorporation of whole-mount diaphragm preparations provides an in-depth picture of the overall status of neuromuscular junctions. Diaphragm preparations from Gaa$^{-/-}$ animals display an advanced and clear distortion of junctions compared to wild-type diaphragm.

Gaucher's disease is an autosomal recessive lysosomal storage disorder characterized by a deficiency in a lysosomal enzyme, glucocerebrosidase ("GCR"), which hydrolyzes the glycolipid glucocerebroside. In Gaucher's disease, deficiency in the degradative enzyme causes the glycolipid glucocerebroside, which arises primarily from degradation of glucosphingolipids from membranes of white blood cells and senescent red blood cells, to accumulate in large quantities in the lysosome of phagocytic cells, mainly in the liver, spleen and bone marrow. Clinical manifestations of the disease include splenomegaly, hepatomegaly, skeletal disorders, thrombocytopenia and anemia. For example, see U.S. Pat. No. 6,451,600.

Tay-Sachs disease is a fatal hereditary disorder of lipid metabolism characterized especially in CNS tissue due to deficiency of the A (acidic) isozyme of β-hexosaminidase. Mutations in the HEXA gene, which encodes the a subunit of (i-hexosaminidase, cause the A isozyme deficiency. Tay-Sachs disease is a prototype of a group of disorders, the GM2 gangliosidosis, characterized by defective GM2 ganglioside degradation. The GM2 ganglioside (monosialylated ganglioside 2) accumulates in the neurons beginning in the fetus. GM1 gangliosidosis is caused by a deficiency of β-galactosidase, which results in lysosomal storage of GM1 ganglioside (monosialylated ganglioside 1). Sandhoff disease results from a deficiency of both the A and B (basic) isozymes of (3-hexosaminidase. Mutations in the HEXB gene, which encodes the β subunit of β-hexosaminidase, cause the B isozyme deficiency.

Another LSD results from a genetic deficiency of the carbohydrate-cleaving, lysosomal enzyme α-L-iduronidase, which causes mucopolysaccharidosis 1 (MPS I) (E. F. Neufeld and J. Muenzer, 1989; U.S. Pat. No. 6,426,208). See also "The mucopolysaccharidoses" in *The Metabolic Basis of Inherited Disease* (C. R. Scriver, A. L. Beaudet, W. S. Sly and D. Valle, Eds.), pp. 1565-1587, McGraw-Hill, New York. In a severe form, MPS I is commonly known as Hurler syndrome and is associated with multiple problems such as mental retardation, clouding of the cornea, coarsened facial features, cardiac disease, respiratory disease, liver and spleen enlargement, hernias, and joint stiffness. Patients suffering from Hurler syndrome usually die before age 10. In an intermediate form known as Hurler-Scheie syndrome, mental function is generally not severely affected, but physical problems may lead to death by the teens or twenties. Scheie syndrome is the mildest form of MPS 1 and is generally compatible with a normal life span, but joint stiffness, corneal clouding and heart valve disease cause significant problems.

Fabry disease is an X-linked inherited lysosomal storage disease characterized by symptoms such as severe renal impairment, angiokeratomas, and cardiovascular abnormalities, including ventricular enlargement and mitral valve insufficiency (U.S. Pat. No. 6,395,884). The disease also affects the peripheral nervous system, causing episodes of agonizing, burning pain in the extremities. Fabry disease is caused by a deficiency in the enzyme α-galactosidase A (α-gal A), which results in a blockage of the catabolism of neutral glycosphingolipids, and accumulation of the enzyme's substrate, ceramide trihexoside, within cells and in the bloodstream. Due to the X-linked inheritance pattern of the disease, essentially all Fabry disease patients are male. Although a few severely affected female heterozygotes have been observed, female heterozygotes are generally either asymptomatic or have relatively mild symptoms largely limited to a characteristic opacity of the cornea. An atypical variant of Fabry disease, exhibiting low residual α-gal A activity and either very mild symptoms or apparently no other symptoms characteristic of Fabry disease, correlates with left ventricular hypertrophy and cardiac disease. It has been speculated that reduction in α-gal A may be the cause of such cardiac abnormalities.

I-cell disease is a fatal lysosomal storage disease caused by the absence of mannose-6-phosphate residues in lysosomal enzymes. N-acetylglucosamine-1-phospho-transferase is necessary for generation of the M6P signal on lysosomal proenzymes.

LSDs which affect the central nervous system require that the replacement enzyme cross the BBB. To accomplish this, the source of the replacement enzyme may be placed within the brain of the subject, thereby bypassing the BBB. Thus, glial progenitor cells are ideal therapeutic delivery vehicles because of their exceptional capacity to multiply, migrate and differentiate into oligodendrocyte and astrocyte subtypes. Thus, LSDs that affect the central nervous system may be treated in a variety of manners, including genetically encoding glial progenitor cells to secrete lysosomal proenzymes, for example, lysosomal proenzymes, and delivering the cells to damaged tissues and/or replacing the defective cells.

In another embodiment, the compositions of the instant invention are used to treat neurological disorders. A "neurological disorder" refers to any central nervous system (CNS) or peripheral nervous system (PNS) disease that is associated with neuronal or glial cell defects including but not limited to neuronal loss, neuronal degeneration, neuronal demyelination, gliosis (i.e., astrogliosis), or neuronal or extraneuronal accumulation of aberrant proteins or toxins (e.g., β-amyloid, or α-synuclein). The neurological disorder can be chronic or acute.

Exemplary neurological disorders include but are not limited to Gaucher's disease and other LSDs including Fabry disease, Tay-Sachs disease, Pompe disease, and the mucopolysaccharidoses; Parkinson's disease; Alzheimer's disease; Amyotrophic Lateral Sclerosis (ALS); Multiple Sclerosis (MS); Huntington's disease; Fredrich's ataxia; Mild Cognitive Impairment; and movement disorders (including ataxia, cerebral palsy, choreoathetosis, dystonia, Tourette's syndrome, kernicterus): tremor disorders, leukodystrophies (including adrenoleukodystrophy, metachromatic leukodystrophy, Canavan disease, Alexander disease. Pelizaeus-Merzbacher disease); neuronal ceroid lipofucsinoses; ataxia telangectasia; and Rett syndrome. This term also includes cerebrovascular events such as stroke and ischemic attacks.

The term "subject," as used herein, describes an organism, including mammals such as primates. Mammalian species that can benefit from the subject methods include, but are not limited to, apes, chimpanzees, orangutans, humans, monkeys; and other animals such as dogs, cats, horses, cattle, pigs, sheep, goats, chickens, mice, rats, guinea pigs, and hamsters. Typically, the subject is a human.

In some embodiments, subjects with a "neurological disorder" include subjects at risk of developing a neurological disorder, disease or condition and/or subjects already diagnosed with a neurological disorder, disease or condition.

Therapeutic Molecules
Nucleic Acids for Modulating GAA Expression:

As an example, GAA is used to illustrate the invention. However, depending on the diseases, the therapeutic molecule can be substituted (infra). Transfer of a functional GAA protein into a cell or animal is accomplished using a nucleic acid that includes a polynucleotide encoding the functional GAA protein interposed between two AAV ITRs. The GAA-encoding polynucleotide sequence can take many different forms. For example, the sequence may be a native mammalian GAA nucleotide sequence such as one of the mouse or human GAA-encoding sequences deposited with Genbank as accession numbers NM_008064, NM_000152, X55080, X55079, M34425, and M34424. The GAA-encoding nucleotide sequence may also be a non-native coding sequence which, as a result of the redundancy or degeneracy of the genetic code, encodes the same polypeptide as does a native mammalian GAA nucleotide sequence. Other GAA-encoding nucleotide sequences within the invention are those that encode fragments, analogs, and derivatives of a native GAA protein. Such variants may be, e.g., a naturally occurring allelic variant of a native GAA-encoding nucleic acid, a homolog of a native GAA-encoding nucleic acid, or a non-naturally occurring variant of native GAA-encoding nucleic acid. These variants have a nucleotide sequence that differs from native GAA-encoding nucleic acid in one or more bases. For example, the nucleotide sequence of such variants can feature a deletion, addition, or substitution of one or more nucleotides of a native GAA-encoding nucleic acid. Nucleic acid insertions are generally of about 1 to 10 contiguous nucleotides, and deletions are generally of about 1 to 30 contiguous nucleotides. In most applications of the invention, the polynucleotide encoding a GAA substantially maintains the ability to convert phenylalanine to tyrosine.

The GAA-encoding nucleotide sequence can also be one that encodes a GAA fusion protein. Such a sequence can be made by ligating a first polynucleotide encoding a GAA protein fused in frame with a second polynucleotide encoding another protein (e.g., one that encodes a detectable label). Polynucleotides that encode such fusion proteins are useful for visualizing expression of the polynucleotide in a cell.

In order to facilitate long term expression, the polynucleotide encoding GAA is interposed between AAV inverted terminal repeats (ITRs) (e.g., the first and second AAV ITRs). AAV ITRs are found at both ends of a WT AAV genome, and serve as the origin and primer of DNA replication. ITRs are required in cis for AAV DNA replication as well as for rescue, or excision, from prokaryotic plasmids. The AAV ITR sequences that are contained within the nucleic acid can be derived from any AAV serotype (e.g., 1, 2, 3, 4, 5, 6, 7, 8, 9, 10) or can be derived from more than one serotype. For use in a vector, the first and second ITRs should include at least the minimum portions of a WT or engineered ITR that are necessary for packaging and replication.

In addition to the AAV ITRs and the polynucleotide encoding GAA, the nucleic acids of the invention can also include one or more expression control sequences operatively linked to the polynucleotide encoding GAA. Numerous such sequences are known. Those to be included in the nucleic acids of the invention can be selected based on their known function in other applications. Examples of expression control sequences include promoters, insulators, silencers, response elements, introns, enhancers, initiation sites, termination signals, and pA tails.

To achieve appropriate levels of GAA, any of a number of promoters suitable for use in the selected host cell may be employed. For example, constitutive promoters of different strengths can be used. Expression vectors and plasmids in accordance with the present invention may include one or more constitutive promoters, such as viral promoters or promoters from mammalian genes that are generally active in promoting transcription. Examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A and cytomegalovirus (CMV) promoters.

Examples of constitutive mammalian promoters include various housekeeping gene promoters, as exemplified by the β-actin promoter. As described in the examples below, the chicken beta-actin (CB) promoter has proven to be a particularly useful constitutive promoter for expressing GAA.

Inducible promoters and/or regulator) elements may also be contemplated for use with the nucleic acids of the invention. Examples of suitable inducible promoters include those from genes such as cytochrome P450 genes, heat shock protein genes, metallothionein genes, and hormone-inducible genes, such as the estrogen gene promoter. Another example of an inducible promoter is the tetVP 16 promoter that is responsive to tetracycline.

Tissue-specific promoters and/or regulatory elements are useful in certain embodiments of the invention. Examples of such promoters that may be used with the expression vectors of the invention include (1) creatine kinase, myogenin, alpha myosin heavy chain, human brain and natriuretic peptide, specific for muscle cells, and (2) albumin, alpha-1-antitrypsin, hepatitis B virus core protein promoters, specific for liver cells.

The invention also includes methods and compositions thereof which can be used to correct or ameliorate a gene defect caused by a multi-subunit protein. In certain situations, a different transgene may be used to encode each subunit of the protein. This may be desirable when the size of the DNA encoding the protein subunit is large, e.g., for an immunoglobulin or the platelet-derived growth factor receptor. In order for the cell to produce the multi-subunit protein, a cell would be infected with rAAV expressing each of the different subunits.

Alternatively, different subunits of a protein may be encoded by the same transgene. In this case, a single transgene would include the DNA encoding each of the subunits, with the DNA for each subunit separated by an internal ribosome entry site (IRES). The use of IRES permits the creation of multigene or polycistronic mRNAs. IRES elements are able to bypass the ribosome scanning model of 5' methylated cap-dependent translation and begin translation at internal sites. For example, IRES elements from hepatitis C and members of the picornavirus family (e.g., polio and encephalomyocarditis) have been described, as well an IRES from a mammalian mRNA. IRES elements can be linked to heterologous open reading frames. By virtue of the IRES element, each open reading frame is accessible to ribosomes for efficient translation. Thus, multiple genes can be efficiently expressed using a single promoter/enhancer to transcribe a single message. This is particularly useful when the size of the DNA encoding each of the subunits is sufficiently small that the total of the DNA encoding the subunits and the IRES is no greater than the maximum size of the DNA insert that the virus can encompass. For instance, for rAAV, the insert size can be no greater than approximately 4.8 kilobases; however, for an adenovirus which lacks all of its helper functions, the insert size is approximately 28 kilobases.

Useful gene products include hormones and growth and differentiation factors including, without limitation, insulin, glucagon, growth hormone (GH), parathyroid hormone (PTH), calcitonin, growth hormone releasing factor (GRF), thyroid stimulating hormone (TSH), adrenocorticotropic hormone (ACTH), prolactin, melatonin, vasopressin, β-endorphin, met-enkephalin, leu-enkephalin, prolactin-releasing factor, prolactin-inhibiting factor, corticotropin-releasing hormone, thyrotropin-releasing hormone (TRH), follicle stimulating hormone (FSH), luteinizing hormone (LH), chorionic gonadotropin (CG), vascular endothelial growth factor (VEGF), angiopoietins, angiostatin, endostatin, granulocyte colony stimulating factor (GCSF), erythropoietin (EPO), connective tissue growth factor (CTGF), basic fibroblast growth factor (bFGF), bFGF2, acidic fibroblast growth factor (aFGF), epidermal growth factor (EGF), transforming growth factor α (TGFα), platelet-derived growth factor (PDGF), insulin-like growth factors I and II (IGF-1 and IGF-II), any one of the transforming growth factor β (TGFβ) superfamily comprising TGFβ, activins, inhibins, or any of the bone morphogenic proteins (BMP) BMPs 1 15, any one of the heregulin/neuregulin/ARIA/neu differentiation factor (NDF) family of growth factors, nerve growth factor (NGF), brain-derived neurotrophic factor (BDNF), neurotrophins NT-3, NT-4/5 and NT-6, ciliary neurotrophic factor (CNTF), glial cell line derived neurotrophic factor (GDNF), neurtuin, persephin, agrin, any one of the family of semaphorins/collapsins, netrin-1 and netrin-2, hepatocyte growth factor (HGF), ephrins, noggin, sonic hedgehog and tyrosine hydroxylase.

Other useful gene products include proteins that regulate the immune system including, without limitation, cytokines and lymphokines such as thrombopoietin (TPO), interleukins (IL) IL-1α, IL-β, IL-2, IL-3, IL-4. IL-5, IL-6, IL-7, IL-8, IL-9, IL-10, IL-11, IL-12, IL-13, IL-14, IL-15, IL-16, and IL-17, monocyte chemoattractant protein (MCP-1), leukemia inhibitory factor (LIF), granulocyte-macrophage colony stimulating factor (GM-CSF), granulocyte colony stimulating factor (G-CSF), monocyte colony stimulating factor (M-CSF), Fas ligand, tumor necrosis factors α and β (TNFα and TNFβ), interferons (IFN) IFN-α, IFN-β, and IFN-γ, stem cell factor, flk-2/flt3 ligand. Gene products produced by the immune system are also encompassed by this invention. These include, without limitations, immunglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered MHC molecules including single chain MHC molecules. Useful gene products also include complement regulatory proteins such as membrane cofactor protein (MCP), decay accelerating factor (DAF), CR1, CR2 and CD59.

Still other useful gene products include any one of the receptors for the hormones, growth factors, cytokines, lymphokines, regulatory proteins and immune system proteins. Examples of such receptors include flt-1, flk-1, TIE-2; the trk family of receptors such as TrkA, MuSK, Eph, PDGF receptor, EGF receptor, HER2, insulin receptor, IGF-1 receptor, the FGF family of receptors, the TGFβ receptors, the interleukin receptors, the interferon receptors, serotonin receptors, α-adrenergic receptors, β-adrenergic receptors, the GDNF receptor, p75 neurotrophin receptor, among others. The invention encompasses receptors for extracellular matrix proteins, such as integrins, counter-receptors for transmembrane-bound proteins, such as intercellular adhesion molecules (ICAM-1, ICAM-2, ICAM-3 and ICAM-4), vascular cell adhesion molecules (VCAM), and selectins E-selectin, P-selectin and L-selectin. The invention encompasses receptors for cholesterol regulation, including the LDL receptor, HDL receptor, VLDL receptor, and the scavenger receptor. The invention encompasses the apolipoprotein ligands for these receptors, including ApoAI, ApoAIV and ApoE. The invention also encompasses gene products such as steroid hormone receptor superfamily including glucocorticoid receptors and estrogen receptors, Vitamin D receptors and other nuclear receptors. In addition, useful gene products include antimicrobial peptides such as defensins and maginins, transcription factors such as jun, fos, max, mad, serum response factor (SRF), AP-1, AP-2, myb, MRG1, CREM, Alx4, FREAC1, NF-κB, members of the leucine zipper family, C₂H₄ zinc finger proteins, including Zif268, EGR1, EGR2, C6 zinc finger proteins, including the glucocorticoid and estrogen receptors, POU domain proteins, exemplified by Pit 1, homeodomain proteins, including HOX-1, basic helix-loop-helix proteins, including myc, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor 1 (IRF-1), Wilms' tumor protein, ETS-binding protein, STAT, GATA-box binding proteins, e.g., GATA-3, and the forkhead family of winged helix proteins.

Other useful gene products include carbamoyl synthetase 1, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, porphobilinogen deaminase, factor Vii, factor VIII, factor IX, factor II, factor V, factor X, factor XII, factor XI, von Willebrand factor, superoxide dismutase, glutathione peroxidase and reductase, heme oxygenase, angiotensin converting enzyme, endothelin-1, atrial natriuretic peptide, pro-urokinase, urokinase, plasminogen activator, heparin cofactor II, activated protein C (Factor V Leiden), Protein C, antithrombin, cystathione beta-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta-glucosidase, pyruvate carboxylase, hepatic phosphorylase, phosphorylase kinase, glycine decarboxylase (also referred to as P-protein), H-protein, T-protein, Menkes disease protein, tumor suppressors (e.g., p53), cystic fibrosis transmembrane regulator (CFTR), the product of Wilson's disease gene PWD, Cu/Zn superoxide dismutase, aromatic amino acid decarboxylase, tyrosine hydroxylase, acetylcholine synthetase, prohormone convertases, protease inhibitors, lactase, lipase, trypsin, gastrointestinal enzymes including chymotrypsin, and pepsin, adenosine deaminase, α1 anti-trypsin, tissue inhibitor of metalloproteinases (TIMP), GLUT-1, GLUT-2, trehalose phosphate synthase, hexokinases I, II and III, glucokinase, any one or more of the individual chains or types of collagen, elastin, fibronectin, thrombospondin, vitronectin and tenascin, and suicide genes such as thymidine kinase and cytosine deaminase. Other useful proteins include those involved in lysosomal storage disorders, including acid β-glucosidase, α-galactosidase a, α-1-iduronidase, iduroate sulfatase, lysosomal acid α-glucosidase, sphingomyelinase, hexosaminidase A, hexomimidases A and B, arylsulfatase A, acid lipase, acid ceramidase, galactosylccramidase, α-fucosidase, α-, β-mannosidosis, aspartylglucosaminidase, neuramidase, galactosylcerami- dase, heparan-N-sulfatase, N-acetyl-α-glucosaminidase, Acetyl-CoA: α-glucosaminide N-acetyltransferase, N-acetylglucosamine-6-sulfate sulfatase, N-acetylgalactosamine-6-sulfate sulfatase, arylsulfatase B, β-glucuoronidase and hexosaminidases A and B.

Other useful transgenes include non-naturally occurring polypeptides, such as chimeric or hybrid polypeptides or polypeptides having a non-naturally occurring amino acid sequence containing insertions, deletions or amino acid substitutions. For example, single-chain engineered immunoglobulins could be useful in certain immunocompromised patients. Other useful proteins include truncated receptors which lack their transmembrane and cytoplasmic domain. These truncated receptors can be used to antagonize the function of their respective ligands by binding to them without concomitant signaling by the receptor. Other types of non-naturally occurring gene sequences include sense and antisense molecules and catalytic nucleic acids, such as ribozymes, which could be used to modulate expression of a gene.

Viral Vectors

Compositions as described herein (e.g., compositions including a viral vector encoding GAA) may be administered to a mammalian subject by any suitable technique. Various techniques using viral vectors for the introduction of a GAA gene into cells are provided for according to the compositions and methods described herein. Viruses are naturally evolved vehicles which efficiently deliver their genes into host cells and therefore are desirable vector systems for the delivery of therapeutic genes. Preferred viral vectors exhibit low toxicity to the host cell and produce therapeutic quantities of GAA protein (e.g., in a tissue-specific manner). Viral vector methods and protocols are reviewed in Kay et al., Nature Medicine, 7:33-40, 2001.

Although the experiments described below involve rAAV, any suitable viral vector can be used. Many viral vectors are known in the art for delivery of genes to mammalian subject and a non-exhaustive list of examples follows. Methods for use of recombinant Adenoviruses as gene therapy vectors are discussed, for example, in W. C. Russell, *J. Gen. Virol.*, 81:2573-2604, 2000; and Bramson et al., *Curr. Opin. Biotechnol.*, 6:590-595, 1995. Methods for use of Herpes Simplex Virus vectors are discussed, for example, in *Cotter and Robertson, Curr. Opin. Mol. Ther.* 1:633-644, 1999. Replication-defective lentiviral vectors, including HIV, may also be used. Methods for use of lentiviral vectors are discussed, for example, in Vigna and Naldini, *J. Gene Med.,* 5:308-316, 2000 and Miyoshi et al., *J. Virol.,* 72:8150-8157, 1998. Retroviral vectors, including Murine Leukemia Virus-based vectors, may also be used. Methods for use of retrovirus-based vectors are discussed, for example, in Hu and Pathak, *Pharmacol. Rev.* 52:493-511, 2000 and Fong et al., *Crit. Rev. Ther. Drug Carrier Syst.*, 17:1-60, 2000. Other viral vectors that may find use include Alphaviruses, including Semliki Forest Virus and Sindbis Virus. Hybrid viral vectors may be used to deliver a gaa gene to a target tissue (e.g., muscle, central nervous system). Standard techniques for the construction of hybrid vectors are well-known to those skilled in the art. Such techniques can be found, for example, in Sambrook et al., In *Molecular Cloning: A Laboratory Manual* (Cold Spring Harbor, N.Y.), or any number of laboratory manuals that discuss recombinant DNA technology.

rAAV Vectors And Virions

In some embodiments, nucleic acids of the compositions and methods described herein are incorporated into rAAV vectors and/or virions in order to facilitate their introduction into a cell. rAAV vectors useful in the invention are recombinant nucleic acid constructs that include (1) a heterologous sequence to be expressed (e.g., a polynucleotide encoding a GAA protein) and (2) viral sequences that facilitate integration and expression of the heterologous genes. The viral sequences may include those sequences of AAV that are required in cis for replication and packaging (e.g., functional ITRs) of the DNA into a virion. In typical applications, the heterologous gene encodes GAA, which is useful for correcting a GAA-deficiency in a cell. Such rAAV vectors may also contain marker or reporter genes. Useful rAAV vectors have one or more of the AAV WT genes deleted in whole or in part, but retain functional flanking ITR sequences. The AAV ITRs may be of any serotype (e.g., derived from serotype 2) suitable for a particular application. Methods for using rAAV vectors are discussed, for example, in Tal. *J.*

Biomed. Sci., 7:279-291, 2000; and Monahan and Samulski, Gene Delivery, 7:24-30, 2000.

The nucleic acids and vectors of the invention are generally incorporated into a rAAV virion in order to facilitate introduction of the nucleic acid or vector into a cell. The capsid proteins of AAV compose the exterior, non-nucleic acid portion of the virion and are encoded by the AAV cap gene. The cap gene encodes three viral coat proteins, VP1, VP2 and VP3, which are required for virion assembly. The construction of rAAV virions has been described. See, e.g., U.S. Pat. Nos. 5,173,414, 5,139,941, 5,863,541, and 5,869,305, 6,057,152, 6,376,237; Rabinowitz et al., *J. Virol.*, 76:791-801, 2002; and Bowles el al., *J. Virol.*, 77:423-432, 2003.

rAAV virions useful in the invention include those derived from a number of AAV serotypes including 1, 2, 3, 4, 5, 6, 7, 8 and 9. For targeting muscle cells, rAAV virions that include at least one serotype 1 capsid protein may be particularly useful as the experiments reported herein show they induce significantly higher cellular expression of GAA than do rAAV virions having only serotype 2 capsids. rAAV virions that include at least one serotype 6 capsid protein may also be useful, as serotype 6 capsid proteins are structurally similar to serotype 1 capsid proteins, and thus are expected to also result in high expression of GAA in muscle cells. rAAV serotype 9 has also been found to be an efficient transducer of muscle cells. Construction and use of AAV vectors and AAV proteins of different serotypes are discussed in Chao et al., *Mol. Ther.* 2:619-623, 2000; Davidson et al., *Proc. Natl. Acad. Sci. USA.* 97:3428-3432, 2000: Xiao et al., *J. Virol.* 72:2224-2232, 1998; Halbert et al., *J. Virol.* 74:1524-1532, 2000; Halbert et al., *J. Virol.* 75:6615-6624, 2001; and Auricchio el al., *Hum. Molec. Genet.,* 10:3075-3081, 2001.

Also useful in the invention are pseudotyped rAAV. Pseudotyped vectors of the invention include AAV vectors of a given serotype (e.g., AAV2) pseudotyped with a capsid gene derived from a serotype other than the given serotype (e.g., AAV1, AAV2, AAV3, AAV4, AAV5, AAV6, AAV7, AAV8, AAV9 etc.). For example, a representative pseudotyped vector of the invention is a rAAV2 vector encoding GAA pseudotyped with a capsid gene derived from AAV of a different serotype (e.g., AAV1, AAV3, AAV4, AAV5, AAV6, AAV7, AAV8, AAV9). In one embodiment, it was observed that LacZ transgene delivery using the IV administration route and rAAV2/9 pseudotype capsid results in approximately 200 fold higher levels of expression in cardiac tissue than an identical dose with rAAV2/1. Additional experiments indicated that IV delivery of a transgene using rAAV2/9 to adult mice also results in transduction of cardiac tissue. Techniques involving the construction and use of pseudotyped rAAV virions are known in the art and are described in Duan et al., *J. Virol.*, 75:7662-7671, 2001; Halbert et al., *J. Virol.*, 74:1524-1532, 2000; Zolotukhin et al., *Methods,* 28:158-167, 2002; and Auricchio et al., *Hum. Molec. Genet.,* 10:3075-3081, 2001.

AAV virions that have mutations within the virion capsid may be used to infect particular cell types more effectively than non-mutated capsid virions. For example, suitable AAV mutants may have ligand insertion mutations for the facilitation of targeting AAV to specific cell types. The construction and characterization of AAV capsid mutants including insertion mutants, alanine screening mutants, and epitope tag mutants is described in Wu et al., *J. Virol.*, 74:8635-45, 2000. Other rAAV virions that can be used in methods of the invention include those capsid hybrids that are generated by molecular breeding of viruses as well as by exon shuffling. See Soong et al., *Nat. Genet.*, 25:436-439, 2000; and Kolman and Stemmer, *Nat. Biotechnol.*, 19:423-428, 2001.

Modulating GAA Levels in a Cell

The nucleic acids, vectors, and virions described above can be used to modulate levels of GAA in a cell. The method includes the step of administering to the cell a composition including a nucleic acid that includes a polynucleotide encoding GAA interposed between two AAV ITRs. The cell can be from any animal into which a nucleic acid of the invention can be administered. Mammalian cells (e.g., human beings, dogs, cats, pigs, sheep, mice, rats, rabbits, cattle, goats, etc.) from a subject with GAA deficiency are typical target cells for use in the invention.

In some embodiments, the cell is a myocardial cell, e.g., a myocardiocyte. In other embodiments, the cell is a neuron (e.g., phrenic motor nerve).

Increasing Motoneuron (e.g., Phrenic Neuron) Function in a Mammal rAAV vectors, compositions and methods described herein can be used to increase phrenic nerve activity in a mammal having Pompe disease and/or insufficient GAA levels. For example, rAAV encoding GAA can be administered to the central nervous system (e.g, neurons). In another example, retrograde transport of a rAAV vector encoding GAA from the diaphragm (or other muscle) to the phrenic nerve or other motor neurons can result in biochemical and physiological correction of Pompe disease. These same principles could be applied to other neurodegenerative disease.

Increasing GAA Activity in a Subject

The nucleic acids, vectors, and virions described above can be used to modulate levels of functional GAA in an animal subject. The method includes the step of providing an animal subject and administering to the animal subject a composition including a nucleic acid that includes a polynucleotide encoding GAA interposed between two AAV ITRs. The subject can be any animal into which a nucleic acid of the invention can be administered. For example, mammals (e.g., human beings, dogs, cats, pigs, sheep, mice, rats, rabbits, cattle, goats, etc.) are suitable subjects. The methods and compositions of the invention are particularly applicable to GAA-deficient animal subjects.

The compositions described above may be administered to animals including human beings in any suitable formulation by any suitable method. For example, rAAV virions (i.e., particles) may be directly introduced into an animal, including by intravenous (IV) injection, intraperitoneal (IP) injection, or in situ injection into target tissue (e.g., muscle). For example, a conventional syringe and needle can be used to inject a rAAV virion suspension into an animal. Depending on the desired route of administration, injection can be in situ (i.e., to a particular tissue or location on a tissue), IM, IV, IP, or by another parenteral route. Parenteral administration of virions by injection can be performed, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the rAAV virions may be in powder form (e.g., lyophilized) for constitution with a suitable vehicle, for example, sterile pyrogen-free water, before use.

To facilitate delivery of the rAAV virions to an animal, the virions of the invention can be mixed with a carrier or excipient. Carriers and excipients that might be used include saline (especially sterilized, pyrogen-free saline) saline buffers (for example, citrate buffer, phosphate buffer, acetate buffer, and bicarbonate buffer), amino acids, urea, alcohols, ascorbic acid, phospholipids, proteins (for example, serum albumin). EDTA, sodium chloride, liposomes, mannitol, sorbitol, and glycerol. USP grade carriers and excipients are particularly useful for delivery of virions to human subjects. Methods for making such formulations are well known and can be found in, for example, *Remington s Pharmaceutical Sciences.*

In addition to the formulations described previously, the virions can also be formulated as a depot preparation. Such long acting formulations may be administered by implantation (for example subcutaneously or intramuscularly) or by IM injection. Thus, for example, the virions may be formulated with suitable polymeric or hydrophobic materials (for example as an emulsion in an acceptable oil) or ion exchange resins, or as sparingly soluble derivatives.

Similarly, rAAV vectors may be administered to an animal subject using a variety of methods. rAAV vectors may be directly introduced into an animal by intraperitoneal administration (IP injection), as well as parenteral administration (e.g., IV injection, IM injection, and in situ injection into target tissue). Methods and formulations for parenteral administration described above for rAAV virions may be used to administer rAAV vectors.

Ex vivo delivery of cells transduced with rAAV virions is also provided for within the invention. Ex vivo gene delivery may be used to transplant rAAV-transduced host cells back into the host. Similarly, ex vivo stem cell (e.g., mesenchymal stem cell) therapy may be used to transplant rAAV vector-transduced host cells back into the host. A suitable ex vivo protocol may include several steps. A segment of target tissue (e.g., muscle, liver tissue) may be harvested from the host and rAAV virions may be used to transduce a GAA-encoding nucleic acid into the host's cells. These genetically modified cells may then be transplanted back into the host. Several approaches may be used for the reintroduction of cells into the host, including intravenous injection, intraperitoneal injection, or in situ injection into target tissue. Microencapsulation of cells transduced or infected with rAAV modified ex vivo is another technique that may be used within the invention. Autologous and allogeneic cell transplantation may be used according to the invention.

Effective Doses

The compositions described above are typically administered to a mammal in an effective amount, that is, an amount capable of producing a desirable result in a treated subject (e.g., increasing WT GAA activity in the subject). Such a therapeutically effective amount can be determined as described below.

Toxicity and therapeutic efficacy of the compositions utilized in methods of the invention can be determined by standard pharmaceutical procedures, using either cells in culture or experimental animals to determine the $LD_{50}$ (the dose lethal to 50% of the population). The dose ratio between toxic and therapeutic effects is the therapeutic index and it can be expressed as the ratio $LD_{50}/ED_{50}$. Those compositions that exhibit large therapeutic indices are preferred. While those that exhibit toxic side effects may be used, care should be taken to design a delivery system that minimizes the potential damage of such side effects. The dosage of compositions as described herein lies generally within a range that includes an $ED_{50}$ with little or no toxicity. The dosage may vary within this range depending upon the dosage form employed and the route of administration utilized.

As is well known in the medical and veterinary arts, dosage for any one animal depends on many factors, including the subject's size, body surface area, age, the particular composition to be administered, time and route of administration, general health, and other drugs being administered concurrently. It is expected that an appropriate dosage for intravenous administration of particles would be in the range of about $10^{12}$-$10^{15}$ particles. For a 70-kg human, a 1- to 10-mL (e.g., 5 mL) injection of $10^{12}$-$10^{15}$ particles is presently believed to be an appropriate dose.

Embodiments of inventive compositions and methods are illustrated in the following examples. These examples are provided for illustrative purposes and are not considered limitations on the scope of inventive compositions and methods.

EXAMPLES

Materials and Methods

Virus Production

Recombinant AAV vectors were generated, purified, and titered at the University of Florida Powell Gene Therapy Center Vector Core Laboratory as previously described (Zolotukhin, S, et al., *Methods.* 28:158-167, 2002).

Intravenous Injections

All animal procedures were performed in accordance with the University of Florida Institutional Animal Care and Use Committee (IACUC) guidelines (mice) or the University of California (UC) Davis IACUC (monkeys; see below). One-day-old mouse pups were injected via the superficial temporal vein as previously described (Sands M S, et al., *Lab. Anim. Sci.,* 49:328-330, 1999). Briefly, mice were anesthetized by induced hypothermia. A 29.5-gauge tuberculin syringe was used to deliver vector in a total volume of 35 µL directly into the left temporal vein. Two-month-old adult mice were injected via the jugular vein. Mice were first anesthetized using a mixture of 1.5% isoflurane and $O_2$ (1 to 2 L). A 0.5-cm incision was made to expose the jugular vein. A 29-gauge sterile needle and syringe were then used to deliver virus in a volume of 150 µL. Hemostasis was obtained; the skin was approximated and held secure with Vetbond (3M, St. Paul, Minn.).

β-Galactosidase Detection

Tissue lysates were assayed for β-galactosidase enzyme activity using the Galacto-Star chemiluminescence reporter gene assay system (Tropix Inc, Bedford, Mass.). Protein concentrations for tissue lysates were determined using the Bio-Rad DC protein assay kit (Hercules, Calif.).

ECG Analysis

ECG tracings were acquired using standard subcutaneous needle electrodes (MLA1203, 1.5 mm Pin 5; AD Instruments) in the right shoulder, right forelimb, left forelimb, left hindlimb, and tail and a Power Laboratory Dual BioAmp instrument. Five minutes of ECG tracings from each animal were analyzed using ADInstrument's Chart® software.

Nonhuman Primate Studies

Studies with monkeys were conducted in the Center for Fetal Monkey Gene Transfer for Heart, Lung, and Blood Diseases located at the California National Primate Research Center (UC Davis). Gravid rhesus monkeys (n=6) were monitored during pregnancy by ultrasound, and newborns delivered by cesarean section at term using established techniques. Within an hour of birth, newborns were injected intravenous with vector (=1 mL) via a peripheral vessel. Infants received either rAAV2/1-CMV-hGaa (n=3) or rAAV2/9-CMV-hGaa (n=3). Infants were nursery reared and monitored for 6 months and then euthanized by an overdose of pentobarbital and complete tissue harvests performed (one per group) using established methods. Specimens from control animals of a comparable age were made available through the Center for Fetal Monkey Gene Transfer. GAA activity was measured from tissues harvested 6 months postinjection and background activity from non-injected controls was subtracted to yield the results in FIG. 5A. Genomic DNA (gDNA) was extracted from tissues according to the protocol of the manufacturer (Qiagen; DNeasy tissue kit). Resulting DNA concentrations from the extraction procedure were determined using an Eppendorf Biophotometer (Model 6131; Eppendorf, Hamburg, Germany). One microgram of extracted gDNA was used in all quantitative PCRs according to a previously used protocol (Song, S, et al., *Mol Ther.*, 6:329-335, 2002) and reaction conditions (recommended by Perkin-Elmer/Applied Biosystems) included 50 cycles of 94.8° C. for 40 seconds, 37.8° C. for 2 minutes, 55.8° C. for 4 minutes, and 68.8° C. for 30 seconds. Primer pairs were designed to the CMV promoter as described (Donsante A, et al., *Gene Ther.*, 8:1343-1346, 2001) and standard curves established by spike-in concentrations of a plasmid DNA containing the same promoter. DNA samples were assayed in triplicate. The third replicate was supplemented with CBATDNA at a ratio of 100 copies/µg of gDNA. If at least 40 copies of the spike-in DNA were detected, the DNA sample was considered acceptable for reporting vector DNA copies.

Example 1

Figure 1B:
Figure 1C:
Figure 1D:
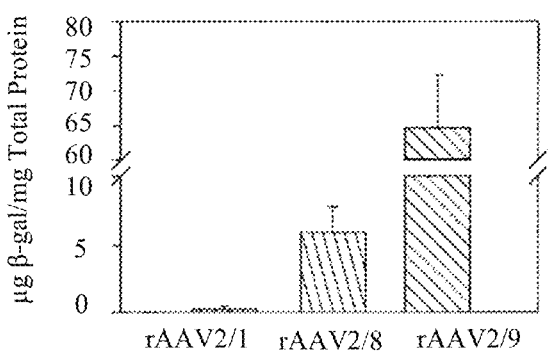
FIG. 1D is a graph showing that intravenous delivery of rAAV2/9 results in high-level transduction of the heart. One-day-old C57BL6/129SvJ mouse neonates (n=5) were injected with $1 \times 10^{11}$ vg of rAAV pseudotypes AAV2/1, AAV2/8, and AAV2/9 carrying the CMV-lacZ construct via the previously described temporal vein delivery route. At 4-weeks postinjection, the β-galactosidase enzyme detection assay was performed to quantify lacZ expression levels.

Recombinant Adeno-Associated Virus Leads to Preferential Cardiac Transduction In Vivo rAAV2/1 was directly compared with two less-characterized serotypes (rAAV2/8 and rAAV2/9) in their abilities to transduce myocardium in vivo. These recombinant or pseudotyped vectors are created by inserting a transgene of interest flanked by the inverted terminal repeats (ITRs) of AAV2 into the capsid of another serotype. $1 \times 10^{11}$ vector genomes (vg) were delivered of each of 3 different serotypes (rAAV2/1, rAAV2/8, or rAAV2/9) carrying the CMV-lacZ construct (cytoplasmic lacZ) by the systemic venous route to 1-day-old mice (5 neonates per group) in an injection volume of 35 µL (FIG. 1A-FIG. 1D). Hearts from the injected mice were harvested at 4 weeks postinjection and 5-bromo-4-chloro-3-indolyl-β-D-galactoside (X-gal) staining was performed on frozen cryosections to visualize the extent of β-galactosidase expression biodistribution across the myocardium (FIG. 1A-FIG. 1C). In addition, β-galactosidase activity was determined to quantify LacZ expression (FIG. 1D). The SYBR green quantitative PCR technique was also performed on these hearts to compare the relative amounts of vector genomes present. It was found that 0.19, 16.12, and 76.95 vg per diploid cell were present in the hearts of mice injected with rAAV2/1, rAAV2/8, and rAAV2/9, respectively.

Calculations for vector genomes per cell were determined as previously described (Wei J F, et al., *Gene Ther.*, 1:261-268, 1994).

The results show that of those serotypes compared in this work, systemic venous delivery of AAV2/9 results in broad and even distribution of vector and transgene product in the myocardium without selective cardiac administration. The level of gene expression was shown to result in a 200-fold greater level of expression than that observed for rAAV2/1. rAAV2/8 provides exceptional transduction of myocardium at levels≈20-fold greater than those obtained using rAAV2/1; however, there is also significant transduction of hepatocytes with this serotype. X-Gal-stained cryosections demonstrated that both rAAV2/8 and rAAV2/9 provide a broad and even distribution of transgene expression throughout the entire heart. In contrast, those hearts injected with rAAV2/1 showed far less overall expression. Additionally, immunohistochemistry with a cardiac troponin antibody (Santa Cruz Biotechnology) was performed and it was found that the cells expressing β-galactosidase were cardiomyocytes.

Figure 2A:
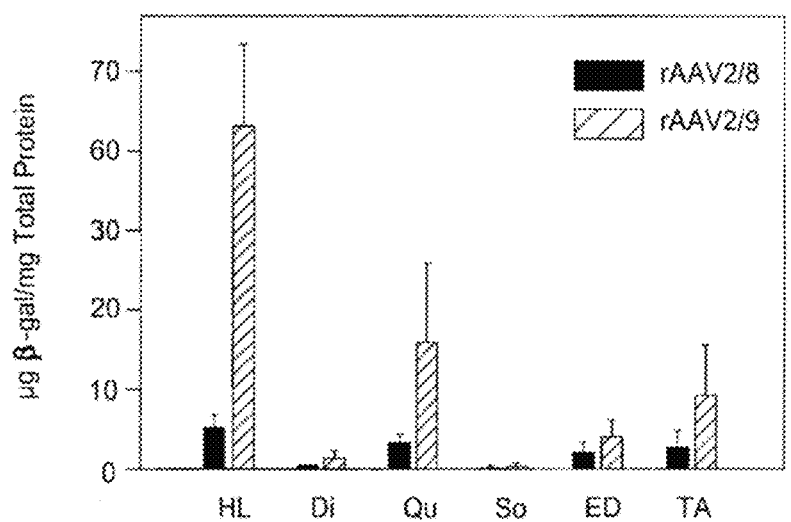
FIG. 2A and FIG. 2B are graphs showing expression biodistribution analysis of β-galactosidase enzyme levels detected in various specimens following delivery of the rAAV2/8-CMV-lacZ or rAAV2/9-CMV-lacZ constructs.

Also, studies demonstrated that rAAV2/9 transduced cardiomyocytes more efficiently than myoblasts in vitro. The β-galactosidase enzyme detection assay was then performed on other tissues from these same animals to characterize the biodistribution of lacZ expression. It was found that rAAV2/8 and rAAV2/9 are both capable of transduction of skeletal muscle to some degree (FIG. 2A). In general, rAAV2/8 has the ability to provide an overall broad and even biodistribution of expression across muscle in addition to the heart, whereas rAAV2/9-delivered transgene expression is far greater in the heart than any other tissue.

Figure 2B:
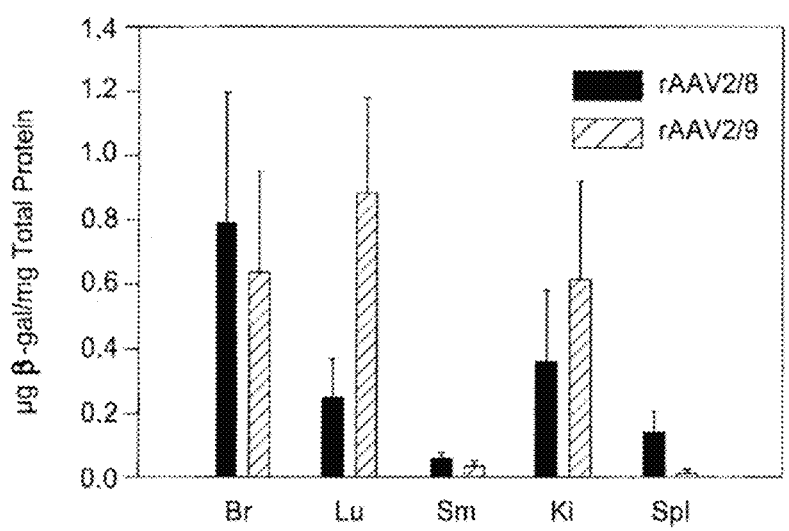

The β-galactosidase assay was also performed on non-cardiac, nonskeletal muscle tissue samples from these mice (FIG. 2B). These results showed that whereas rAAV2/8 and rAAV2/9 are able to transduce tissues such as brain, lung and kidney, there is less transduction of spleen and small intestine.

Once it was established that rAAV2/9 displayed the highest natural affinity for myocardium, rAAV2/9 activity was further characterized in vivo. The CMV promoter was chosen for these studies because this expression cassette was appropriate in size and expression profile in the target tissue of interest. SYBR green quantitative PCR was performed on heart, liver, and quadriceps tissue specimens from mice that were injected with rAAV2/9 to compare the relative amounts of vector genomes present in these tissues. These results showed that there were≈76.95 vg/cell (vector genomes per diploid cell) in myocardium and 2.89 vg/cell and 11.47 vg/cell present in liver and quadriceps, respectively. The clinical implication of these findings is that even when using an AAV capsid, which displays a high natural affinity for a specific tissue, the use of a tissue-specific promoter will be critical to ultimately ensure restricted transgene expression to the area of interest.

Figure 3A:
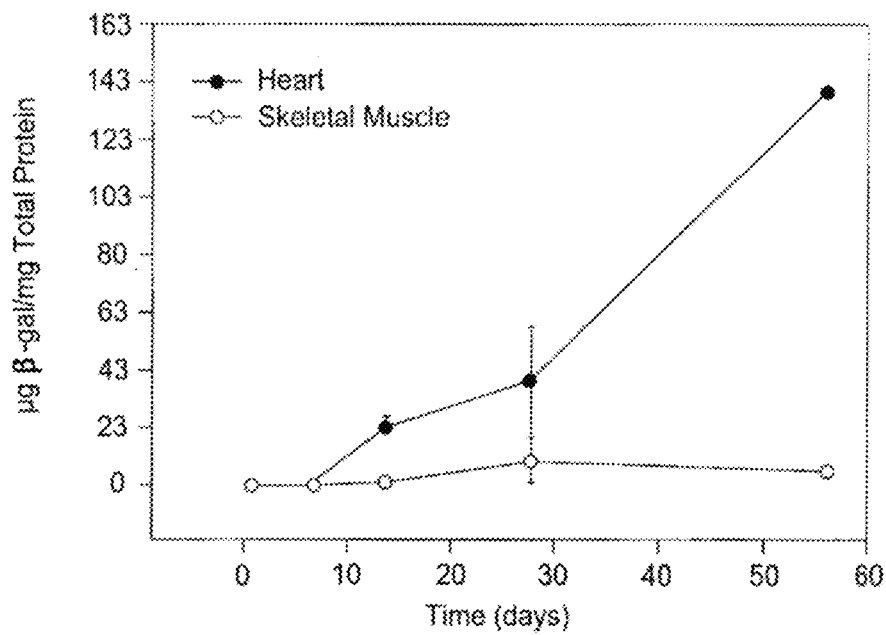
FIG. 3A, FIG. 3B and FIG. 3C are graphs showing a time-course assay following rAAV2/9-mediated delivery of CMV-lacZ.

Additional studies were performed to evaluate a time course assay of rAAV2/9-CMV-lacZ expression in cardiac and skeletal muscle. One-day-old mouse neonates were injected with $5 \times 10^{10}$ vg, and cardiac and skeletal muscles were harvested at 1, 7, 14, 28, and 56 days postinjection (FIG. 3A). The results show that the onset of transgene expression in both tissues occurred between 1 and 7 days following administration of vector. The amount of expression in skeletal muscle increased gradually over the first 28 days, then leveled off and sustained a constant level out to at least 56 days. The amount of transgene expression in cardiac tissue was consistently higher than that in skeletal muscle and continued to steadily increase throughout the duration of the experiment (56 days).

Figure 3B:
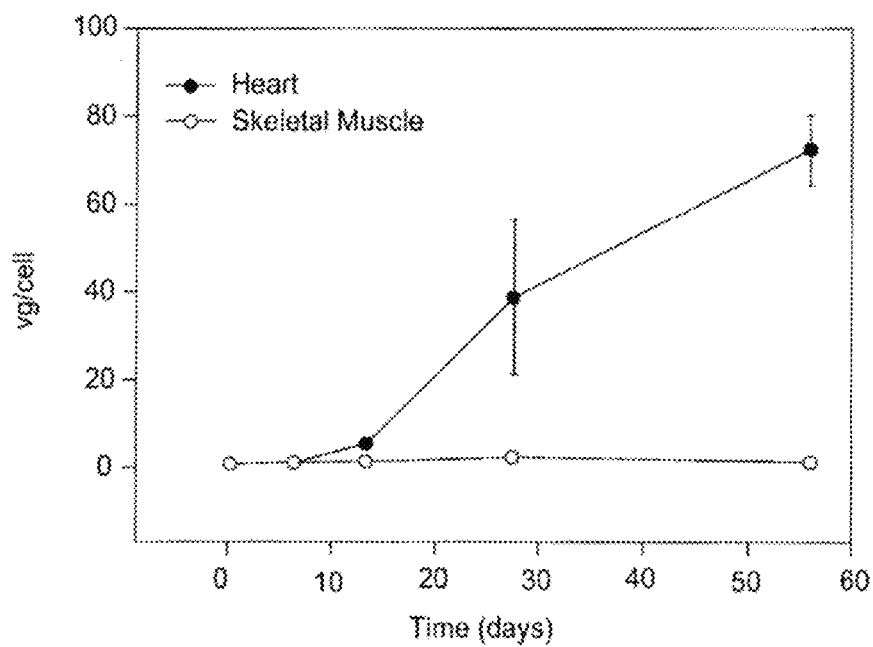
Figure 3C:
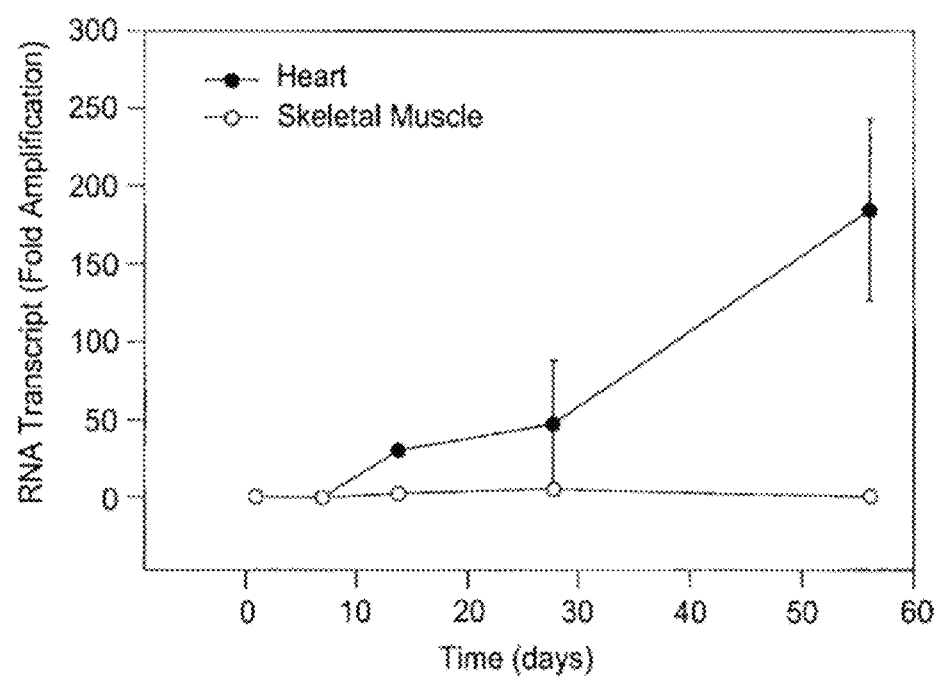

SYBR green quantitative PCR was next performed on these tissues to determine whether the increase of transgene expression in cardiac tissue was attributable to an increase in β-galactosidase protein stability in cardiac tissue as compared with skeletal muscle tissue (FIG. 3B). Vector genome copy number increased in cardiac tissue but not skeletal muscle tissue. Additionally, RNA was isolated from these tissues and it was found that RNA transcript numbers also increased over the duration of the experiment (FIG. 3C).

The cellular receptor for AAV9 is not currently known; however, the preferential cardiac transduction warrants further evaluation of cardiac ligands, which are bound by AAV. The data suggest that the AAV9 capsid may not be absorbed by other tissues as easily as previously studied serotypes because of its inability to bind to a more ubiquitous receptor located throughout the body, such as the heparin sulfate proteoglycan receptor. Therefore the AAV9 capsid could require more time to reach cardiac tissue. An additional explanation for the increase in vector genome concentration over the course of the experiment is that there may be a delay in the double-strand synthesis of the delivered transgene in the heart that could potentially account for a doubling of vector genomes.

Figure 4A:
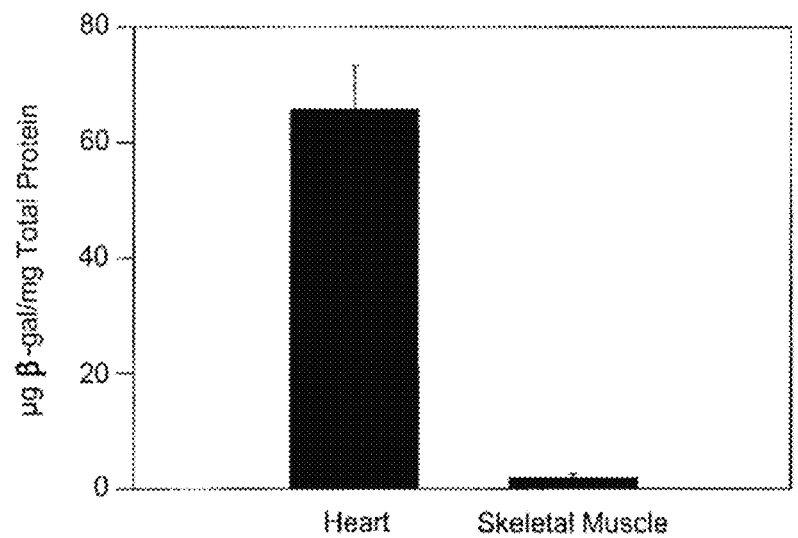
FIG. 4A is a graph showing β-galactosidase expression level analysis of heart and skeletal muscle (4-weeks' post-administration) from mice that were injected with $1\times10^{11}$ vg of rAAV2/9-CMV-lacZ as 1-day old neonates.
Figure 4B:
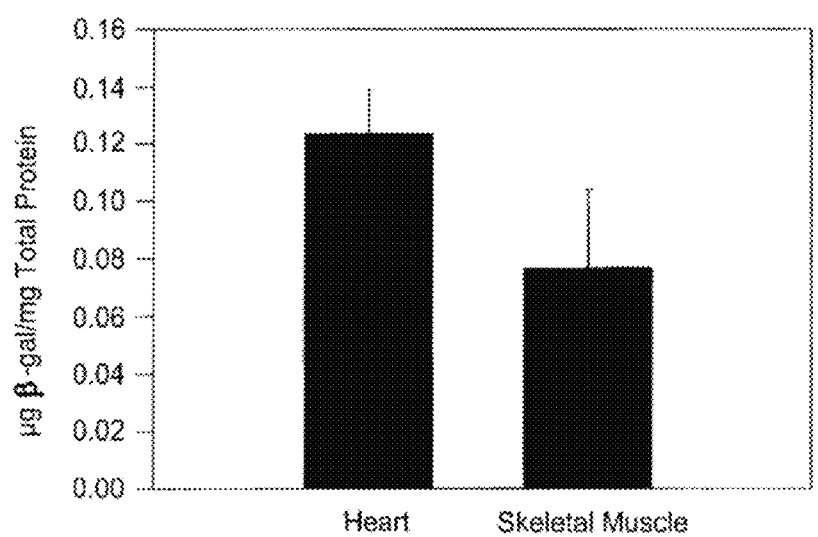
FIG. 4B is a graph showing β-galactosidase expression level analysis of heart and skeletal muscle (4 weeks' post-administration) from mice that were injected with $1\times10^{11}$ vg of rAAV2/9-CMV-lacZ via the jugular vein at 3 months of age (n=3).

Next, a study in adult mice was performed to determine whether the rAAV2/9 behavior that was observed in neonates is similar in adult animals. rAAV2/9-CMV-lacZ ($1 \times 10^{11}$ vg) was administered to 3-month-old mice using an intravenous delivery route via the jugular vein (FIG. 4B). Tissues were harvested at 4 weeks postinjection, and the level of transgene expression was determined for both cardiac and skeletal muscle. The results show that rAAV2/9 does transduce cardiac and skeletal muscle in adult mice, although in comparison with the same dose administered to neonates, the expression levels were far lower (FIG. 4A). The rAAV2/9-delivered expression level in adults was comparable to that observed following intravenous delivery of the same dose of rAAV2/1-CMV-lacZ to neonates. Lower overall rAAV2/9 transduction in adults in comparison to the same dose in neonates is not unexpected because of the reduced dose per kilogram of body weight. These data demonstrate, however, that a similar biodistribution profile is observed whether rAAV2/9 is intravenously delivered to adults or neonates and provide further evidence that rAAV2/9 preferentially transduces cardiac tissue.

A model of inherited cardiomyopathy was used to assess a gene-transfer approach to this condition. Pompe disease is a form of muscular dystrophy and metabolic myopathy caused by mutations in the acid β-glucosidase (Gaa) gene. An insufficient amount of the GAA enzyme leads to the accumulation of glycogen in lysosomes and consequent cellular dysfunction. In human patients, there is a direct correlation between the amount of GAA produced and the severity of disease. Without treatment, cardiorespiratory failure typically occurs in the early-onset patients within the first year of life.

To demonstrate the ability of the rAAV2/9 pseudotype to deliver a therapeutic transgene to correct and/or prevent the onset of a disease phenotype, the $Gaa^{-/-}$ mouse model was treated with rAAV2/9-CMV-hGaa (human Gaa). Because of the rAAV2/9 marker gene results, it was anticipated that a lower therapeutic dose than is typically necessary would be sufficient to provide correction in a mouse model of cardiomyopathy. Therefore, doses per neonate of either $4 \times 10^5$ or $4 \times 10^8$ vg of rAAV2/9-CMV-hGaa were administered to $Gaa^{-/-}$ mice at 1 day of age using the intravenous delivery route. At 3 months postinjection, ECGs were performed on each dosage group of treated mice and noninjected, age matched $Gaa^{-/-}$ and healthy wild-type (B6/129) controls.

Similar to the human form of this disease, untreated $Gaa^{-/-}$ mouse ECGs display a shortened PR interval as compared with healthy B6/129 controls (PR=33.41±1.35 ms, or 26% shorter than wild type [PR=44.95±1.58 ms]). The mice that were treated with the low dose ($4 \times 10$ vg) of rAAV2/9-CMV-hGaa displayed a PR interval of 36.76±1.12 ms, or only 18% shorter than wild-type, age-matched controls (P=0.062). The dosage group treated with $4 \times 10^8$ vg displayed a PR interval of 39.38±2.42 ms, or only 12% shorter than B6/129 age-matched controls (P=0.058). Essentially, at these low doses, a lengthened PR interval was observed that may increase as time progresses.

Figure 5A:
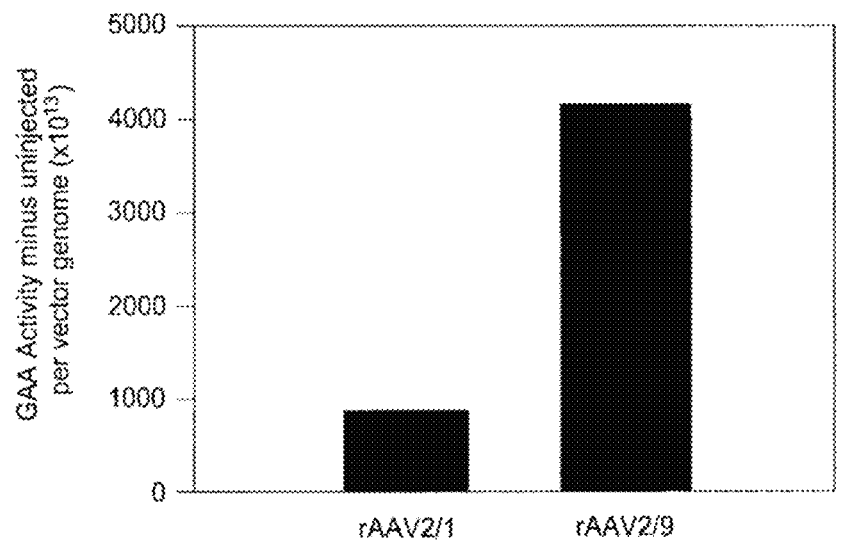
FIG. 5A is a graph showing GAA activity in tissue specimens from the hearts of rhesus macaques intravenously injected at birth with either rAAV2/1-CMV-hGaa or rAAV2/9-CMV-hGaa. Y-axis shows total GAA activity minus background activity from noninjected controls per vector genome delivered.
Figure 5B:
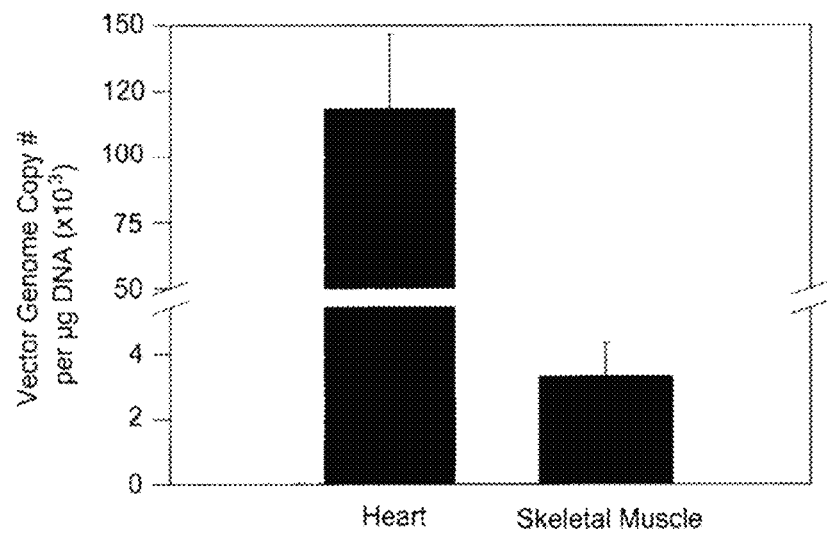
FIG. 5B is a graph demonstrating the vector genome biodistribution profile between heart and skeletal muscle tissue from rhesus macaque intravenously injected at birth with rAAV2/9-CMV-hGaa. All data are at 6 months' post-vector administration.

Although the mouse is a generally well-accepted model for gene therapy studies, behavior of the various AAV capsids in humans may be quite different. Therefore, long-term experiments are presently being performed in nonhuman primates to assess the expression over time in an animal model more phylogenetically similar to humans. Results from this ongoing study show that at 6 months following intravenous delivery via a peripheral vessel (at birth) of rAAV2/9-CMV-hGaa or rAAV2/1-CMV-hGaa to infant rhesus macaques, the expression profile between serotypes is similar to what was observed in mice with rAAV2/9, providing≈4-fold more GAA expression than rAAV2/1 (FIG. 5A). The vector genome biodistribution profile observed in these nonhuman primate tissues was also similar to what was found in mouse tissue (FIG. 5B) with rAAV2/9, demonstrating a dramatic preference for cardiac tissue over skeletal muscle. For both the expression and vector genome analysis of nonhuman primate heart specimens, numbers were averaged between right and left heart including the atria and ventricles. Biodistribution of expression and vector genomes appeared to be even throughout the heart.

Example 2

The AAV9 Capsid Preferentially Transduces Cardiac Tissue and Demonstrates Unique Behavior In Vivo Development of a Gene Therapy Approach for the Treatment of Inherited Cardiomyopathies:

By assessing expression profiles in tissues throughout the body following intravenous (IV) administration of virus to adults, newborn mice and non-human primates, it was determined that (of those assessed) the optimal AAV serotype for transduction of cardiac tissue is AAV2/9. Through MRI, ECG and tissue analysis, it was demonstrated that IV delivery of $4^{10}$ vg AAV2/9 carrying a therapeutic transgene can ameliorate the cardiac phenotype in a mouse model of Pompe disease, a glycogen storage disorder. At 3 month of age ECG analysis showed improvement in PR interval and MRI assessment demonstrated increased cardiac output as compared to untreated controls At 6 months post administration these improvements continued and PAS stains of heart specimens showed successful clearance of glycogen. The high natural affinity of AAV2/9 for cardiac tissue suggests that it preferentially binds a receptor that is prevalent in cardiomyocytes. The studies have unveiled an interesting feature that is unique to this capsid among those previously worked with. $5^{10}$ vg of AAV2/9-CMV-LacZ were administered to 1 day old mice and heart and muscles were harvested in a time course out to 56 days to quantify expression. While beta-gal expression leveled off in skeletal muscle tissue, it continued to increase in heart. Analysis of vg revealed the same phenomenon. The data suggests that AAV9 capsids may continue to be released from tissues over time and require more time to reach the heart following IV delivery.

rAAV2/9 Mediated Gene Delivery of Acid α-Glucosidase Corrects the Cardiac Phenotype in a Mouse Model of Pompe Disease:

Pompe Disease is a form of muscular dystrophy and metabolic myopathy caused by mutations in the acid alpha glucosidase (GAA) gene. An insufficient amount of GAA leads to the accumulation of glycogen in lysosomes and consequent cellular dysfunction. In human patients there is a direct correlation between the amount of GAA produced and severity of disease. Without treatment, cardio-respiratory failure typically occurs in the early onset patients within the first year of life.

Described herein is a characterization study of the cardiac phenotype in the GAA knockout mouse model (gaa–/–) at various ages through analysis of ECG traces, MRI data and use of the periodic acid shift (PAS) stain to visually assess glycogen content in tissue sections. Through ECG analysis, a shortened PR interval was observed by 3 months of age (gaa–/– 33.41±1.35 ms, control 44.95±1.58 ms) mimicking the conduction phenotype observed in the human Pompe population. By 2 weeks of age abnormal amounts of glycogen can be observed in the lysosomes of cardiac cells as demonstrated by the PAS stain. MRI analysis shows a decrease in stroke volume (SV) (gaa–/–36.13±1.19 µL, control 51.84±3.59 µL) and a decrease in cardiac output (CO) (gaa–/– 7.95±0.26 mL/min, control 11.40±0.79 mL/min) at 3 months and a significant increase in myocardial mass (gaa–/– 181.99±10.7 mg, control 140.79±5.12 mg) by 12 months of age.

This model of cardiac dysfunction is used in order to develop a cardiac gene delivery technique which can be applied to many genetically inherited cardiomyopathies. It was previously shown that IV delivery of recombinant AAV2 viral vectors pseudotyped with viral capsids of serotype 1 (rAAV2/1) carrying the CMV-hGAA construct to 1 day old Gaa$^{-/-}$ neonates restores GAA activity in various tissues when observed 12 months post-administration. More recently, it was found that LacZ transgene delivery using the IV administration route and rAAV2/9 pseudotype capsid results in approximately 200 fold higher levels of expression in cardiac tissue than an identical dose with rAAV2/1. Additional experiments indicated that IV delivery of a transgene using rAAV29 to adult mice also results in transduction of cardiac tissue.

The most optimal rAAV serotype for cardiac transduction (rAAV2/9) has now been combined with the clinically relevant IV administration route in order to deliver the human GAA (hGAA) gene to Gaa$^{-/-}$ mice. Neonates treated with rAAV2/9-CMV-hGAA at a range of doses ($4\times10^5$ vg, $4\times10^5$ vg and $4\times10^{10}$ vg) using this strategy have demonstrated sustained correction as assessed by ECG analysis (39.38±2.42 ms). PAS stains on frozen tissue sections as well as NMR analysis on lyophilized tissues have shown less glycogen accumulation in cardiac tissue of gaa–/– mice treated as neonates as compared to untreated controls. Non-invasive MRI analysis has shown an increase in SV and CO. Adult Gaa$^{-/-}$ mice have also been treated using the IV delivery route and are currently being assessed in order to reverse the effects of Pompe Disease in mice which have already begun presenting the cardiac phenotype.

The systemic delivery route, use of the CMV promoter and the fact that GAA is a secreted enzyme all promote expression and correction throughout the body. GAA activity has been observed in various other tissues of treated mice including skeletal muscles and liver. In conclusion, these studies have demonstrated the ability of rAAV2/9 to be administered systemically using a relatively noninvasive IV delivery route, transcend the vasculature, transduce tissues throughout the body and ultimately prevent presentation of the cardiac phenotypes of Pompe Disease.

Example 3

MRI for Characterization and Gene Therapy Evaluation in Murine Models of Muscular Dystrophy Studies to establish which combination of adeno-associated virus (AAV) serotype, promoter and delivery route is the most advantageous for cardiac gene delivery are performed. Studies to non-invasively characterize hearts in mouse models of the various forms of muscular dystrophy which can be treated are performed. Examples of models of various forms of muscular dystrophy include: a model for Limb Girdle Muscular Dystrophy; alpha-sarcoglycan knockout (ASG–/–), a model for Myotonic Dystrophy Type 1 (MDNL1–/–) in which exon 3 of MBNL has been deleted and the MDX mouse model for Duchenne Muscular Dystrophy which lacks dystrophin.

In initial characterization studies, cardiac tissue from these models was harvested at a range of ages and found that the manifestations of disease increase with age in all cases. The location and size of dystrophic lesions in the early stages of development can be identified and determined because of their ability to uptake and sequester the fluorescent dye, Evans Blue Dye (EBD), due to the abnormal permeability of deteriorated muscle tissue. The ability to non-invasively identify and monitor the progression of dystrophic lesion development in skeletal muscle using $^1$H-magnetic resonance techniques was also demonstrated. In order to recognize lesions in the later stages of development on cryosections, the trichrome stain was utilized. This stains for the presence of collagen that infiltrates more progressed dystrophic lesions as they undergo fibrosis.

Cardiac MR provides high-resolution images that offer structural as well as global and regional functional information. In older MDX mice (6-52 wk), the heart shows focal lesions of inflammatory cell infiltration, myocyte damage and fibrosis generally located in the ventricle or septum. It was also found that the older MDX hearts (>48 wks) display regions of increased MR signal intensity. The hyper intense regions correlated with regions of myocyte damage, as determined histologically using EBD accumulation, H & E, and trichrome staining. Cardiac MR can also be used to monitor myocyte function. By performing cardiac MRI on these models at various ages, images were obtained which have enabled the identification of the presentation of dilated cardiomyopathy, contractility defects and arrhythmias. In addition to standard cardiac imaging measurements and techniques, cardiac tagging protocols are being established to allow the identification of areas of localized contractility defects. This may be beneficial for mouse models which may display regional dysfunction due to areas of necrotic tissue throughout the heart.

Upon completion of these characterization studies, a next step includes providing gene therapy to these mice and prevention of the manifestations of these diseases. The treated animals are then periodically non-invasively assessed using established MRI protocols in order to ultimately demonstrate functional correction in murine models of cardiomyopathy.

Example 4

Neural Deficits Contribute to Respiratory Insufficiency to Pompe Disease

The main objectives were to determine if GAA$^{-/-}$ mice have an altered pattern of breathing, similar to the ventilation difficulties observed in the patient population and whether ventilation deficits in GSD II are mediated by a central component.

Plethysmography:

Barometric plethysmography was used to measure minute ventilation (MV) and inspiratory time ($T_1$) in GAA$^{-/-}$ mice and age-matched controls (B6/129 strain). After an acclimation period (30 min) and baseline (60 min; $F_iO_2$=21%, $F_iCO_2$=0%), mice were exposed to hypercapnic challenge (10 min, $F_iCO_2$=6.5%) to stimulate respiratory motor output.

Blood Sampling:

Control (B6/129) and GAA-/- mice were anesthetized and ~100 μL tail blood collected into a disposable G8+ cartridge and read with a portable 1-Stat machine (Heska Corp.).

Glycogen Detection:

Glycogen was quantified using a modification of the acid-hydrolysis method. Periodic Acid Schiff stain was performed for histological glycogen detection; Fluoro-Gold® (4%) was painted onto mouse diaphragms 48 hours prior to sacrifice for detection of phrenic motoneurons.

Force Frequency Measurements In Vitro:

The optimal length for isometric tetanic tension was determined for each diaphragm strip followed by progressively increasing stimulation frequency. Force generated was normalized to diaphragm strip length and weight.

Neurophysiology:

The right phrenic nerve was isolated and electrical activity recorded in anesthetized (urethane, i.v. 1.0-1.6 g/kg), mechanically ventilated, paralyzed and vagotomized mice with a bipolar tungsten electrode.

Figure 6A:
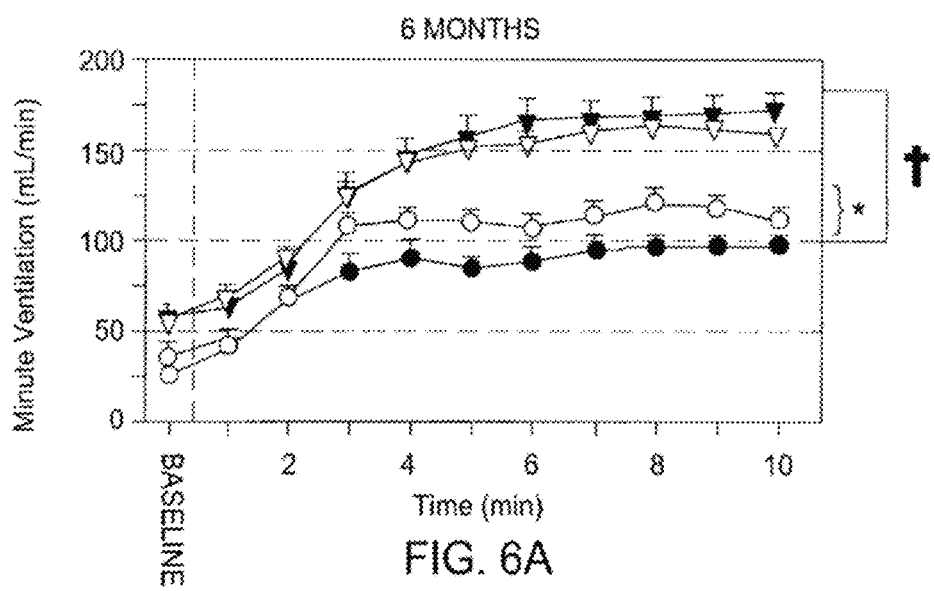
FIG. 6A, FIG. 6B and FIG. 6C are graphs showing the results of minute ventilation (mL/min) at baseline and during 10 minutes of hypercapnia in 6 month (FIG. 6A), 12 month (FIG. 6B) and >21 month (FIG. 6C) control and $GAA^{-/-}$ mice. MEAN±SEM; *=$GAA^{-/-}$ different from control, †=male different from female.
Figure 6B:
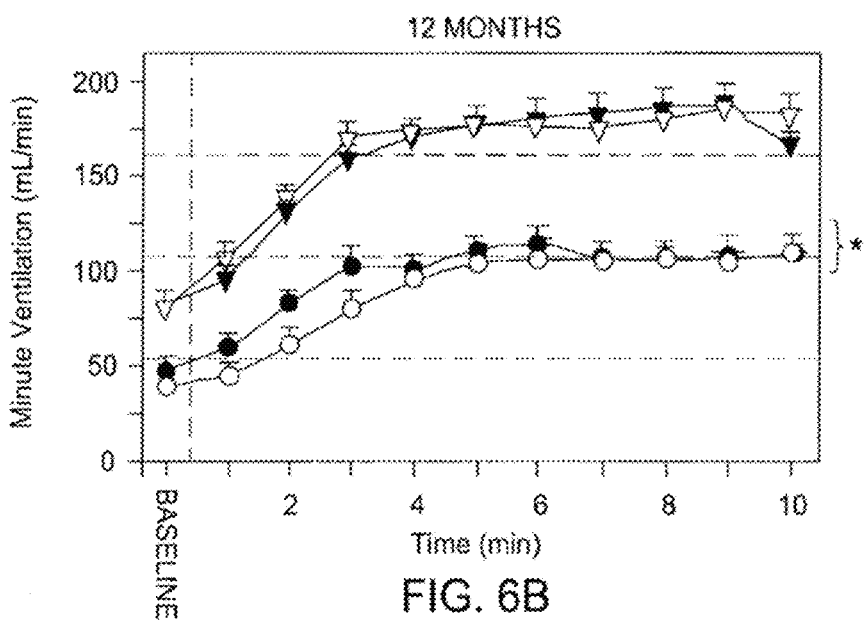
Figure 6C:
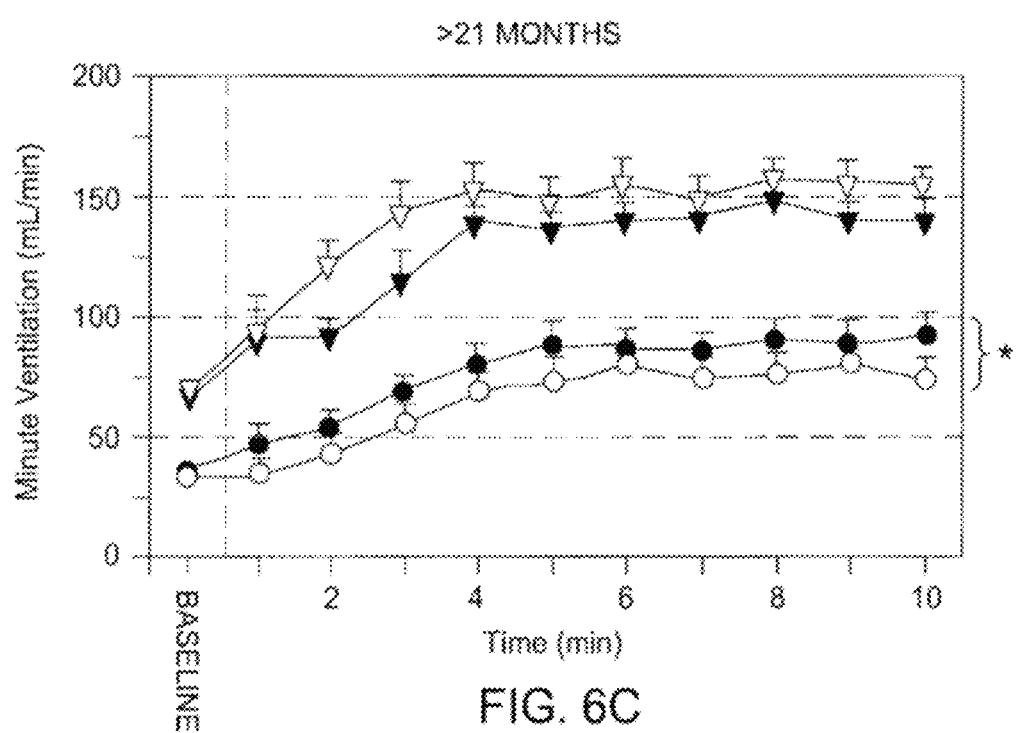

Results and Summary:

FIG. 6A-FIG. 6C are graphs showing the results of minute ventilation (mL/min) at baseline and during 10 minutes of hypercapnia in 6 month (FIG. 6A), 12 month (FIG. 6B) and >21 month (FIG. 6C) control and GAA$^{-/-}$ mice.

Figure 7A:
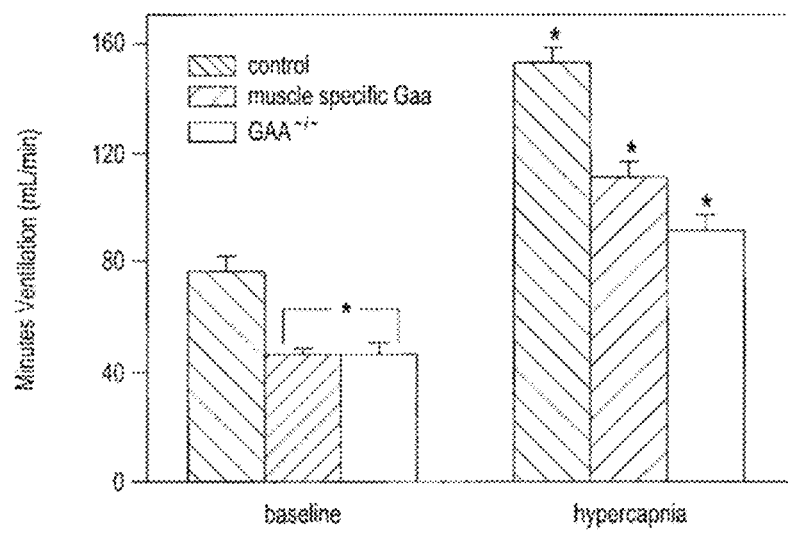
FIG. 7A is a graph showing the results from minute ventilation at baseline and the mean response to hypercapnia in control, $GAA^{-/-}$ and muscle specific GAA mice. Muscle specific GAA mice are maintained on the $GAA^{-/-}$ background, but express GAA only in skeletal muscle.

In summary, the results show: GAA$^{-/-}$ mice have an altered pattern of breathing compared to age matched control mice (FIG. 7A).

Figure 7B:
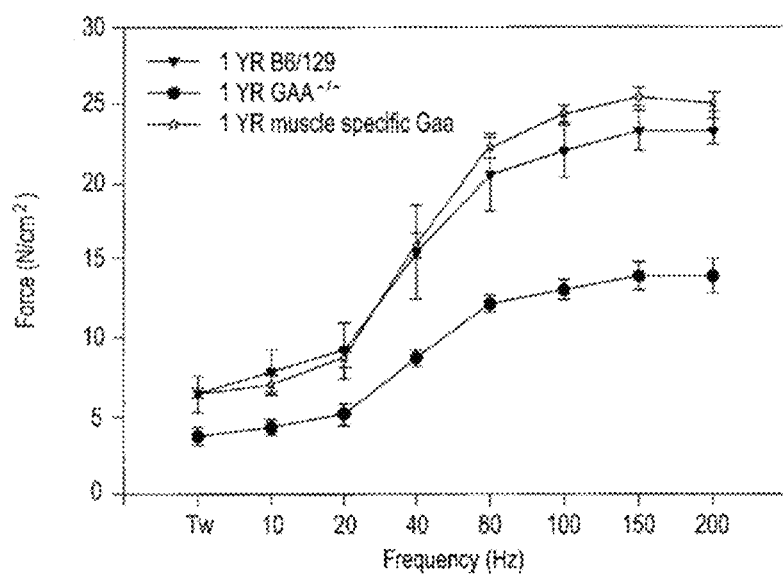
FIG. 7B is a graph showing the results of diaphragmatic contractile function for control, $GAA^{-/-}$ and muscle specific GAA mouse diaphragm at 12 months of age.

GAA deficiency in the nervous system results in ventilation deficits as demonstrated by attenuated minute ventilation in muscle specific GAA mice (which have normal functioning diaphragm) (FIG. 7B).

Figure 8:
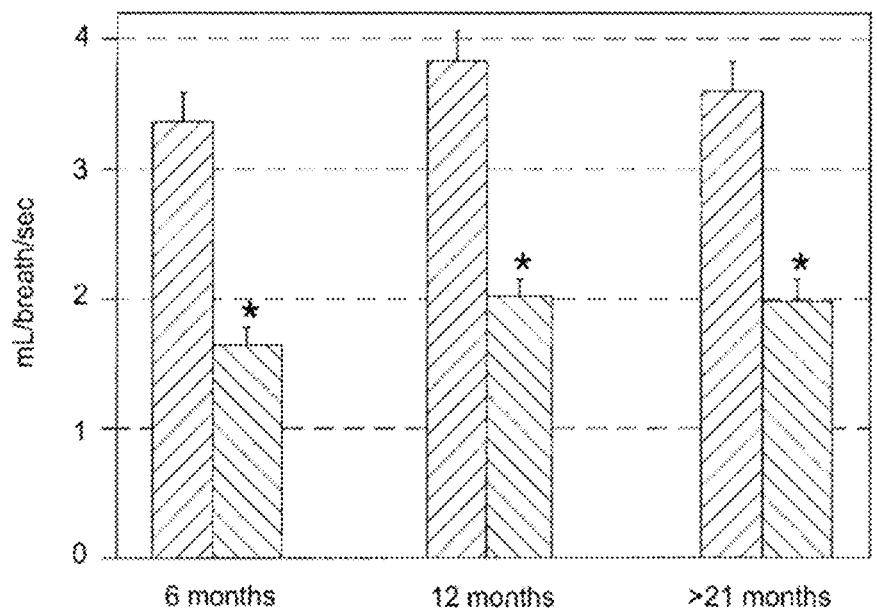
FIG. 8 is a graph showing mean inspiratory flow provides an estimate of the neural drive to breathe. Baseline mean inspiratory flow in 6 month, 12 month and >21 month control and $GAA^{-/-}$ mice. MEAN±SEM; *=different from control; no age or gender differences.

The attenuated mean inspiratory flow suggests the drive to breathe in GAA$^{-/-}$ mice may be decreased (FIG. 8).

Figure 9A:
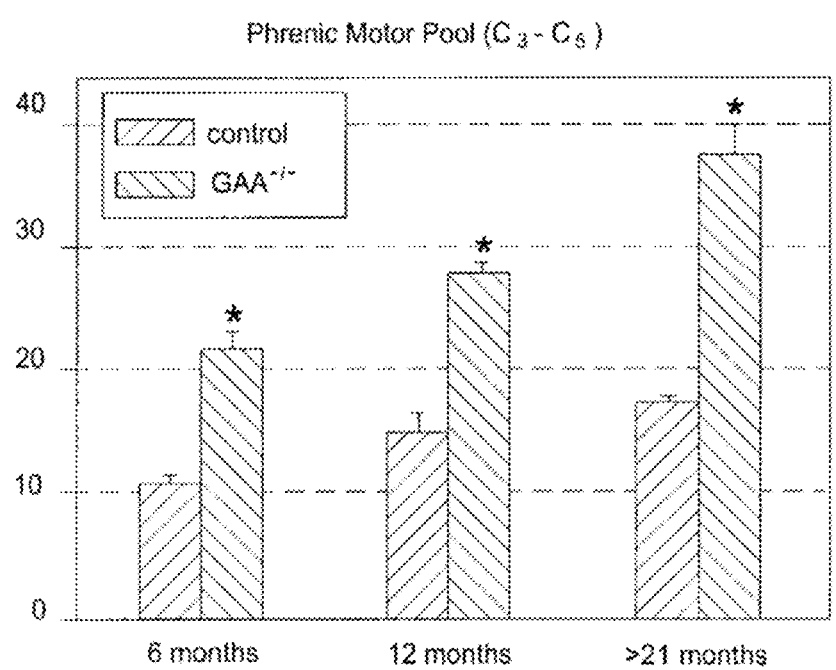
FIG. 9A is a graph and FIG. 9B is a histostain showing the results of glycogen quantification for spinal cord segments $C_3$-$C_5$ (FIG. 9A) in 6-month, 12-month and >21-month old control and $GAA^{-/-}$ mice. The phrenic motor pool lies within cervical spinal segments $C_3$-$C_5$. Histological glycogen detection (FIG. 9B) with the Periodic Acid Schiff stain. Phrenic motoneurons (arrows) were identified by the retrograde neuronal tracer Fluoro-Gold™ applied to the diaphragm.
Figure 9B:
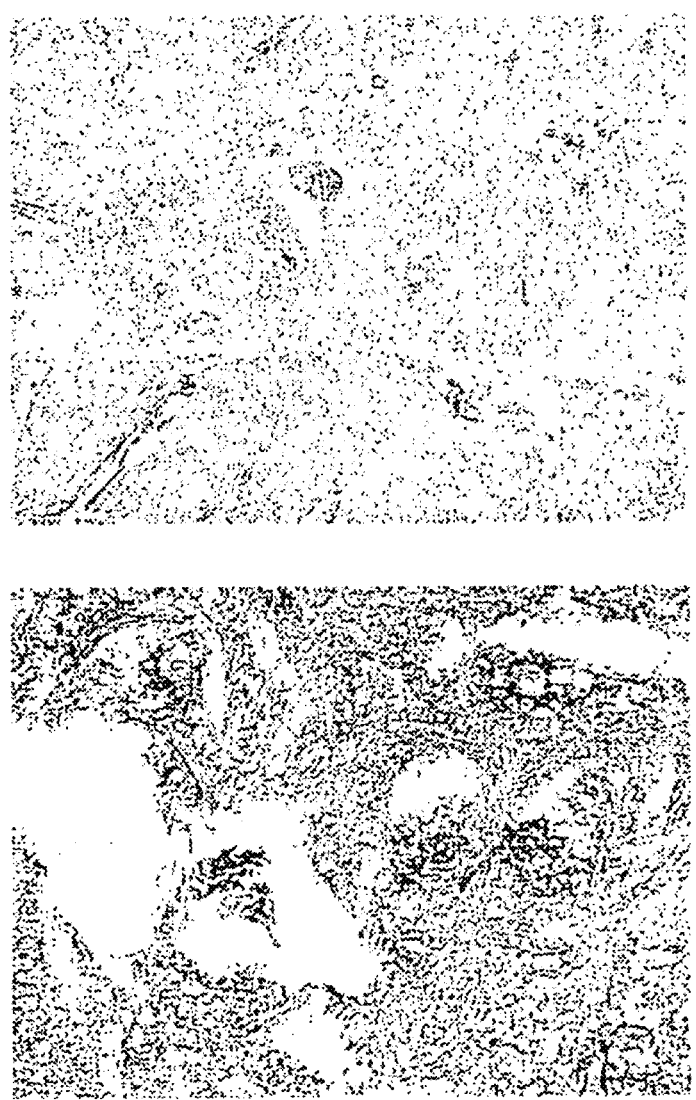

Accumulation of glycogen in the spinal cord of GAA$^{-/-}$ mice is observed beginning at 6 months of age (FIG. 9A and FIG. 9B).

Figure 10A:
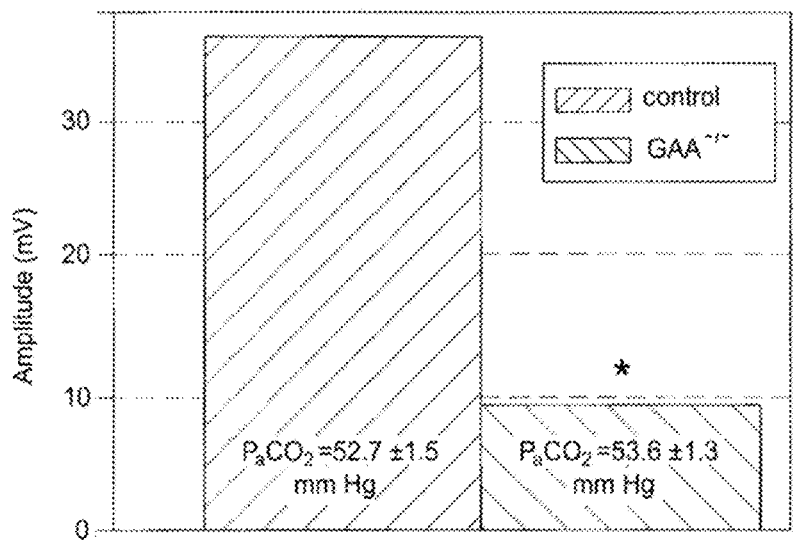
Figure 10B:
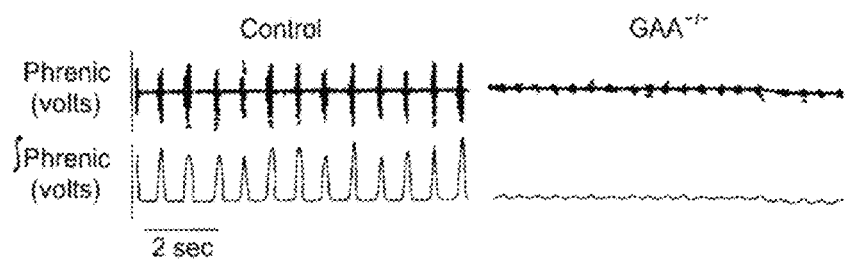
FIG. 10B is a neurogram showing results from a raw phrenic neurogram (top panel) and moving time average (bottom panel) for a mechanically ventilated control and $GAA^4$ mouse with similar $P_aCO_2$ values. Scale, amplifier gain, filter settings, and recording configurations were identical in the two preparations.

Efferent inspiratory phrenic output is reduced in GAA$^{-/-}$ vs. control (FIG. 10A and FIG. 10B).

Conclusion:

The ventilation deficits in GAA$^{-/-}$ mice are similar to the patient population. Mean inspiratory flow, glycogen quantification, muscle specific GAA mouse pattern of breathing and phrenic neurogram data are consistent with the hypothesis that these ventilatory difficulties reflect both a muscle and a neural component in GSD 11.

Example 5

Physiological Correction of Pompe Disease Using rAAV2/1 Vectors

Materials and Methods:

The recombinant AAV2 plasmid p43.2-GAA (Fraites, T. J., Jr. et al., *Mol. Ther.* 5:571-578, 2002) has been described previously. Recombinant AAV particles based on serotype 1 were produced using p43.2-GAA and were generated, purified, and titered at the University of Florida Powell Gene Therapy Center Vector Core Lab as previously described (Zolotukhin, S. et al., *Methods*, 28:158-167, 2002).

All animal studies were performed in accordance with the guidelines of the University of Florida Institutional Animal Care and Use Committee. The mouse model of Pompe disease (Gaa$^{-/-}$) used in this study has been described previously and was generated by a targeted disruption of exon 6 of the Gaa gene (Raben, N. et al., *J. Biol. Chem.*, 273:19086-19092, 1998). One-day-old Gaa$^{-/-}$ mice were administered 5×10$^{10}$ particles (30 μL total volume) rAAV2/1-CMV-GAA intravenously via the superficial temporal vein as described previously (Sands, M. S, and Barker, J. E., *Lab. Anim. Sci.*, 49:328-330, 1999).

Ten-, 24-, and 52-weeks' post-injection, tissue homogenates were assayed for GAA enzyme activity. Briefly, lysates were assayed for GAA activity by measuring the cleavage of the synthetic substrate 4-methylumbelliferyl-α-D-glucoside (Sigma M9766, Sigma-Aldrich. St. Louis, Mo.) after incubation for 1 h at 37° C. Successful cleavage yielded a fluorescent product that emits at 448 nm, as measured with an FLx800 microplate fluorescence reader (Bio-Tek Instruments, Winooski, Vt.). Protein concentration was measured using the Bio-Rad DC protein assay kit (Bio-Rad, Hercules, Calif.). Data are represented as percentage of normal levels of GAA in each tissue after subtraction of untreated Gaa$^{-/-}$ tissue levels. Detection of anti-GAA antibodies was performed by ELISA.

Segments of treated and untreated diaphragm were fixed overnight in 2% glutaraldehyde in PBS, embedded in Epon 812® (Shell), sectioned, and stained with periodic acid-Schiff (PAS) by standard methods.

Mice were anesthetized with a mixture of 1.5-2% isoflurane and 1 L/min oxygen then positioned supine on a heating pad. ECG leads were placed subcutaneously in the right shoulder, right forelimb, left forelimb, left hind limb and the tail. ECG tracings were acquired for five minutes per animal using PowerLab ADInstruments unit and Chart acquisition software (ADnstruments, Inc., Colorado Springs, Colo.). Peak intervals from all tracings were averaged for each animal and then averaged within each experimental group.

Assessment of Cardiac Mass:

Cardiac MRI was performed on a 4.7 T Bruker Avance spectrometer (Bruker BioSpin Corporation, Billerica, Mass.) at the University of Florida Advanced Magnetic Resonance Imaging and Spectroscopy (AMRIS) facility. The animals were anesthetized using 1.5% isoflurane (Abbott Laboratories, North Chicago, Ill.) and 1 L/min oxygen. The animals were placed prone on a home-built quadrature transmit-and-receive surface coil with the heart placed as near to the center of the coil as possible. The images were acquired using cardiac gating and were triggered at the peak of the R-R wave (SA Instruments, Inc., Stony Brook, N.Y.). The heart was visualized by acquiring single short axis slices along the length of the left ventricle. The images were acquired using a gradient recalled echo (GRE) sequence (matrix=256×128, TE=2.4 ms, FOV=4 cm×3 cm, 7-8 slices, thickness=1 mm). The effective TR (pulse repetition time) was governed by the heart rate of the animal, which was observed to maintain consistency and anesthesia was adjusted accordingly. The R-R interval was typically 250 ms.

Images were processed using CAAS MRV for mice (Pie Medical Imaging. Maastricht, The Netherlands). Contours were drawn for the epicardium and the endocardium for each slice along the length of the left ventricle at both end diastole and end systole. The results were exported and analyzed and end diastolic myocardial mass was calculated.

Isometric force-frequency relationships were used to assess diaphragm contractile force. The diaphragm is isolated, with the ribs and central tendon attached, and placed in Krebs-Henseleit solution equilibrated with a 95% $O_2$/5% $CO_2$ gas mixture on ice. A single muscle strip, cut from the ventral costal diaphragm parallel to the connective tissue fibers, is used to determine force-frequency relationships. Plexiglas® clamps are attached to the diaphragm strip via clamping to the rib and central tendon. The muscle strip is suspended vertically in a water-jacketed tissue bath (Radnoti, Monrovia, Calif.) containing Krebs-Henseleit solution equilibrated with a 95% $O_2$/5% $CO_2$ gas mixture, maintained at 37° C., pH 7.4, and equilibrated for 15 min. To measure isometric contractile properties, the clamp attached to the central tendon is connected to a force transducer (Model FT03. Grass Instruments, West Warwick, R.I.). The transducer outputs are amplified and differentiated by operational amplifiers and undergo A/D conversion using a computer-based data acquisition system (Polyview. Grass Instruments). To determine the muscle strip optimal length ($L_o$) for isometric tetanic tension, the muscle is field-stimulated (Model S48, Grass Instruments) along its entire length using platinum wire electrodes. Single twitch contractions are evoked, followed by step-wise increases in muscle length, until maximal isometric twitch tension is obtained. All contractile properties are measured isometrically at $L_o$. Peak isometric tetanic force is measured at 10, 20, 40, 80, 100, 150, and 200 Hz. Single 500 ms trains are used, with a four-minute recovery period between trains to prevent fatigue. Calipers are used to measure $L_o$ before removal of the muscle from the apparatus. The muscle tissue is then dissected away from the rib and central tendon, blotted dry, and weighed. The muscle cross-sectional area (CSA) is determined using the equation CSA (cm$^2$)=[muscle strip mass (g)/fiber length $L_o$ (cm)×1.056 (g/cm$^3$)], where 1.056 g/cm$^3$ is the assumed density of muscle. The calculated CSA is used to normalize isometric tension, which is expressed as N/cm$^2$.

Respiratory function was assayed using barometric whole body plethysmography. Unanesthetized, unrestrained C57BL6/129SvJ, Gaa$^{-/-}$, and rAAV2/1-treated Gaa$^{-/-}$ mice were placed in a clear Plexiglas® chamber (Buxco, Inc., Wilmington, N.C.). Chamber airflow, pressure, temperature, and humidity are continuously monitored and parameters such as frequency, minute ventilation, tidal volume, and peak inspiratory flow are measured and analyzed using the method by Drorbaugh and Fenn and recorded using Bio-System XA software (Buxco, Inc.) (Drorbaugh, J. E. and Fenn. W. O., Pediatrics, 16:81-87, 1955). Baseline measurements are taken under conditions of normoxia ($F_iO_2$:0.21, $F_iCO_2$: 0.00) for a period of one hour followed by a ten minute exposure to hypercapnia ($F_iO_2$: 0.21, $F_iCO_2$: 0.07).

Results:

Cardiac and respiratory function in rAAV2/1-treated animals was examined. Similar to the Pompe patient population, electrocardiogram (ECG) measurements (P-R interval) were significantly shortened in the mouse model. In rAAV2/1-treated mice, a significant improvement in cardiac conductance with prolonged P-R intervals of 39.34±1.6 ms was shown, as compared to untreated controls (35.58±0.57 ms) (p≤0.05). In addition, using cardiac magnetic resonance imaging (MRI), a marked decrease in cardiac left ventricular mass was noted from 181.99±10.70 mg in untreated age-matched controls to 141.97±19.15 mg in the rAAV2/1-treated mice. Furthermore, the mice displayed increased diaphragmatic contractile force to approximately 90% of wild-type peak forces with corresponding significantly improved ventilation (particularly in frequency, minute ventilation, and peak inspiratory flow), as measured using barometric whole body plethysmography. These results demonstrate that in addition to biochemical and histological correction, rAAV2/1 vectors can mediate sustained physiological correction of both cardiac and respiratory function in a model of fatal cardiomyopathy and muscular dystrophy.

Systemic Delivery of rAAV2/1 can Result in Sustained Restoration of Cardiac and Diaphragmatic GAA Enzymatic Activity in Gaa$^{-/-}$ Mice $5\times10^{10}$ particles of rAAV2/1-CMV-hGAA were injected into one-day-old Gaa$^{-/-}$ mice via the superficial temporal vein. Serial serum samples were collected to assay for the formation of anti-hGAA antibodies and cardiac and diaphragm tissues were analyzed for GAA enzyme activity at ten. 24, and 52 weeks post-injection. A transient humoral immune response was detected by the presence of circulating anti-hGAA antibodies. Antibody titers were highest at eleven weeks post-injection with an average of 16.08=4.66-fold above background levels. After fifteen weeks, antibody titers dropped significantly to 4.72±1.28-fold above background and were further reduced to background levels by 31 weeks post-treatment. Peak GAA enzyme activity levels were detected at 24 weeks with 4223±1323% and 138.18±59.7% of normal (Gaa$^{-/-}$) activity in heart and diaphragm, respectively, with levels dropping to 593.79±197.35% and 39.81±17.43% of normal, respectively, at one year post-injection.

Figure 11:
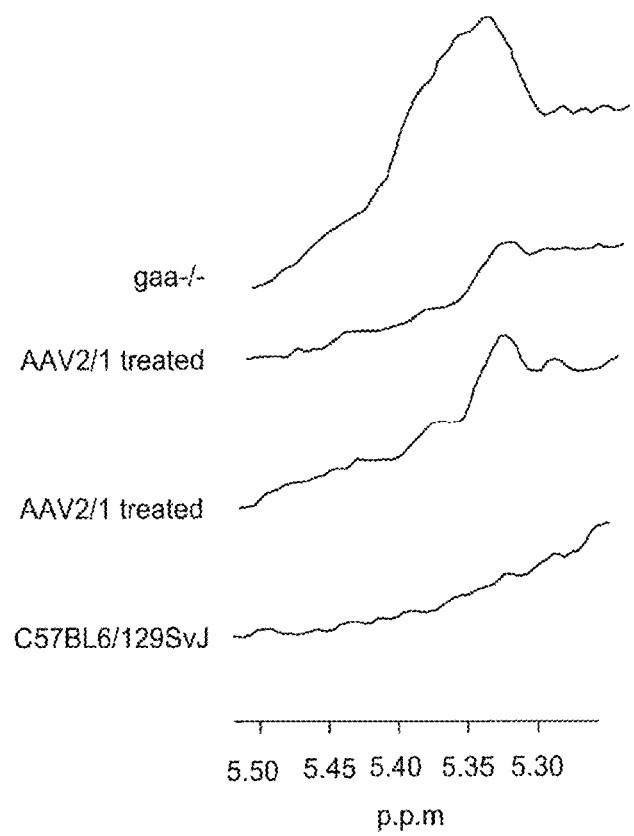
FIG. 11 is a graph showing that intravenous injection of rAAV2/1 leads to clearance of glycogen in affected diaphragm tissue. One year post-injection, diaphragm tissue from $Gaa^{-/-}$ mice administered rAAV2/1-CMV-GAA intravenously and untreated age-matched control $Gaa^{-/-}$ mice was fixed and stained with periodic acid-Schiff (PAS) by standard methods (Richard Allen, Kalamazoo, Mich.). Photographs were taken using a Zeiss light microscope, Olympus camera, and MagnaFire® digital recording system. Magnification×400.
Figure 12A:
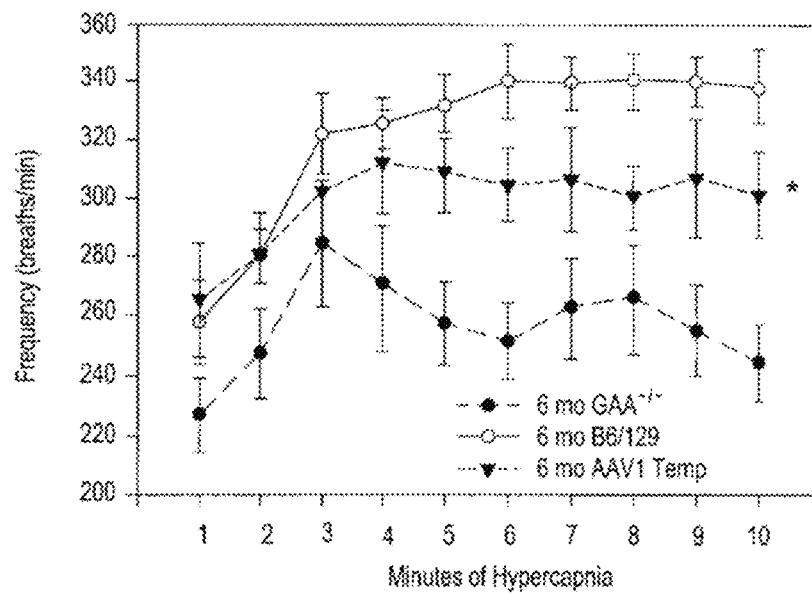
FIG. 12A, FIG. 12B, FIG. 12C and FIG. 12D are a series of graphs showing that systemic delivery of rAAV2/1-CMV-hGAA confers improved ventilation in response to hypercapnia six months post-treatment. Ventilation of treated $Gaa^{-/-}$ (n=6) and age-matched untreated $Gaa^{-/-}$ and C57BL6/129SvJ (n=10) was assessed using barometric whole-body plethysmography. *=p≤0.05
Figure 12B:
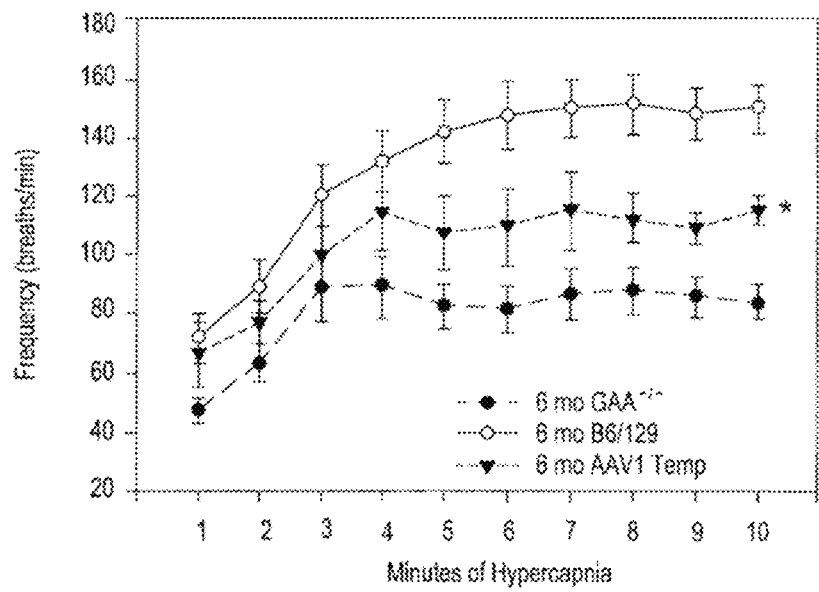
Figure 12C:
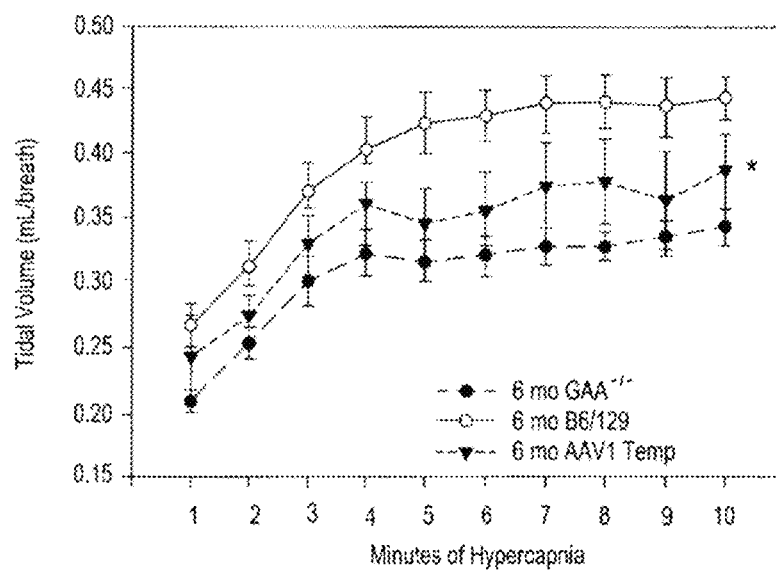
Figure 12D:
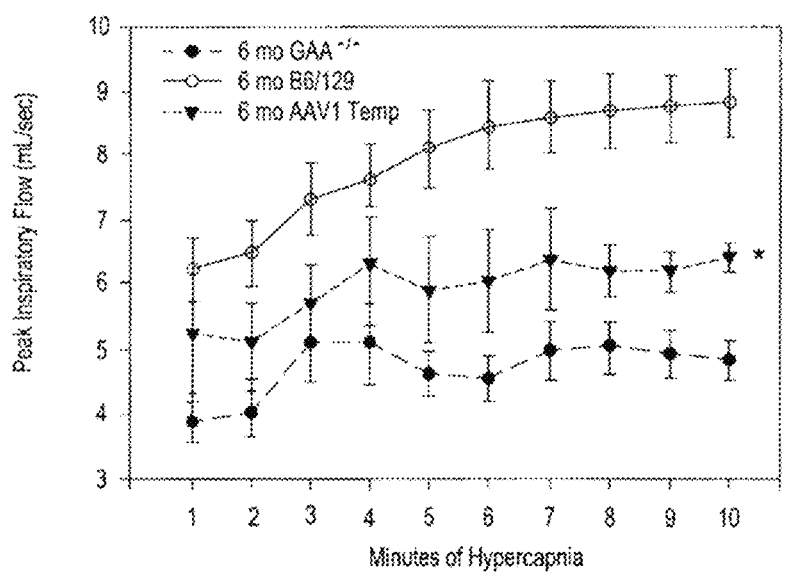
Figure 13A:
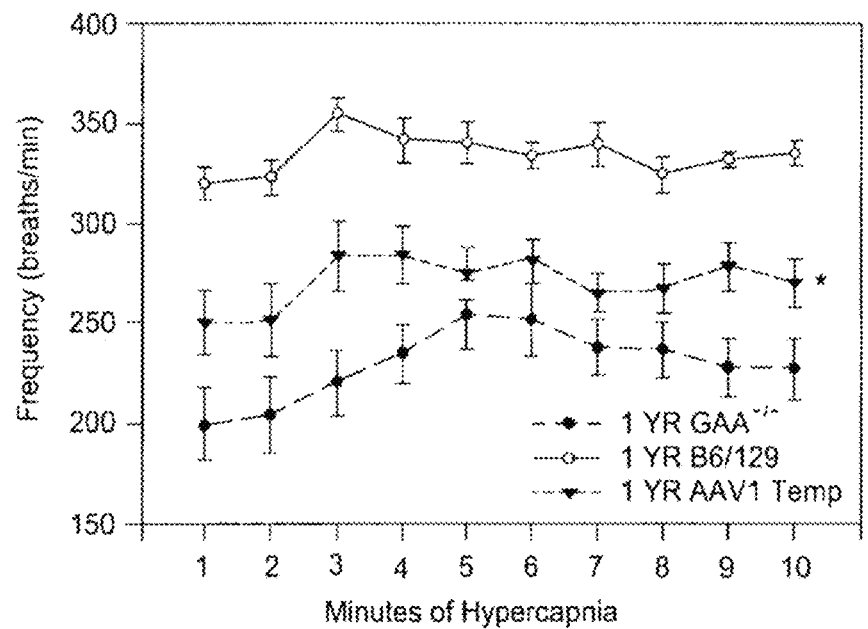
FIG. 13A, FIG. 13B, FIG. 13C and FIG. 13D are a series of graphs showing that systemic delivery of rAAV2/1-CMV-hGAA confers improved ventilation in response to hypercapnia twelve months' post-treatment. Ventilation of treated $Gaa^{-/-}$ (n=12) and age-matched untreated $Gaa^{-/-}$ and C57BL6/129SvJ (n=10) was assessed using barometric whole-body plethysmography. *=p≤0.05
Figure 13B:
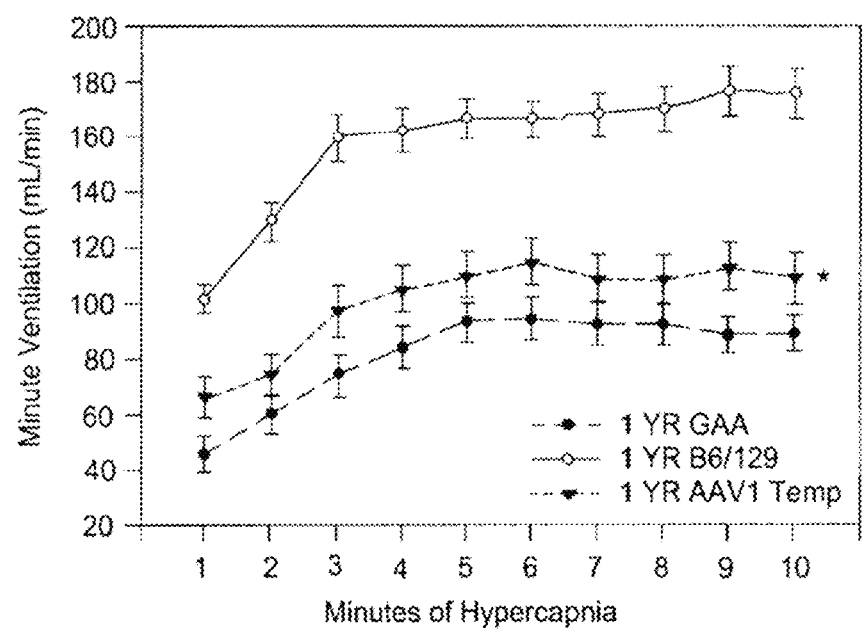
Figure 13C:
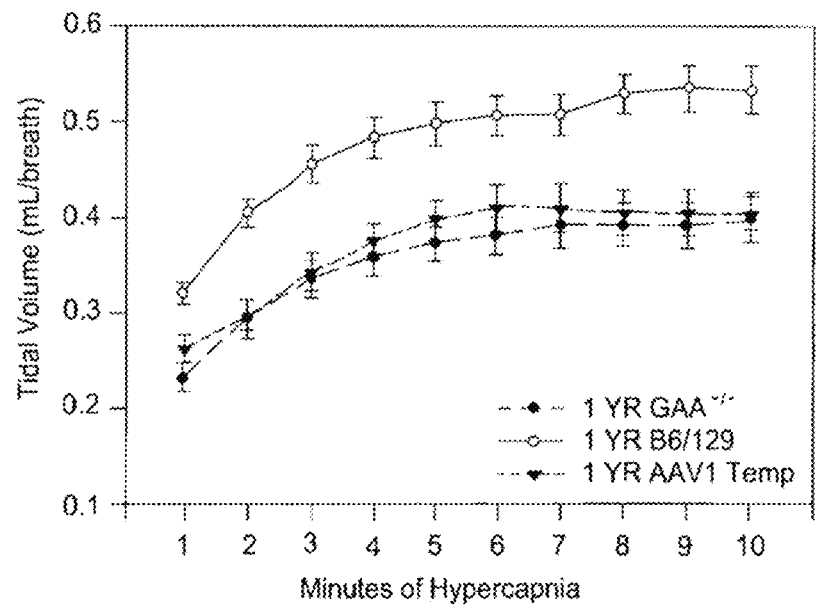
Figure 13D:
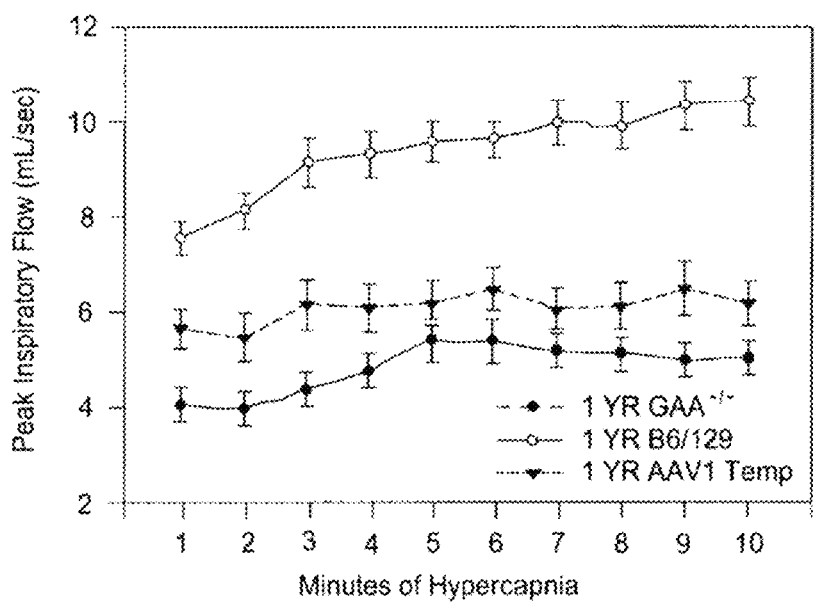
Figure 14A:
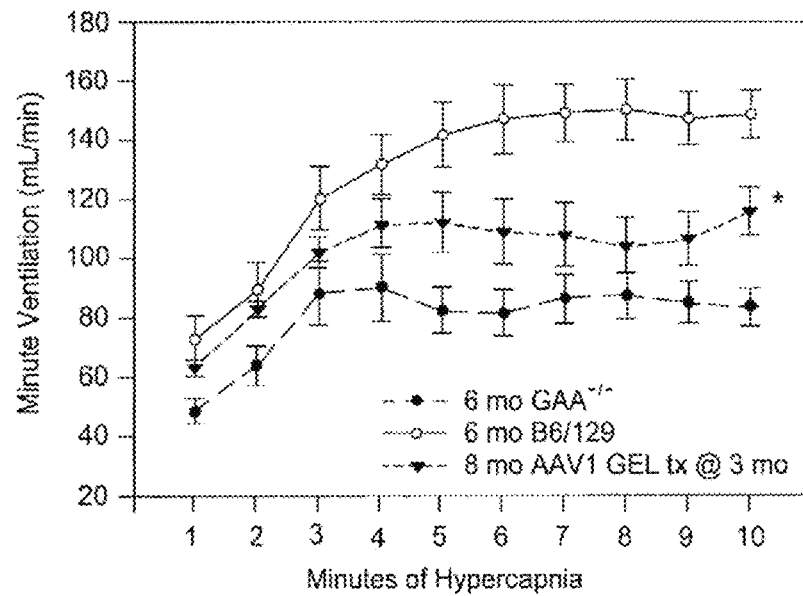
FIG. 14A, FIG. 14B, FIG. 14C and FIG. 14D are a series of graphs showing that ventilatory function is significantly improved in AAV2/1-treated mice. Ventilatory function was assayed by awake, unrestrained, whole body barometric plethysmography. Graphs show the minute ventilation response to hypercapnia over the 10-minute period of time.
Figure 14B:
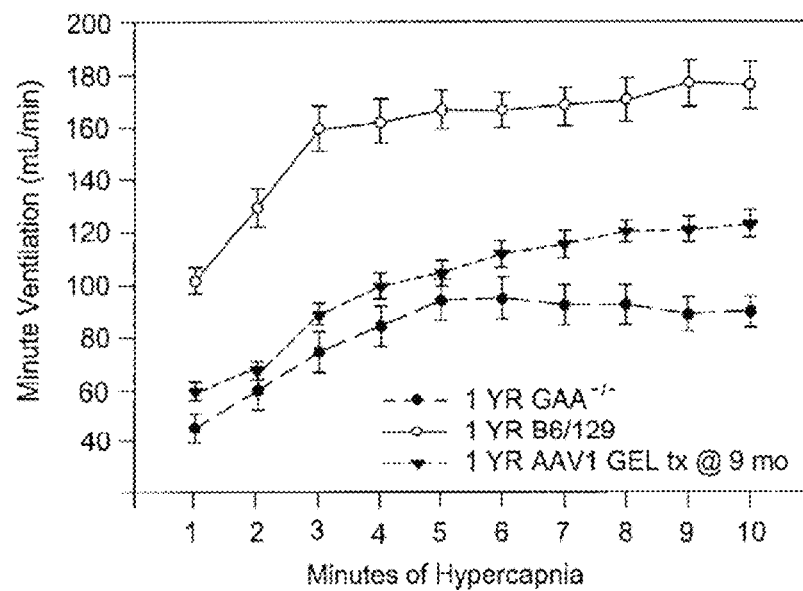
Figure 14C:
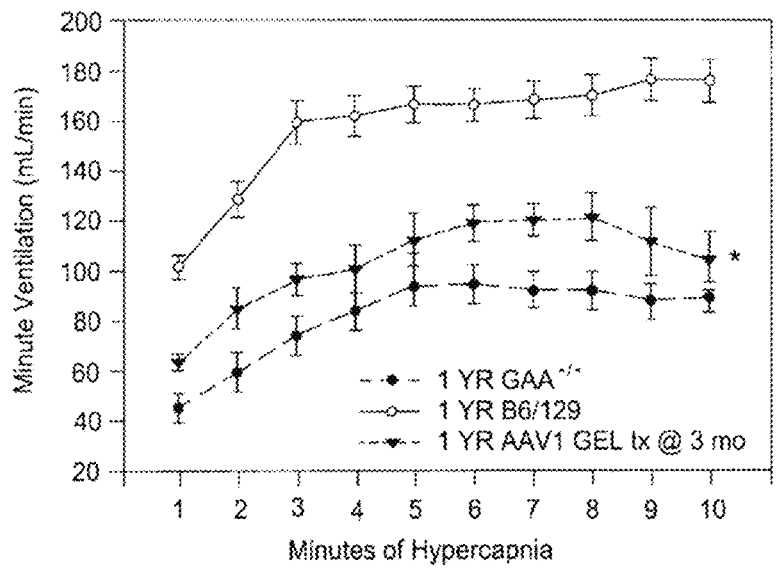
Figure 14D:
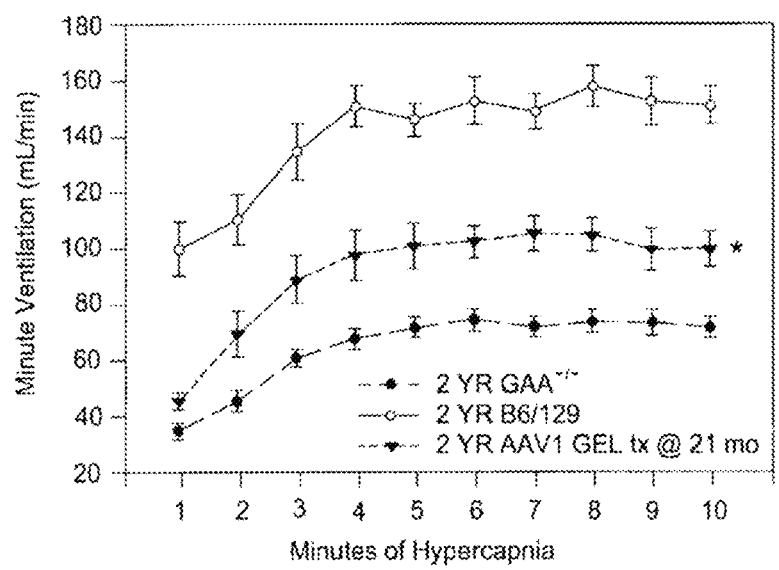
Figure 15A:
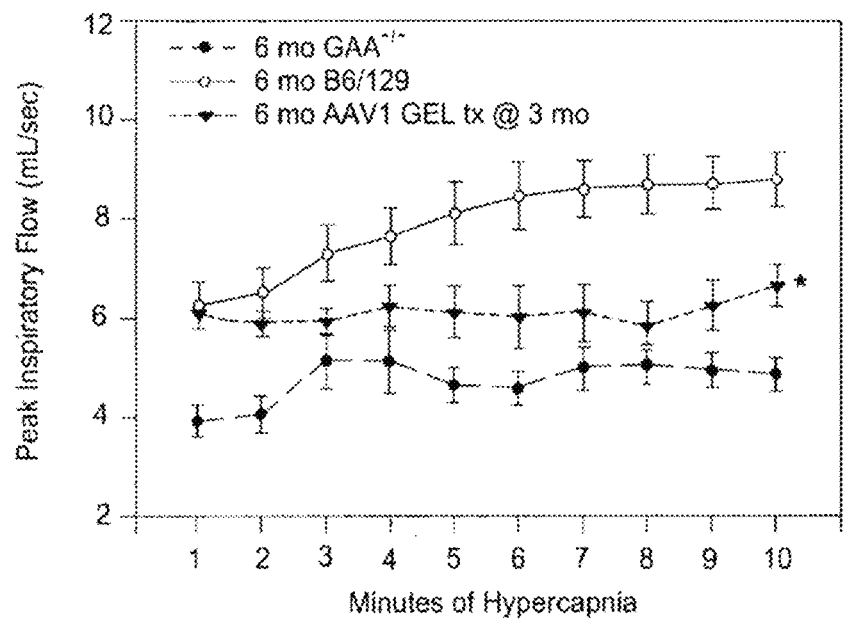
FIG. 15A, FIG. 15B, FIG. 15C and FIG. 15D are a series of graphs showing that ventilatory function is significantly improved in AAV2/1-treated mice. Graphs show the peak inspiratory flow response to hypercapnia over the 10-minute period of time.
Figure 15B:
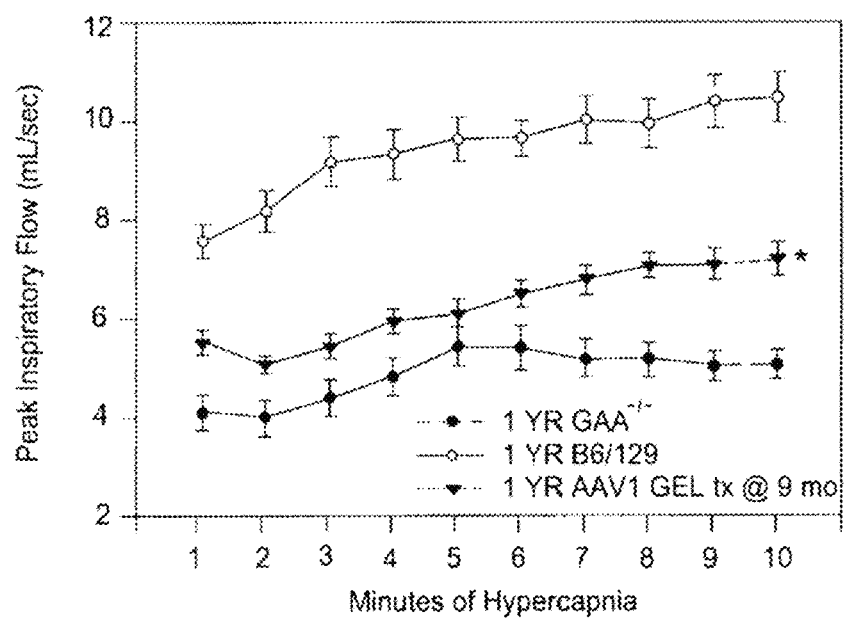
Figure 15C:
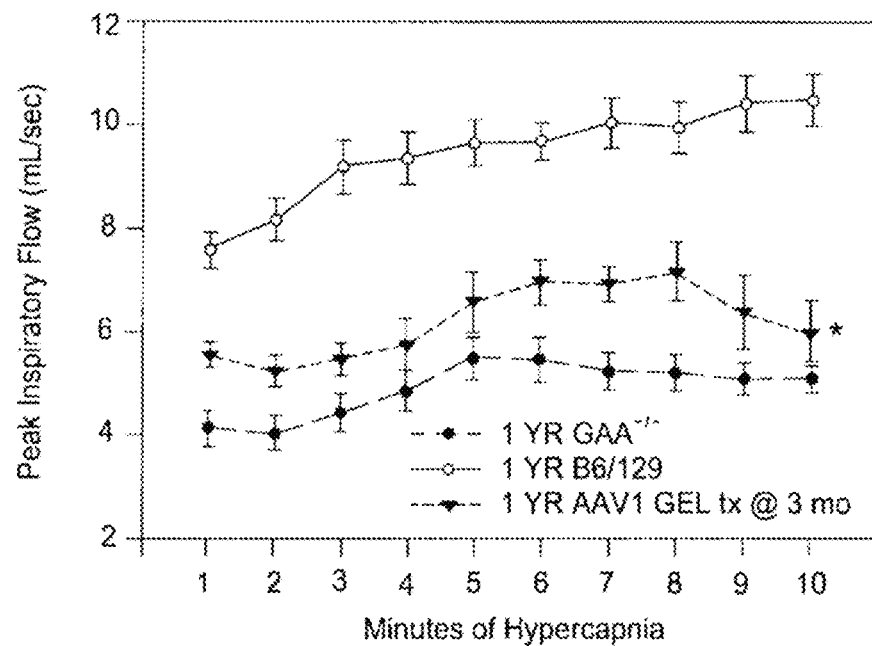
Figure 15D:
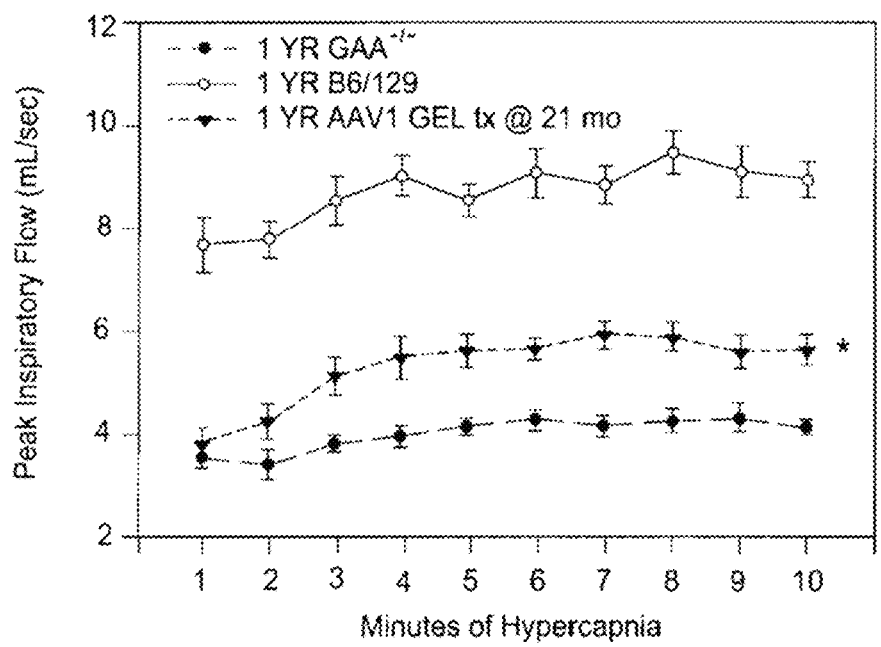

Recombinant AAV2/1-Mediated Therapy can Correct Cardiac Mass and Conductance Abnormalities in Gaa$^{-/-}$ Mice The results described above demonstrate that delivery of rAAV2/1-CMV-hGAA vectors results in sustained biochemical and histological correction of the Pompe disease cardiac phenotype as evidenced by supraphysiologic levels of GAA enzyme activity and the concomitant clearance of glycogen, as determined by periodic acid-Schiffs reagent staining. Proton magnetic resonance spectroscopy ($^1$H-MRS) of perchloric acid extracts of cardiac tissues further supported these findings. As shown in FIG. 11, a pronounced glycogen peak could be detected in a 1-year-old Gaa$^{-/-}$ mouse. An average 70% reduction was observed in the glycogen content in hearts of 1-year old Gaa$^{-/-}$ mice treated with rAAV2/1-CMV-hGAA as neonates, as compared to untreated mice.

The physiological effects of rAAV2/1-mediated therapy on cardiac function were examined. A shortened P-R interval is characteristic in electrocardiograms of patients with Pompe disease. At one year of age, Gaa$^{-/-}$ mice also display a significantly shortened P-R interval. As shown in Table 1, one-year-old Gaa$^{-/-}$ mice that were administered rAAV2/1-CMV-hGAA as neonates demonstrated significantly improved cardiac conductance with a prolonged P-R interval of 39.32±1.6 ms, as compared to untreated controls (35.58±0.57 ms) (p<0.05). In addition to aberrant cardiac conductance, both the patient population and mouse model of Pompe disease also exhibit pronounced cardiac hypertrophy. Using magnetic resonance imaging (MRI), previous studies have shown that cardiac mass can be accurately quantified, noninvasively, in mouse models. MRI was used to assess left ventricular (LV) mass in the Gaa$^{-/-}$ model. At one year of age, Gaa$^{-/-}$ mice have significantly higher LV mass (181.99±10.7 mg) as compared to age-matched wild-type Gaa$^{-/-}$ (C57BL6/129SvJ) mice (140.79±5.12 mg). As shown in Table 1, rAAV2/1-treated Gaa$^{-/-}$ mice have LV masses similar to that of wild-type mice at one year of age (141.97±19.15 mg). While the reduced LV mass in the rAAV2/1-treated mice was not quite statistically significant (p=0.06), the trend of smaller LV mass is thought to be real and would likely be significant with a larger sample population.

TABLE 1

Intravenous Injection of rAAV2/1 Leads to Decreased Cardiac Mass and Elongated P-R Interval

| | Ventricular Mass (mg) | P-R Interval (ms) |
|---|---|---|
| 1 year-old Gaa$^{-/-}$ | 181.99 ± 10.70 | 35.58 ± 0.57 |
| 1 year-old BL6/129 | 140.79 ± 5.12 | 45.13 ± 1.16 |
| 1 year-old AAV2/1-treated | 141.97 ± 19.15** | 39.34 ± 1.60* |

One year post-injection, rAAV2/1-treated mice (n = 7) as well as untreated age-matched control Gaa$^{-/-}$ (n = 7) and C57 (n = 5) mice were subjected to electrocardiography as well as magnetic resonance imaging.

Diaphragm Contractility and Ventilatory Function are Significantly Improved after Administration of rAAV2/1 Vectors As respiratory insufficiency manifests as one of the most prevalent clinical complications of Pompe disease, the effects of rAAV2/1-mediated gene therapy on ventilatory function was examined in Gaa; mice (Kishnani, P. S. et al., *Genet. Med.*, 8:267-288, 2006; Hagemans, M. L. et al., *Neurology*, 66:581-583, 2006; Mellies, U. et al., *Neurology*, 64:1465-1467, 2005). PAS staining of diaphragm from one-year-old Gaa$^{-/-}$ mice administered rAAV2/1-CMV-hGAA intravenously, showed a significant reduction in the amount of accumulated glycogen, corresponding with the therapeutic level of GAA expression. Diaphragm muscle was isolated and assessed for isometric force generation. Diaphragm contractile force generated by rAAV2/1-treated mice was significantly improved as compared to age-matched, untreated controls, and even younger, 3-month-old untreated animals. At the maximal stimulation frequency (200 Hz), the force generated by diaphragms from rAAV2/1-treated mice was 21.98±0.77 N/cm$^2$, whereas control one-year-old Gaa$^{-/-}$ mouse diaphragms generated an average of 13.95±1.15 N/cm$^2$.

To measure ventilation, barometric whole-body plethysmography was used.

Plethysmography allows for the simultaneous measurement of multiple parameters of ventilation, including frequency (breaths/min), tidal volume (mL/breath), minute ventilation (mLumin), and peak inspiratory flow (mL/sec), in unanesthetized, unrestrained mice (DeLorme, M. P, and Moss, O. R., *J. Pharmacol. Toxicol. Methods*, 47:1-10, 2002). Mice were subjected to 90 min of normoxic air followed by a ten minute exposure to hypercapnic (7% $CO_2$) conditions. The elevated $CO_2$ levels increases the drive to breathe and allows for an assessment of an extended range of respiratory capabilities. Plethysmography was performed at 6 and 12 months of age. Untreated Gaa$^{-/-}$ mice showed dramatically diminished ventilatory capacity at both 6 and 12 months of age, as demonstrated by significantly reduced frequency, tidal volume, minute ventilation, and peak inspiratory flow (p<0.01) in response to hypercapnia. Conversely, at 6 months, rAAV2/1-treated Gaa$^{-/-}$ mice had significantly improved ventilation across all parameters measured in response to hypercapnia (FIG. 12A-FIG. 12D), and at one year post-treatment, frequency, minute ventilation, and peak inspiratory flows were still significantly higher than that of untreated age-matched controls (p<0.05) (FIG. 13A-FIG. 13D).

The experiments described herein demonstrate that in addition to biochemical correction of the disease phenotype, administration of a therapeutic rAAV2/1 vector can lead to functional correction as well. Treatment with a therapeutic rAAV2/1 vector resulted in a significant improvement in cardiac function as indicated by an elongated P-R interval in electrocardiograms of treated animals.

These experiments also demonstrate that an average of approximately 39% normal GAA activity can result in clearance of glycogen in the diaphragm, the major muscle involved in ventilation, as well as a dramatic improvement in the contractile capability of the diaphragm. Furthermore, a significant improvement of ventilatory function was observed under conditions of hypercapnia. Similar to the cardiac function, while marked improvement is noted in ventilatory function, the correction is only partial. A significant difference in ventilation between the treated animals and respective untreated controls during exposure to normoxic conditions was not observed.

Experiments performed in the Gaa$^{-/-}$ mouse model suggest that phrenic motoneuron activity in Gaa$^{-/-}$ mice is attenuated and demonstrate that a single intravenous administration of a therapeutic rAAV2/1 vector can give rise to sustained correction of the cardio-respiratory phenotype in a mouse model of metabolic muscular dystrophy.

Example 6

Gel-Mediated Delivery of rAAV2/1 Vectors to Correct Ventilatory Function in Pompe Mice with Progressive Forms Disease The consequences of a gel-mediated method of delivery of a therapeutic recombinant AAV2 viral vectors pseudotyped with viral capsids of serotype 1 (rAAV2/1) in Gaa$^{-/-}$ mice treated at 3, 9, and 21-months of age was characterized. In mice treated at 3 months of age, a significant improvement in diaphragm contractile strength at 6 months that is sustained out to 1 year of age was observed compared to age-matched untreated controls. Similarly, significantly improved contractile strength was observed in mice treated at 9 and 21 months of age, 3 months post-treatment (p≤0.05). Ventilation under normoxic conditions (the ratio of tidal volume/inspiratory time, the ratio of minute ventilation to expired $CO_2$, and peak inspiratory flow) were all improved in mice treated at 3 months of age and tested at 6 months (p≤0.05), but was not sustained at 1 year of age, as compared to untreated age-matched controls. In all rAAV2/1 gel-treated mice (treated 3, 9, and 21 months of age) minute ventilation and peak inspiratory flows were significantly improved under hypercapnic conditions. These results demonstrate that in gel-mediated delivery of rAAV2/1 vectors can mediate significant physiological improvement of ventilatory function in a model of muscular dystrophy.

Materials and Methods:

Packaging and Purification of Recombinant AAV2/1 Vectors

The recombinant AAV2 plasmid p43.2-GAA has been described previously. Recombinant AAV particles based on serotype 1 were produced using p43.2-GAA and were generated, purified, and titered at the University of Florida Powell Gene Therapy Center Vector Core Lab.

In Vivo Delivery

All animal studies were performed in accordance with the guidelines of the University of Florida Institutional Animal Care and Use Committee. Three, nine, and 21-month-old Gaa$^{-/-}$ mice were administered $1\times10^{11}$ particles rAAV2/1-CMV-GAA directly to the diaphragm in a gel matrix as described previously (see U.S. patent application Ser. No. 11/055,497 filed Feb. 10, 2005).

Histological Assessment of Glycogen Clearance

Segments of treated and untreated diaphragm were fixed overnight in 2% glutaraldehyde in PBS, embedded in Epon 812® (Shell), sectioned, and stained with PAS by standard methods.

Assessment of Diaphragm Contractile Force

Isometric force-frequency relationships were used to assess diaphragm contractile force. The diaphragm is isolated, with the ribs and central tendon attached, and placed in Krebs-Henseleit solution equilibrated with a 95% $O_2$/5% CO, gas mixture on ice. A single muscle strip, cut from the ventral costal diaphragm parallel to the connective tissue fibers, is used to determine force-frequency relationships. Plexiglas® clamps are attached to the diaphragm strip via clamping to the rib and central tendon. The muscle strip is suspended vertically in a water-jacketed tissue bath (Radnoti, Monrovia, Calif.) containing Krebs-Henseleit solution equilibrated with a 95% $O_2$/5% $CO_2$ gas mixture, maintained at 37° C., pH 7.4, and equilibrated for 15 min. To measure isometric contractile properties, the clamp attached to the central tendon is connected to a force transducer (Model FT03, Grass Instruments, West Warwick, R.I.). The transducer outputs are amplified and differentiated by operational amplifiers and undergo A/D conversion using a computer-based data acquisition system (Polyview, Grass Instruments). To determine the muscle strip optimal length ($L_o$) for isometric tetanic tension, the muscle is field-stimulated (Model S48, Grass Instruments) along its entire length using platinum wire electrodes. Single twitch contractions are evoked, followed by step-wise increases in muscle length, until maximal isometric twitch tension is obtained. All contractile properties are measured isometrically at $L_o$. Peak isometric tetanic force is measured at 10, 20, 40, 80, 100, 150, and 200 Hz. Single 500-ms trains are used, with a four-minute recovery period between trains to prevent fatigue. Calipers are used to measure $L_o$ before removal of the muscle from the apparatus. The muscle tissue is then dissected away from the rib and central tendon, blotted dry, and weighed. The muscle cross-sectional area (CSA) is determined using the equation:

CSA ($cm^2$)=[muscle strip mass (g)/fiber length $L_o$ (cm)×1.056 (g/$cm^3$)], where 1.056 g/$cm^3$ is the assumed density of muscle. The calculated CSA is used to normalize isometric tension, which is expressed as N/$cm^2$.

Assessment of Ventilatory Function

Ventilatory function was assayed using barometric whole body plethysmography. Unanesthetized, unrestrained C57BL6/129SvJ (n=10), Gaa$^{-/-}$ (n=10), and rAAV2/1-treated Gaa$^{-/-}$ mice (n=8) are placed in a clear Plexiglas® chamber (Buxco, Inc., Wilmington, N.C.). Chamber airflow, pressure, temperature, and humidity are continuously monitored and parameters such as frequency, minute ventilation, tidal volume, and peak inspiratory flow are measured and analyzed using the method by Drorbaugh and Fenn and recorded using BioSystem XA software (Buxco, Inc.). Baseline measurements are taken under conditions of normoxia ($F_IO_2$: 0.21, $F_ICO_2$: 0.00) for a period of one hour followed by a ten minute exposure to hypercapnia ($F_IO_2$: 0.93, $F_ICO_2$: 0.07).

Efferent Phrenic Nerve Recordings

Mice were anesthetized with 2-3% isoflurane, trachea canulated, and connected to a ventilator (Model SAR-830/AP, CWE, Incorporated). Ventilator settings were manipulated to produce partial pressures of arterial $CO_2$ between 45-55 mmHg. A jugular catheter (0.033 outer diameter; RenaPulse™ tubing. Braintree Scientific) was implanted and used to transition the mice from isoflurane to urethane (1.0-1.6 g/kg) anesthesia. A carotid arterial catheter (mouse carotid catheter. Braintree Scientific) was inserted to enable blood pressure measurements (Ohmeda P10-EZ) and withdrawal of 0.15-mL samples for measuring arterial $PO_2$ and $PCO_2$ (1-Stat portable blood gas analyzer). Mice were vagotomized bilaterally and paralyzed (pancuronium bromide; 2.5 mg/kg, i.v.). The right phrenic nerve was isolated and placed on a bipolar tungsten wire electrode. Nerve electrical activities were amplified (2000×) and filtered (100-10,000 Hz; Model BMA 400, CWE, Incorporated). When monitoring spontaneous inspiratory activity in the phrenic neurogram, the amplified signal was full-wave rectified and smoothed with a time constant of 100 ms, digitized and recorded on a computer using Spike2 software (Cambridge Electronic Design; Cambridge. UK). The amplifier gain settings and signal processing methods were identical in all experimental animals. The 30 seconds prior to each blood draw were analyzed for the mean phrenic inspiratory burst amplitude from these digitized records.

Results:

Gel-Mediated Delivery of rAAV2/1 can Result in Efficient Transduction of Diaphragm and Clearance of Accumulated Glycogen Histological analysis of transduced diaphragms from mice administered 1×10$^{11}$ particles rAAV encoding CMV promoter-driven β-galactosidase (lacZ) showed that not only could administration of rAAV2/1 lead to uniform transduction across the surface of the diaphragm on which the vector was applied, but that rAAV2/1 vector could transduce the entire thickness of the diaphragm tissue. In comparison, rAAV2 vectors cold only and transduce the first few layers of cells.

1×10$^{11}$ particles of rAAV2/I-CMV-GAA were administered to diaphragms of adult three, nine, and 21-month-old Gaa$^{-/-}$ mice using the gel method. GAA enzyme activity was assessed three months post-treatment for each age group and in an additional cohort of mice treated at three months of age, diaphragmatic GAA activity was assessed at nine months post-treatment. An average of 84.97±38.53% normal GAA activity was observed in treated diaphragms. No significant difference in GAA activity was seen with respect to age at treatment, or with time post-treatment as in the case of mice treated at three months of age and analyzed at 6 month and 1 year of age, respectively. Periodic acid-Schiff (PAS) staining of diaphragm tissue also revealed a reduction in the amount stored glycogen in the tissue for all treated age groups.

Diaphragm Contractility is Significantly Improved after Administration of rAAV2/1 Vectors Similar to the Pompe patient population, Gaa$^{-/-}$ mice have a progressive weakening of diaphragm contractile strength correlating with duration of disease. Isometric force-frequency relationships from diaphragm muscle isolated from untreated Gaa$^{-/-}$ mice (n=3 for each group) show a significant decrease in contractile strength with age from 3 months of age to 2 years of age. After gel-mediated administration of rAAV2/1-CMV-hGAA to diaphragms of Gaa$^{-/-}$ mice, a significant improvement was seen in the contractile strength in the diaphragm muscle as compared to age-matched untreated controls. For animals that were treated at 3 months of age, significantly improved diaphragm contractile strength at 6 months (peak force of 24.83±3.31 N/$cm^2$) was sustained out to 1 year (21.59±1.59 N/$cm^2$) of age, as compared to age-matched untreated controls (peak force of 16.53±0.74 and 13.94±1.15 N/cm² at 6 months and 1 year, respectively). In mice treated at 9 months (peak force of 21.28±1.49) and 21 months (peak force of 17.21±0.29) of age, a significant improvement was still seen in contractile function of treated diaphragms, 3 months post-treatment as compared to age-matched untreated controls (peak force of 12.71±0.94 at 2 years of age).

Ventilatory Function is Improved after Administration of rAAV2/1 Vectors to Adult Pompe Mice Using barometric plethysmography, multiple characteristics of ventilation in conscious, unrestrained mice were simultaneously measured. In this study, ventilation was measured under conditions of normoxia (normal breathing air oxygen levels; $F_1O_2$: 0.21, $F_fCO_2$: 0.00) and to assess the extended range of ventilatory capacity, under conditions of hypercapnia (higher than normal levels of carbon dioxide; $F_1O_2$: 0.93, $F_fCO_2$: 0.07).

Under conditions of normoxia, ventilation (the ratio of tidal volume/inspiratory time ($V_T$/Ti; mL/sec) (2.2±0.1 vs 1.79±0.16), the ratio of minute ventilation (mL/min) to expired $CO_2$ ($V_E$/$VCO_2$) (18.65±0.73 vs 13.3±0.74), and peak inspiratory flow (mL/sec) (4.11±0.17 vs 3.21±0.29)) were all improved (p<0.05) in mice treated at 3 months of age and tested at 6 months as compared to untreated age-matched controls. Correction of ventilatory function in normoxic conditions was not sustained though, as none of the parameters were significantly improved at one year of age (9 months post-treatment). Animals that were treated at 9 months and 21 months of age also did not show improved normoxic ventilation three months post-treatment. Conversely, hypercapnic respiratory challenge resulted in improved ventilatory function in all treated groups. As shown in FIG. 14A-FIG. 14D and FIG. 15A-FIG. 15D, for animals treated at 3 months and assayed at 6 months and 1 year of age as well as in animals treated at nine months and 21 months of age, minute ventilation (FIG. 14A-FIG. 14D) and peak inspiratory flow (FIG. 15A-FIG. 15D) were significantly increased over age-matched untreated control animals.

Figure 16:
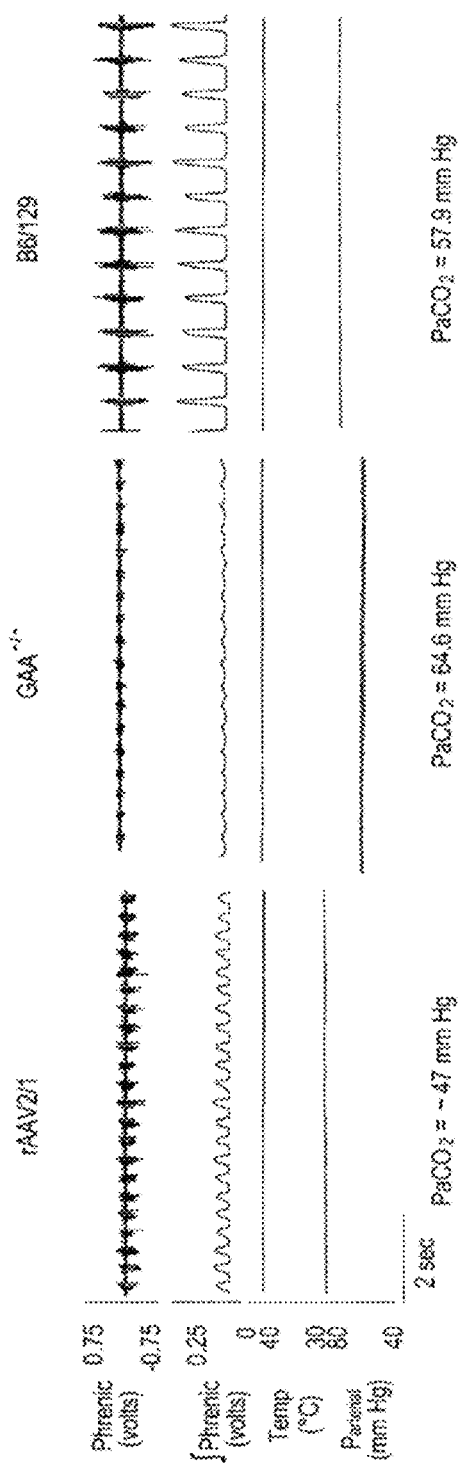
FIG. 16 is a schematic illustration of a Fuller Phrenic Burst Amplitude-Hybrid. The phrenic burst amplitude measured in volts describes the magnitude of the phrenic nerve with each respiration. The lower voltage in the GAA animals indicates defective phrenic motor neuron function. This figure shows restoration of phrenic output following AAV-GAA delivery to the diaphragm.

Increased Phrenic Nerve Activity after Gel-Mediated Delivery of rAAV2/1 to Gaa⁻/⁻ Mouse Diaphragm It was of interest to examine the phrenic nerve activity in an animal administered rAAV2/1 to the diaphragm muscle. As shown in FIG. 16, the inspiratory phrenic burst amplitude in a 2-year-old Gaa⁻/⁻ mouse administered rAAV2/1-CMV-hGAA via the gel method at 21 months of age was greater than that of an age-matched, untreated control animal, suggesting a possible correction of the potential neural deficits in Pompe disease.

Due to the physical nature of the mouse diaphragm (size and thickness), a gel-based method of vector delivery was used, rAAV2/1 vector could spread through the thickness of the diaphragm, whereas rAAV2 vector could only transduce the first few cell layers. The spread of vector may be attributed to the capsid conferring differential infection via cellular receptors and/or trafficking through the tissue via the process of transcytosis.

In this study, direct administration of rAAV2/1 vector to the diaphragm resulted in increased phrenic nerve activity in the treated animal as compared to an untreated control. Taken together these results indicate that physiological correction of diaphragm function can be mediated by rAAV2/1-based gene therapy and that even older animals as old as 21 months of age (note that the average lifespan of a wild-type C57BL mouse is approximately 2 years of age) can benefit from gene therapy treatment.

Example 7

Neural Deficits Contribute to Respiratory Insufficiency in a Mouse Model of Pompe Disease Respiratory dysfunction is a hallmark feature of Pompe disease and muscle weakness is viewed as the underlying cause, although the possibility of an associated neural contribution has not heretofore been explored. In the experiments described herein, behavioral and neurophysiological aspects of breathing in an animal model of Pompe disease—the Gaa⁻/⁻ mouse—and in a second transgenic line (MTP) expressing GAA only in skeletal muscle were examined. Glycogen content was significantly elevated in Gaa⁻/⁻ mouse cervical spinal cord, including in retrogradely labeled phrenic motoneurons. Ventilation, assessed via barometric plethysmography, was attenuated during both quiet breathing and hypercapnic challenge in Gaa⁻/⁻ mice (6 to >21 months of age) vs. wild-type controls. MTP mice had normal diaphragmatic contractile properties; however, MTP mice had ventilation similar to the Gaa⁻/⁻ mice during quiet breathing. Neurophysiological recordings indicated that efferent phrenic nerve inspiratory burst amplitudes were substantially lower in Gaa⁻/⁻ and MTP mice vs. controls. It was concluded that neural output to the diaphragm is deficient in Gaa mice, and therapies targeting muscle alone may be ineffective in Pompe disease.

Methods

Animals

The Gaa⁻/⁻ and muscle-specific hGAA (MTP) mice have been previously described (Raben et al., *Hum. Mol. Genet.*, 10:2039-2047, 2001; Raben et al., *J. Biol. Chem.*, 273: 19086-19092, 1998). Contemporaneous gender matched C57Bl/6×129X1/SvJ mice were used as controls for all experiments. Mice were housed at the University of Florida specific pathogen-free animal facility. The University of Florida's Institutional Animal Care and Use Committee approved all animal procedures.

Barometric Plethysmography

Barometric plethysmography to quantify ventilation (Buxco Inc., Wilmington, N.C.) has been described previously and was adapted for mice. Ventilation was characterized in male and female mice. Genders were separated only when significant differences were detected between male and female mice. Data from a subset of the animals used in these experiments have been reported as controls for a gene therapy intervention.

Hemoglobin, Hematocrit, Glucose and Sodium Blood Levels

Venous tail blood was collected from anesthetized mice (2% isoflurane, balance $O_2$) directly into a commercially available blood gas analyses cartridge (I-stat, Heska Corporation; Ft. Collins, Colo.).

Retrograde Labeling of Phrenic Motoneurons

The neuronal retrograde tracer Fluoro-Gold® (4%, Fluorochrome, LLC. Denver, Colo.) was applied to the peritoneal surface of the diaphragm (~75 μL) using a small artist's brush. Care was taken to apply the tracer sparingly only to the diaphragm in order to minimize leakage to liver and surrounding tissues. Forty-eight hours after Fluoro-Gold® application, the cervical spinal cord ($C_3$-$C_5$) was removed, paraffin-embedded and sectioned in the transverse plane at 10 μm. Fluoro-Gold®-labeled phrenic motoneurons were identified by fluorescence microscopy.

Statistics

Statistical significance for this project was determined a priori at $p<0.01$. Ventilation data were analyzed using a 3-way analysis of covariance (ANCOVA). Ratios of volume:bodyweight were not used, as body mass ratios can introduce bias and this method does not have the intended effect of removing the influence of body mass on the data. By using the ANCOVA method, bodyweight is analyzed as a co-variate for all respiratory volume data, which more accurately removes the influence of bodyweight on the data. For baseline measures, gender, strain and age were used as factors while the hypercapnic data was analyzed using gender, strain and time (minutes 1-10 of hypercapnia) as factors. Hemoglobin, hematocrit, glucose and sodium (anesthetized mice) were analyzed using the student's t-test. Glycogen quantification was analyzed using a 2-way ANOVA and t-test with Bonferroni correction for post-hoc measurements. Diaphragmatic muscle contractile function was analyzed using a 2-way ANOVA with repeated measures. Phrenic inspiratory burst amplitude, breathing frequency and the rate of rise of the phrenic burst were extracted from the phrenic neurogram. These variables and arterial $P_aCO_2$ were analyzed with the 1-way ANOVA and Fischer's LSD test for post-hoc analysis. All data are presented as the MEAN±SEM.

Arterial blood sampling, glycogen quantification, histological glycogen detection in motoneurons, in vitro diaphragmatic contractile properties, and efferent phrenic nerve recordings were performed as described (Martineau, L, and Ducharme, M. B., Contemp. Top. *Lab. Anim. Sci.*, 37(5): 67-72, 1998; Lo et al., *J. Appl. Physiol.*, 28:234-236, 1970; Guth, L, and Watson, P. K., *Exp. Neurol.*, 22:590-602, 1968: Staib et al., *Am. J. Physiol. Regul. Integr. Comp. Physiol.*, 282(3):R583-90, 2002: Doperalski, N.J. and Fuller, D. D., *Exp. Neurol.*, 200(1):74-81, 2006).

Results

General Features of $Gaa^{-/-}$ Mice $Gaa^{-/-}$ mice weighed significantly less than their wild-type controls at all ages. No age-related gender differences were observed, and males weighed significantly more than females at all ages.

Glycogen Quantification and PAS Staining of the Cervical Spinal Cord

Glycogen content was elevated at all ages in the cervical spinal cords ($C_3$-$C_5$) of $Gaa^{-/-}$ mice, and differences were more pronounced at >21 vs. 6 months (FIG. 17A). These data were confirmed in an independent series of experiments in which glycogen levels were determined in multiple levels of the neuraxis.

Correlative histochemistry also demonstrated significant glycogen reaction product in $Gaa^{-/-}$ mouse neuronal cell bodies throughout the gray matter of the cervical spinal cord that was especially prominent in motoneurons (FIG. 17E, FIG. 17F and FIG. 17G). Motoneurons in the ventral cervical spinal cord retrogradely labeled with Fluoro-Gold® exhibited prominent PAS droplets (positive glycogen) throughout the cell body cytoplasm (FIG. 17G). Comparable neurons from PAS-stained sections of control specimens showed neurons with virtually no PAS-positive inclusions (FIG. 17B, FIG. 17C and FIG. 17D).

Figure 18A:
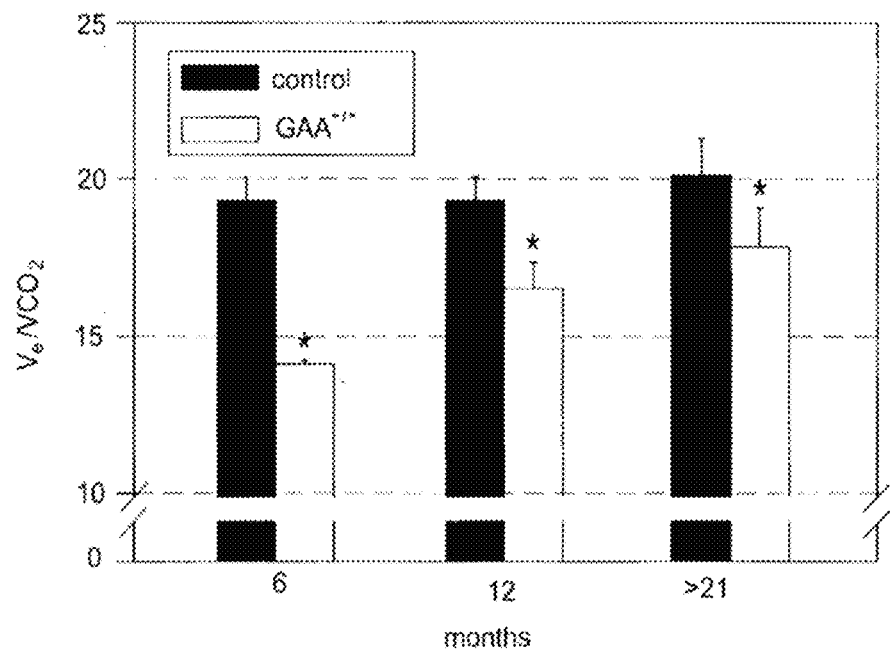
FIG. 18A and FIG. 18B are a pair of graphs showing age-dependent decline in minute ventilation. Control and GAA deficient mice were evaluated for Ve/VCO$_2$ (A) and minute ventilation (B) at 6, 12, >21 months. GAA KO mice have ½ normal Ve/VCO$_2$ and minute ventilation compared to controls.
Figure 18B:
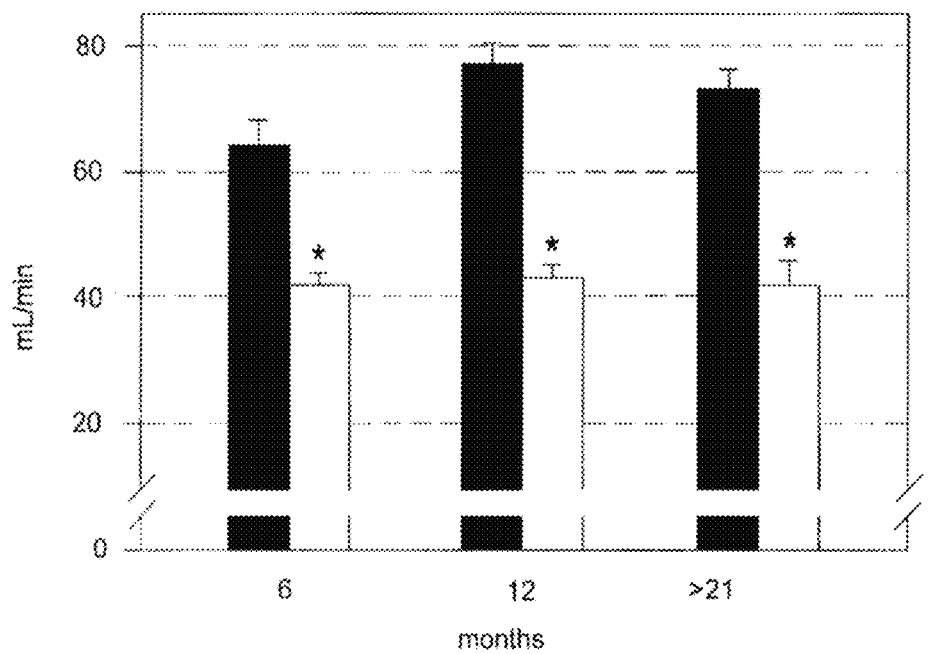

Ventilation $Gaa^{-/-}$ mice appeared to be hypoventilating based on the minute ventilation/expired $CO_2$ ratio, which normalizes minute ventilation to metabolic $CO_2$ production. This measure was attenuated at baseline in $Gaa^{-/-}$ mice vs. wild-type controls. Baseline minute ventilation (non-normalized), breathing frequency, tidal volume, peak inspiratory flow, peak expiratory flow and tidal volume/inspiratory time ratio were also decreased in $Gaa^{-/-}$ mice compared to controls at all ages studied (Table 2, FIG. 18). The only age differences detected were lower frequency at >21 months (vs. 6 months) and elevated tidal volume at >21 months (vs. 6 months). No strain by age interaction was detected in the analyses.

TABLE 2

Baseline Ventilation Characteristics

| | Frequency (breaths/min) | TV (mL/breath) | MV (mL/breath) | PIF (mL/sec) | PEF (mL/sec) | TV/T (mL/sec) |
|---|---|---|---|---|---|---|
| 6 month | | | | | | |
| Control: | 239 +/− 7 | 0.27 +/− 0.00 | 64.8 +/− 3.7 | 5.9 +/− 0.2 | 3.4 +/− 0.2 | 3.4 +/− 0.2 |
| $Gaa^{-/-}$: | 197 +/− 6* | 0.21 +/− 0.00* | 41.6 +/− 2.3* | 3.3 +/− 0.2* | 2.2 +/− 0.1* | 1.7 +/− 0.1* |
| 12 month | | | | | | |
| Control: | 252 +/− 7 | 0.31 +/− 0.00 | 77.3 +/− 3.4 | 6.7 +/− 0.2 | 4.4 +/− 0.2 | 3.9 +/− 0.2 |
| $Gaa^{-/-}$: | 186 +/− 7* | 0.23 +/− 0.00* | 43.2 +/− 2.3* | 3.6 +/− 0.1* | 2.3 +/− 0.1* | 2.1 +/− 0.1* |
| >21 month | | | | | | |
| Control: | 225 +/− 7€ | 0.33 +/− 0.00€ | 73.4 +/− 3.2 | 6.3 +/− 0.3 | 4.6 +/− 0.2 | 3.7 +/− 0.2* |
| $Gaa^{-/-}$: | 168 +/− 7*€ | 0.25 +/− 0.01*€ | 41.8 +/− 3.8* | 3.5 +/− 0.3* | 2.3 +/− 0.2* | 2.1 +/− 0.2* |

Sixty minute baseline (21% $O_2$, balanced $N_2$) values for frequency, tidal volume (TV), minute ventilation (MV), peak inspiratory flow (PIF), peak expiratory flow (PEF) and tidal volume: inspiratory time ratio (TV/Ti) of control and $Gaa^{-/-}$ mice.
* = $Gaa^{-/-}$ different from control ($p < 0.01$).
€ = > 21-month different from 6 months ($p < 0.01$).

Hypercapnic challenge was used as a respiratory stimulus to test the capacity to increase ventilation in $Gaa^{-/-}$ mice. The hypercapnic response was lower for $Gaa^{-/-}$ mice vs. controls at each age for minute ventilation (FIG. 18A and FIG. 18B), as well as frequency, tidal volume, peak inspiratory flow, peak expiratory flow and the tidal volume/inspiratory time ratio. Gender differences were detected only in the 6 month age group, whereby females had a different response to hypercapnia for all respiratory variables tested.

Blood Sampling

Both Hemoglobin (Hb) and Hematocrit (Hct) were elevated in $Gaa^{-/-}$ mice (Table 3), most likely to compensate for insufficient arterial partial pressure of $O_2$ ($P_aO_2$; see below). In addition, glucose and sodium levels did not vary between control and $Gaa^{-/-}$ mice, suggesting that the measured Hb and Hct differences did not reflect plasma volume differences. Gaa$^{-/-}$ mice had lower P$_a$O$_2$ vs. controls (Table 3), supporting the concept that these mice are hypoventilating.

TABLE 3

Blood Characteristics for 12 Month Gaa$^{-/-}$ and Control Mice

| | HEMOGLOBIN (g/dL) | HEMATOCRIT (%) | SODIUM (mmol/L) | GLUCOSE (mg/dL) | P$_a$O$_2$ (mmHg) |
|---|---|---|---|---|---|
| CONTROL: | 13.5 ± 0.3 | 39.8 ± 0.9 | 144.5 ± 0.8 | 180.4 ± 16.3 | 98.5 ± 1.9 |
| Gaa$^{-/-}$: | 15.3 ± 0.4* | 45.0 ± 1.1* | 143.4 ± 0.9 | 176.8 ± 11.4 | 83.3 ± 2.7* |

Hemoglobin, hematocrit, sodium and glucose values for control and Gaa$^{-/-}$ mice at 12 months of age (n = 9/group).
Arterial partial pressure of O$_2$ for control and Gaa$^{-/-}$ mice at 12 months of age (n = 6/group).
*= Gaa$^{-/-}$ different from control (p < 0.01).

Muscle-Specific hGAA Mice

Next, respiratory function in transgenic animals with muscle-specific correction of GAA activity (MTP mice) was quantified. To first obtain an index of diaphragm muscle function, in vitro contractile properties from B6/129, Gaa$^{-/-}$ and MTP mice were measured. Control and MTP mice had similar forces, while the Gaa$^{-/-}$ mice produced significantly smaller forces. These data confirm that the normal glycogen levels in MTP diaphragm muscle (MTP vs. B6/129; 1.7±1.3 vs. 1.4±0.2 μg/mgww) correspond to diaphragm muscle that is functionally similar to the B6/129 mice.

Figure 19A:
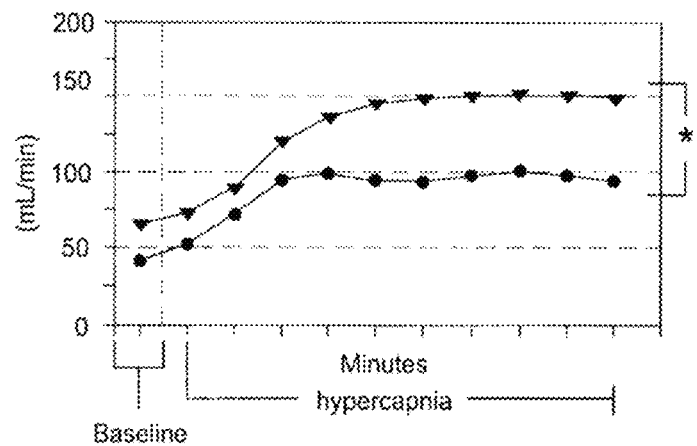
FIG. 19A, FIG. 19B and FIG. 19C illustrate Minute Ventilation Response to Hypercapnia. Minute ventilation of the 60 minute baseline (21% O$_2$, balanced N$_2$) and 10 minute response to hypercapnia (7% CO$_2$, balanced O$_2$) for 6 (FIG. 19A), 12 (FIG. 19B) and >21 (FIG. 19C) month old control and Gaa$^{-/-}$ mice. *=control different from Gaa$^{-/-}$, p<0.01.
Figure 19B:
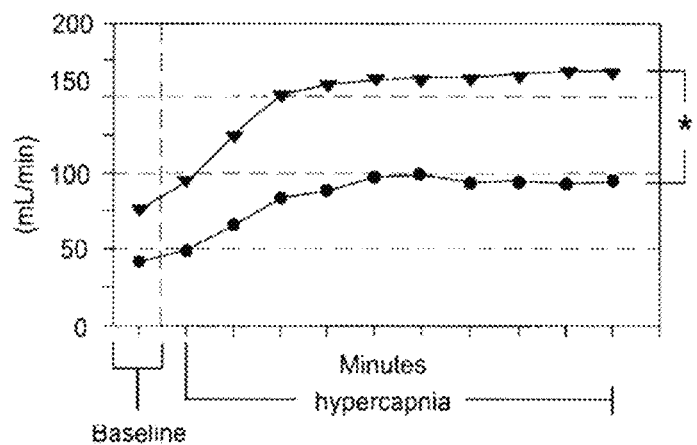
Figure 19C:
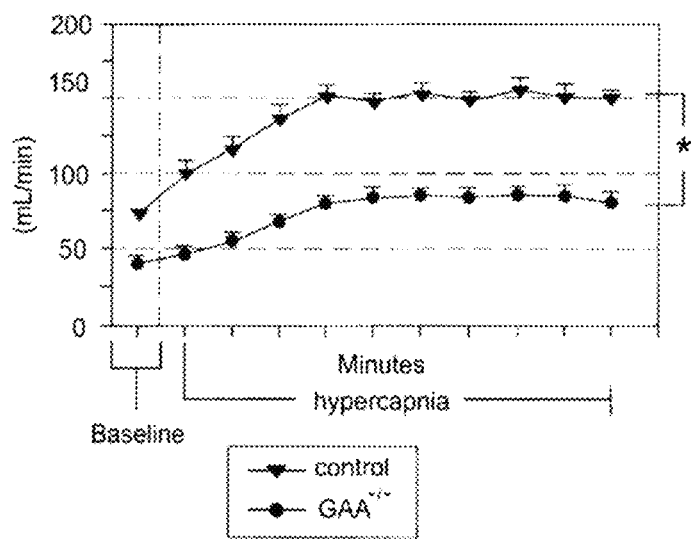

Despite apparently normal functional diaphragm muscle (FIG. 19C), the pattern of breathing was altered in the MTP mice. Minute ventilation during baseline was similar in MTP and Gaa$^{-/-}$ mice, and both were significantly reduced compared to B6/129 mice (FIG. 19A-FIG. 19C). Furthermore, the response to hypercapnia was attenuated in MTP mice, although they showed a greater response than the Gaa$^{-/-}$ mice (FIG. 19B). Representative airflow tracings from B6/129, Gaa$^{-/-}$ and MTP mice (FIG. 20C) were generated (FIG. 19C).

Efferent Phrenic Activity

Figure 20A:
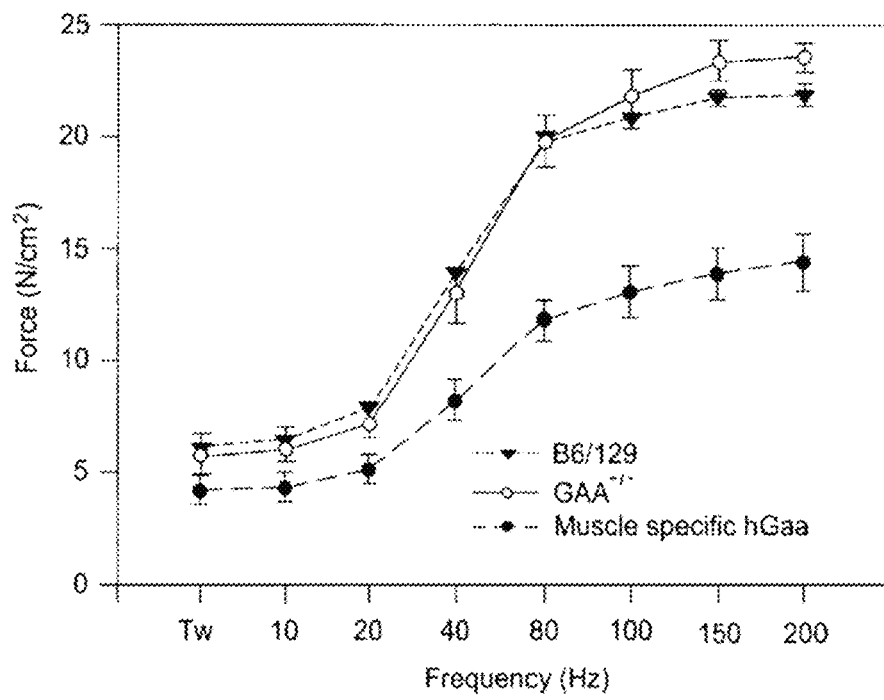
FIG. 20A and FIG. 20B are a pair of graphs.
Figure 20B:
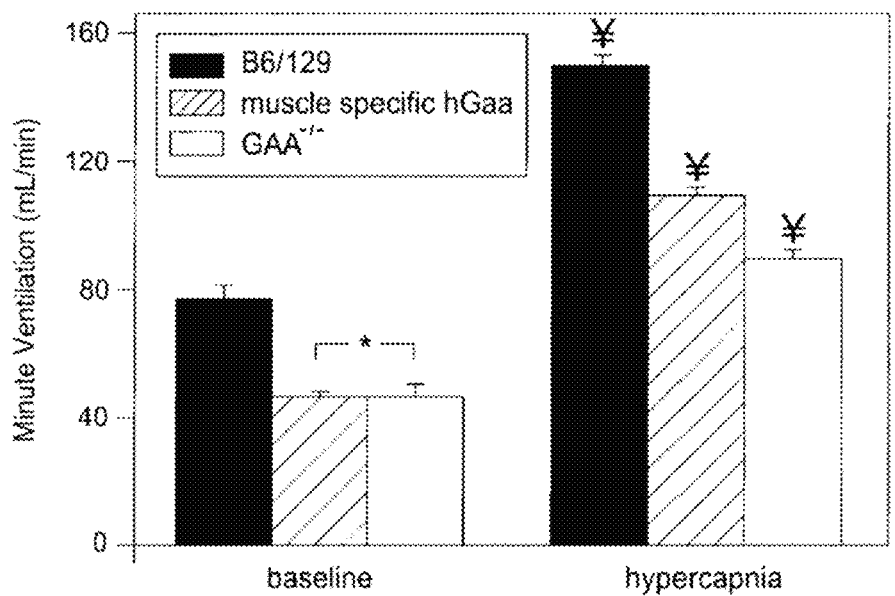
Figure 20C:
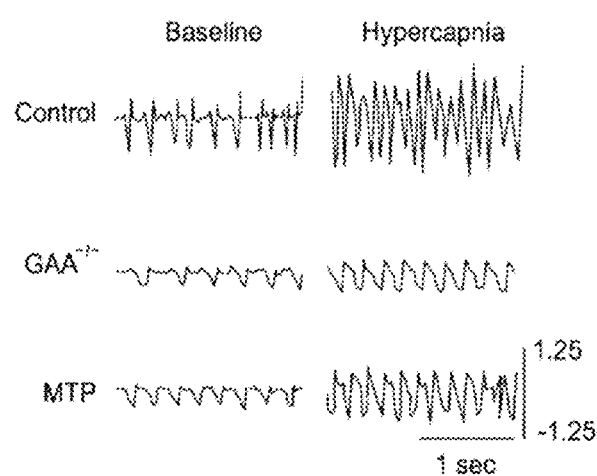
FIG. 20C is a series of tracings showing Muscle-Specific hGaa Mice. Force frequency measurements for B6/129 (n=3), Gaa$^{-/-}$ (n=3) and muscle specific hGaa mice (n=6) (FIG. 20A). †=Gaa$^{-/-}$ different from control and muscle specific hGaa mice. Minute ventilation at baseline and the mean response to hypercapnia for B6/129, Gaa$^{-/-}$ and muscle specific hGaa mice (n=8/group) (FIG. 20B). *=different from control, ¥=all groups different from each other. All values considered significant at p<0.01. Representative airflow tracings from un-anesthetized mice during quiet breathing (baseline) and respiratory challenge (hypercapnia) are provided in FIG. 20C. The scaling is identical in all panels. The airflow calibration is in mL/sec.

To determine whether the compromised ventilation seen in Gaa$^{-/-}$ and MTP was associated with reduced phrenic motor output, we measured efferent phrenic nerve activity in Gaa$^{-/-}$, MTP and control mice. At similar arterial PCO$_2$ levels (see legend, FIG. 20A), Gaa$^{-/-}$, and MTP mice had significantly lower phrenic inspiratory burst amplitudes (FIG. 20A and FIG. 20B). The neurogram recordings from Gaa$^{-/-}$ and MTP mice also revealed less frequent bursts, and an attenuated slope of the integrated inspiratory burst (i.e. slower "rate of rise", Table 4).

TABLE 4

Phrenic Neurophysiology Characteristics

| | Rate of Rise (mV/s) | Frequency (breaths/min) | Amplitude (mV) |
|---|---|---|---|
| Control: | 346 ± 86 | 167 ± 14 | 52.8 ± 14.1 |
| Gaa$^{-/-}$ | 44 ± 15* | 107 ± 14* | 6.6 ± 1.7* |
| MTP: | 101 ± 27* | 124 ± 17* | 11.8 ± 1.8* |

Rate of rise for the phrenic burst (mV/s), frequency of the phrenic burst (neural breaths/s) and amplitude of the phrenic burst (mV) for 12 month old control (n = 8), Gaa$^{-/-}$ (n = 8) and MTP (n = 6) mice.
*= different from control (p < 0.01)

Figure 21A:
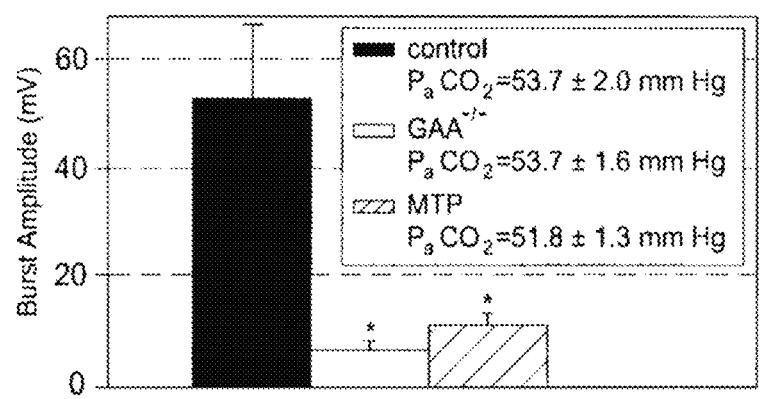
FIG. 21A is a graph and FIG. 21B is a series of tracings showing Phrenic Inspiratory Burst Amplitude. Thirty second mean phrenic inspiratory burst amplitude for control, Gaa$^{-/-}$ and muscle specific hGaa mice with similar arterial P$_a$CO$_2$ values (shown on graph). *=different from control, p<0.01. Raw phrenic amplitude (top traces) and rectified, integrated trace (bottom traces) from representative control, Gaa$^{-/-}$ and MTP mice are shown (scaling is identical in each panel).
Figure 21B:
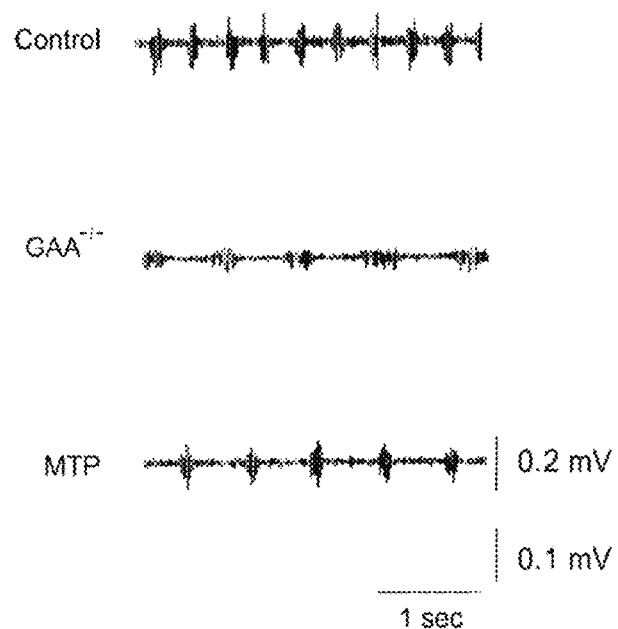

This study of a murine model of Pompe disease has revealed several observations pertaining to GAA-deficiency and concomitant respiratory involvement. First, ventilation is reduced in Gaa$^{-/-}$ mice as revealed by barometric plethysmography. Second, cervical spinal cord glycogen is elevated in Gaa$^{-/-}$ mice, and PAS staining identified prominent glycogen inclusions in cervical motoneurons, including phrenic motoneurons indirectly identified by retrograde Fluoro-Gold® tracing. Third, Gaa$^{-/-}$ mice have attenuated phrenic output relative to wild-type controls. Lastly, MTP mice also exhibit breathing impairments and phrenic neurogram features similar to those observed in Gaa$^{-/-}$ mice, despite apparently normal diaphragmatic contractile function (FIG. 21A and FIG. 21B). These are the first formal lines of evidence suggesting respiratory weakening in the Gaa$^{-/-}$ mouse, and by extrapolation in Pompe disease patients, may be the result of a combination of both neural and muscular deficits.

Excess glycogen within the spinal cord (including phrenic motoneurons) led to the quantification of inspiratory phrenic burst amplitude between control and Gaa–/– mice in the experiments described herein. Phrenic nerve activity, which is the final motor output of the respiratory system, was measured. The mechanisms responsible for the reduced output in Gaa$^{-/-}$ mice could stem from areas beyond the phrenic motoneurons, which include higher (neural) respiratory inputs and/or impairment of chemosensory afferents due to chronically attenuated P$_a$O$_2$ levels and the hypothesized elevated PaCO$_2$ levels. However, it should be noted that during conditions of higher respiratory drive (PaCO$_2$–90 mmHg) both groups were able to increase phrenic inspiratory burst amplitude, but the Gaa$^{-/-}$ mice continued to have lower output (control: 68.7 mv±20.0, Gaa$^{-/-}$; 14.0 mv±4.8). The final end product of the phrenic nerve activity was altered in Gaa$^{-/-}$ mice thus demonstrating a neural deficit of respiratory control.

To determine that muscular dysfunction was not the only contributor to ventilation deficits due to GAA deficiency, a double transgenic mouse that expressed hGAA only in skeletal muscle (maintained on the Gaa$^{-/-}$ background) was used. Since these mice had normal muscle contractile properties, it was hypothesized that any differences in ventilation between MTP and control strains would reflect disparity in the neural control of respiratory muscles. Consistent with this postulate, ventilation was similar between MTP and Gaa$^{-/-}$ mice during quiet breathing. When respiratory drive was stimulated with hypercapnia, the ventilatory response of MTP mice was still less than that of controls, but elevated compared to Gaa$^{-/-}$ mice. Thus, both muscle and neural components contribute to ventilation deficits under conditions of elevated respiratory drive.

Example 8

Figure 22:
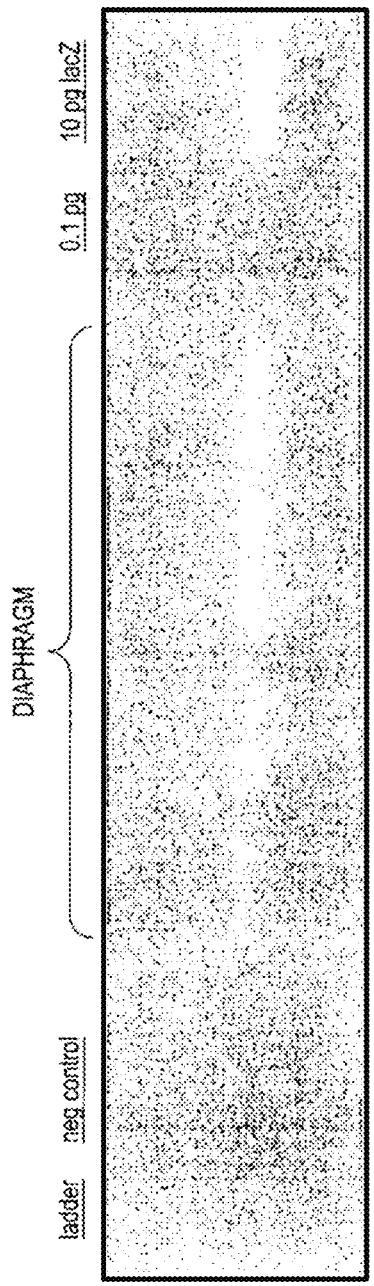
FIG. 22 is a photograph of an agarose gel showing that genomic DNA isolated from diaphragm contains control gene post-vector delivery.
Figure 23:
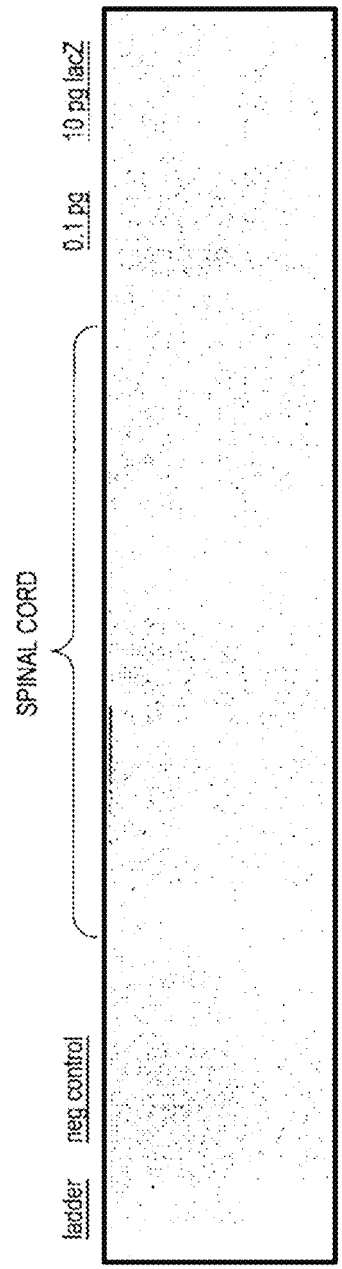
FIG. 23 is a photograph of a gel showing that genomic DNA isolated from the phrenic nucleus.
Figure 24:
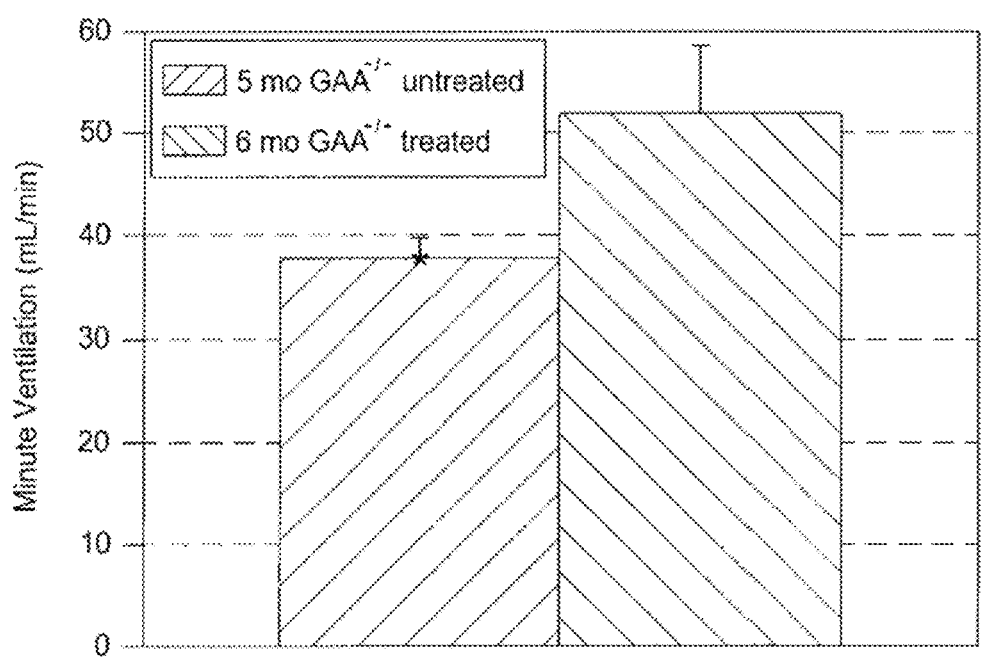
FIG. 24 is a graph showing that ventilation is improved 4 weeks post-injection with AAV-CMV-GAA (2.52×10$^{10}$ particles).

AAV Administered to Muscle is Able to be Transported to the Motor Nerve Body Via the Synapse with the Muscle Fiber Referring to FIG. 22, FIG. 23 and FIG. 24, AAV administered to muscle is able to be transported to the motor nerve body via the synapse with the muscle fiber. In experiments in which mice received intrathoracic injection of AAV-CMV-LacZ ($2.18 \times 10^{11}$ particles) (FIG. 22), genomic DNA isolated from diaphragm contains control gene post vector delivery. In experiments in which mice received intrathoracic injection of AAV-CMV-LacZ ($2.18 \times 10^{11}$ particles), (FIG. 23), genomic DNA was isolated from the phrenic nucleus. FIG. 24 shows that ventilation is improved 4 weeks post-injection with AAV-CMV-GAA ($2.52 \times 10^{10}$ particles).

Example 9

Restoration of the Neuromuscular Junction Integrity with rAAV2/9 Vectors

In developing therapies for muscular dystrophies, there exists the unique challenge of achieving simultaneous widespread correction of all affected tissues.

Figure 25:
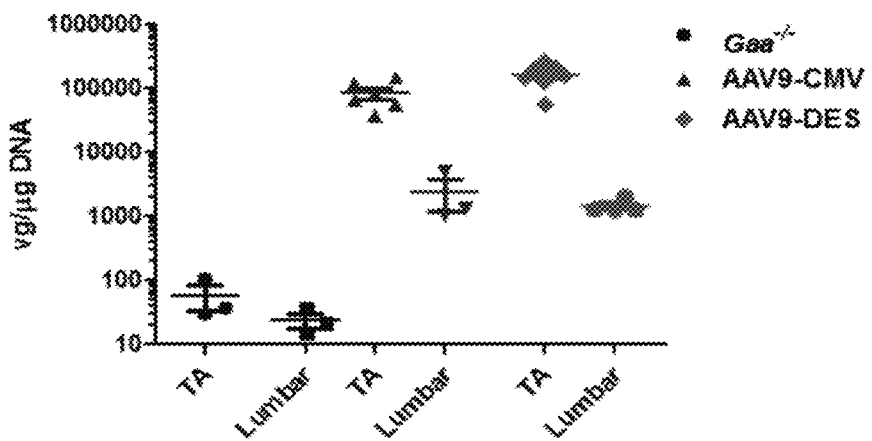
FIG. 25 shows vector genome copies in the tibialis anterior (TA) and lumbar spinal cord after direct intramuscular injection of genome copies of AAV2/9-GAA into Gaa$^{-/-}$ animals. Briefly, Gaa$^{-/-}$ animals received a single injection of AAV2/9-DES-GAA or AAV2/9-CMV-GAA vectors in the tibialis anterior muscle. Vector genome copies were assessed in the tibialis anterior and lumbar spinal cord 28 days post-injection. Both constructs demonstrate efficient transduction of skeletal muscle and retrograde transport of the therapeutic transgene.

This Example shows that the rAAV2/9 vector encoding hGAA results in retrograde transport of the transgene (human GAA) to motor neurons, as well as effective transduction of skeletal muscles, CNS, and cardiac tissues (FIG. 25). In addition, the administration of rAAV2/9-GAA vectors result in restoration of neuromuscular junction integrity, and the reversal of axonal pathology in Pompe disease. The restoration of adequate GAA levels in motor neurons provides significant improvement in ventilatory parameters of Pompe animals.

(A) Direct Intramuscular or Intraspinal Injection

Briefly, one-year-old Pompe mice ($Gaa^{-/-}$) were randomized to the following groups: untreated ($Gaa^{-/-}$), AAV2/9-CMV-hGAA, or AAV2/9-DES-hGAA. AAV2/9-treated animals received a single intramuscular injection of $1 \times 10^{11}$ vg of vectors in the right tibialis anterior muscle. One month post injection, the tibialis anterior muscle and lumbar spinal cord were analyzed for vector genome copy number and GAA activity.

Figure 26A:
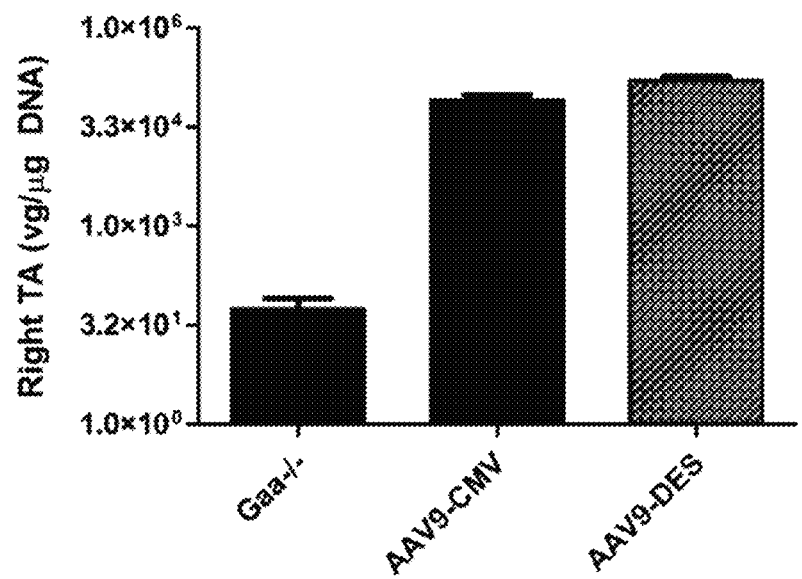
FIG. 26A, FIG. 26B and FIG. 26C show-vector genome copy and GAA enzyme activity in Pompe animals following a single injection of AAV2/9-hGAA in the tibialis anterior muscle. Vg copies in the tibialis anterior (FIG. 26A) and (FIG. 26B) lumbar spinal cord at one month post-injection are shown. PCR data indicates sufficient retrograde transduction of AAV vectors in the spinal cord.
Figure 26B:
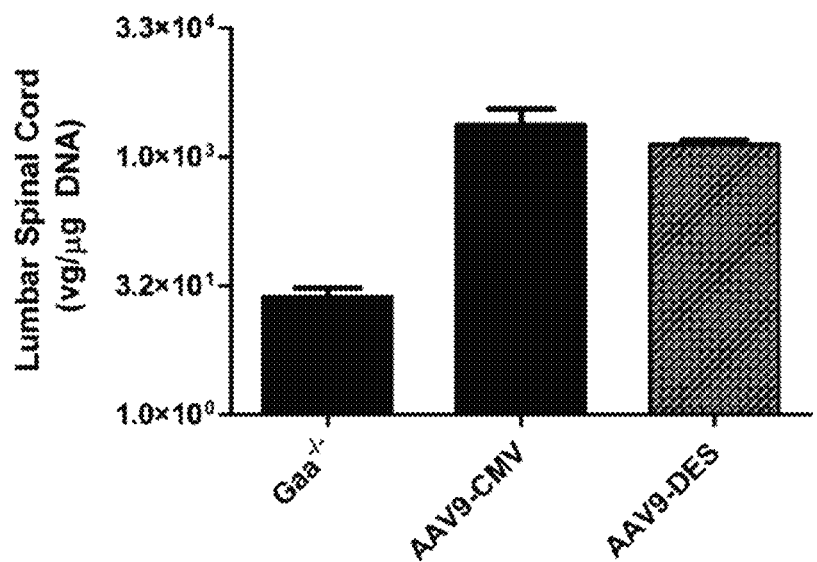
Figure 26C:
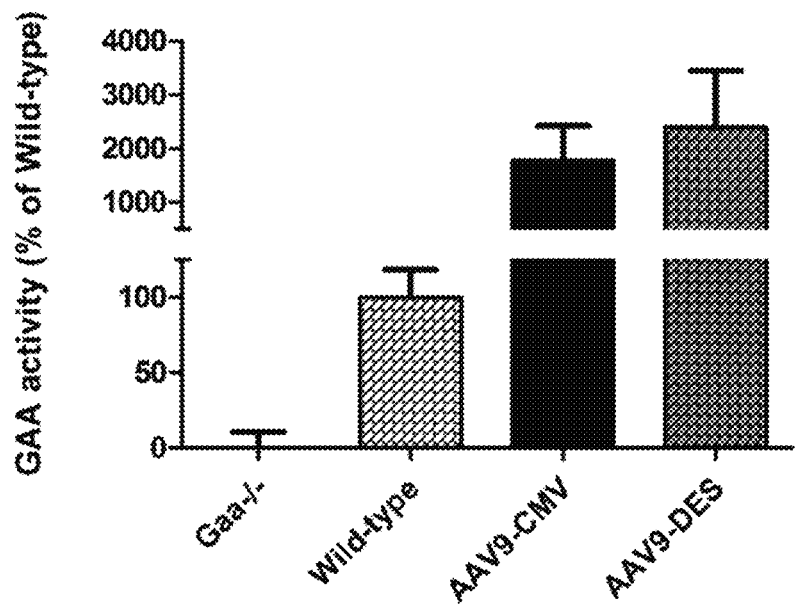
Figure 27:
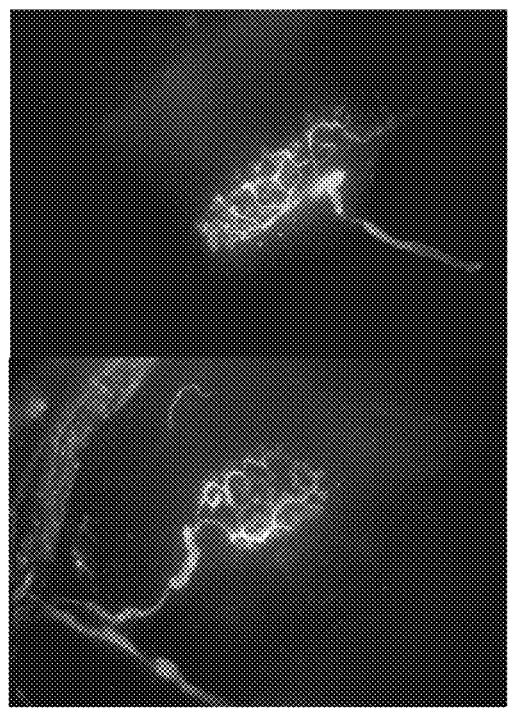
FIG. 27 shows staining of neuromuscular junction (NMJ) following a single injection of AAV2/9-DES-hGAA in the tibialis anterior. Immunostaining of the NMJ shows that rAAV2/9 mediated delivery of hGAA results in the reversal of pathology of Pompe disease and restoration of the NMJ in treated Gaa$^7$ animals.

As shown in FIG. 26, high levels of vector genomes were detected in the tibialis anterior (AAV2/9-DES-hGAA $1.5 \times 10^5 \pm 3.1 \times 10^4$ vg/ug DNA; AAV2/9-CMV-hGAA $8.4 \times 10^4 \pm 1.7 \times 10^4$ vg/ug DNA) and lumbar spinal cord (AAV2/9-DES-hGAA $1.5 \times 10^3 \pm 1.7 \times 10^2$ vg/ug DNA; AAV2/9-CMV-hGAA $2.5 \times 10^3$: $1.3 \times 10$ vg/ug DNA), indicating efficient transduction of skeletal muscle and retrograde transport of AAV2/9 vectors. Activity of GAA in tibialis anterior lysates was 2396% and 1770% above wild-type in AAV2/9-DES-hGAA and AAV2/9-CMV-hGAA animals, respectively ($p<0.05$). Immunohistochemical assessment of neuromuscular junctions in the tibialis anterior revealed a restoration of integrity in AAV2/9-treated animals (FIG. 27).

In this Experiment, the tissue-specific expression of the transgene (GAA) is compared between the traditional CMV promoter and the more tissue-restricted Desmin (DES) promoter. Briefly, the human desmin construct described in the experiments (AAV2/9-DES) contains both a myocyte specific enhancer factor 2 (MEF2) and a MyoD enhancer element. Analysis of human tissues revealed desmin expression in cerebellum, endometrium, skeletal muscle, neuronal cells of the lateral ventricle and heart. This is advantageous for AAV constructs as Desmin serves as a non-viral and tissue-restricted promoter compared to the traditional CMV promoter (viral, ubiquitous cellular expression). In addition, expression profiles from the spinal cord also show that Desmin is expressed, making it a favorable promoter for driving therapeutic transgenes by AAV vectors.

Enzymatic activity assays for GAA 28 days postinjection demonstrate significant enzyme levels and vector genome copies in the TA and lumbar spinal cord (FIG. 25). Direct administration of AAV2/9 to skeletal muscle results in efficient transduction of the injected muscle and displays retrograde transduction of lumbar motor neurons as shown by evidence of vector genome copies in the lumbar spinal cord region, as well as restoration of neuromuscular junction (NMJ) integrity in $Gaa^{-/-}$ animals. The results also show that intramuscular delivery of rAAV vectors transduces CNS and skeletal muscle tissues, and thus, can be used to treat the CNS and skeletal muscle components of Pompe disease.

Materials and Methods

Packaging and Purification of Recombinant AAV2/9 Vector.

Recombinant AAV particles based on serotype 9 were produced using p43.2-GAA and were generated, purified, and titered at the University of Florida Powell Gene Therapy Center Vector Core Lab.

Experimental Animals.

The exon 6 GAA knockout animal model, which represents the cardiac and skeletal muscle phenotype associated with Pompe disease, was used to examine the transduction efficiency of AAV2/9-mediated GAA (AAV2/9-GAA) therapy and vector construct specificity.

$Gaa^{-/-}$/129SvE ($Gaa^{-/-}$) mice were injected with either 20 μl of lactated ringer's solution or with $1 \times 10^{11}$ vg rAAV2/9-CMV-GAA or rAAV2/9-DES-GAA diluted in lactated ringer's solution (QS 20 μl).

Whole Mount Neuromuscular Junction.

Skeletal muscles were dissected and incubated in α-bungarotoxin (TRITC labeled) for 10 minutes. Washed and fixed in 4% paraformaldehyde. Tissues were blocked in 4% BSA (1% TritonX) and incubated with NFH. Secondary antibodies (Alexa 488) directed against NFH were performed and tissues were mounted for subsequent microscopy.

Sciatic Nerves.

Sciatic nerves were isolated and placed in cassettes for OCT fixation. Sections were cut at 5 microns and subjected to primary and secondary Ab incubation with NFH, MBP, SMI-32 or H & E visualization.

Genomic DNA Extraction and Real-Time PCR.

PCR was used to measure distribution of AAV genomes following intramuscular injection in the TA and lumbar spinal cord. DNA was isolated using the DNAeasy kit (Qiagen) according to manufacturer's instructions. Primers and probes were designed to the SV40 poly-A region of the AAV vector.

GAA Activity Assay.

Tissues were harvested, immediately snap frozen and stored at $-80°$ C. Homogenates were centrifuged at 14,000 rpm for 10 minutes at $4°$ C. The resulting supernatant was assayed for GAA activity by measuring the cleavage of 4-methylumbelliferyl-α-Dglucopyranoside after incubation for 1 hour at $37°$ C. Protein concentration was measured using the Bio-Rad DC protein assay kit per manufacturer's instructions. Data are expressed relative to values measured in untreated GAA tissue levels (% WT).

(B) Direct Intraspinal Administration

To directly transduce the cervical cord region and phrenic motor neuron pool, rAAV-GAA vectors were administered into the C3-C5 region of the spinal cord of the $Gaa^{-/-}$ mice via direct intraspinal injection.

Figure 28A:
FIG. 28A and FIG. 28B show transduction of phrenic motor neuron pool after direct intraspinal injection of AAV reporter constructs in mouse C3-C5 region.
Figure 28B:
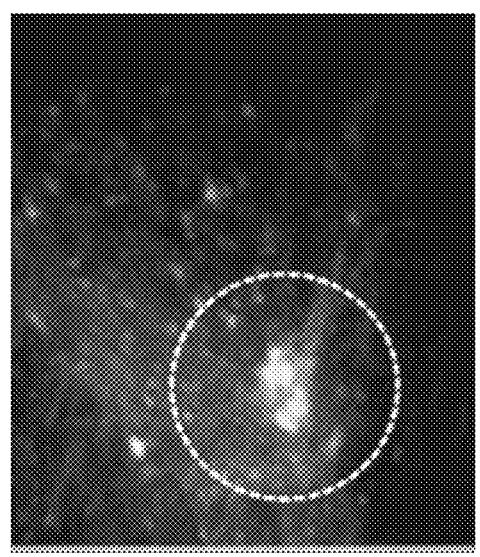
Figures 29A, 29B:
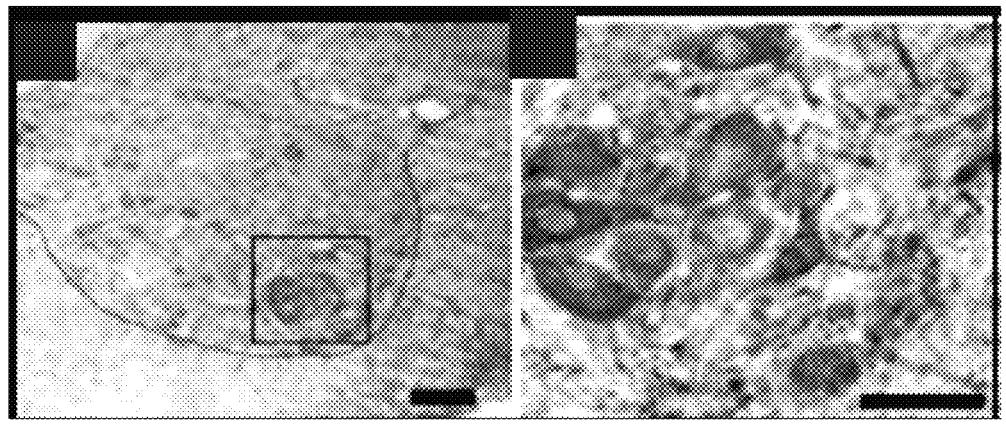
FIGS. 29A and 29B show immunohistochemistry detection of GAA protein expression in phrenic motor neuron pool after direct intraspinal injection of AAV-GAA in the mouse C3-C5 region. Detection of AAV-GAA in the phrenic motorneuron pool is shown (FIG. 29A) at low and (FIG. 29B) at higher magnification. Dark brown staining is positive for GAA protein detection.

As shown in FIG. 28, direct injection of rAAV2/9 reporter constructs in mouse C3-C5 region resulted in transduction of the phrenic motor neuron pool. Delivery of the therapeutic transgene (GAA) in $Gaa^{-/-}$ animals significantly improved respiratory function, and the expression of GAA in the phrenic motor neuron pool was confirmed via immunohistochemical detection (FIG. 29). The observation of increased respiratory function was the result of CNS transduction alone, as vector genome copies were not detected in the diaphragm. The results also show that glycogen accumulation in the CNS impairs skeletal muscle function.

(C) Direct Intrathoracic Administration

Figure 30:
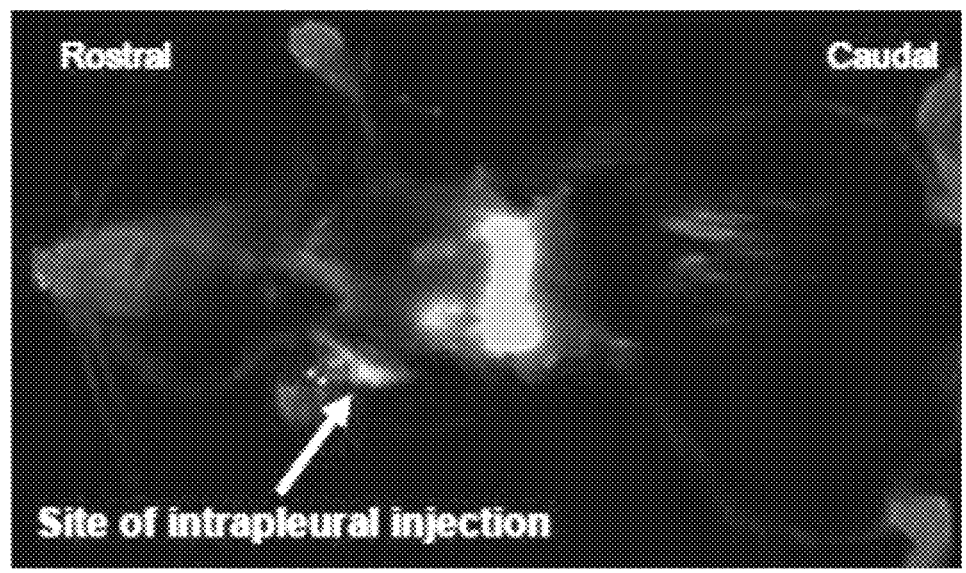
FIG. 30 shows intrathoracic injection of infrared dye in mouse. Imaging indicates positive detection of the dye across the surface of the diaphragm.

With the observation that expression of GAA in the CNS vastly improves respiratory muscle function, experiments were conducted to target both respiratory muscle (e.g., diaphragm and costal) and the CNS (cervical and thoracic regions) (FIG. 30). In these experiments, AAV2/9-CMV-GAA was compared to AAV2/9-DES-GAA to examine the retrograde efficiency of the DES promoter in the CNS.

Briefly, $Gaa^{-/-}$ animals received a single injection of either the AAV2/9-CMV-GAA or AAV2/9-DES-GAA vectors. The administration of AAV2/9-DES-GAA resulted in similar or superior transduction efficiency of target tissues when compared to AAV2/9-CMV-GAA, and resulted in improvement in cardiac and respiratory function.

Intrathoracic injection in $Gaa^{-/-}$ animals resulted in detection of vector genomes in the diaphragm and in the C3-C5 region of the spinal cord (phrenic motor neuron region). The results show that a retrograde transport phenomenon occurs with the use of AAV2/9 vectors.

Figure 31:
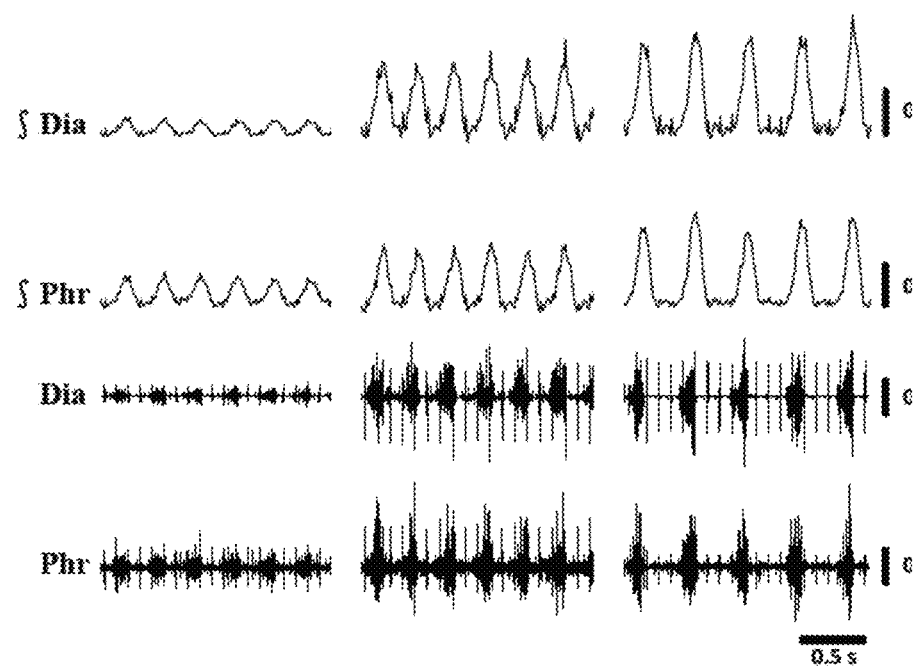
FIG. 31 shows diaphragm and phrenic motor neuron activity during hypercapnic conditions after intrathoracic injection of AAV vectors. Untreated Gaa$^{-/-}$ animals show a weak and blunted EMG (diaphragm) and burst amplitude (phrenic nerve) compared to AAV2/9-CMV-GAA and AAV2/9-DES-GAA treated animals.

To determine the physiological implications of transduction of both respiratory muscle and the CNS, $Gaa^{-/-}$ animals received a single intrathoracic injection of AAV2/9-CMV-GAA or AAV2/9-DES-GAA, and were subjected to neurophysiological measurements 6 months post-injection. Direct in situ measurement of the phrenic nerve revealed an apparent therapeutic effect by evidence of increased burst amplitude during hypercapnic conditions and diaphragm EMG activity (FIG. 31).

In addition, experiments were conducted to determine whether retrograde transport is evident in the phrenic motor neuron pool, which has a significant impact on proper respiratory function. One of the hallmarks of Pompe disease is respiratory insufficiency. Although respiratory insufficiency is traditionally thought to be the result of respiratory muscle weakness, the present inventors discovered that respiratory insufficiency could result from impairment in the activation of the phrenic nerve due to glycogen accumulation.

To directly visualize AAV-mediated retrograde transduction in the phrenic motor neuron pool, AAV2/9-GFP vectors were injected to $Gaa^{-/-}$ animals via intrathoracic injections. One month following injection, animals were perfused and the entire spinal cord was fixed for cross-sectional immunohistochemical analysis for detection and localization of GFP expression.

Figure 32:
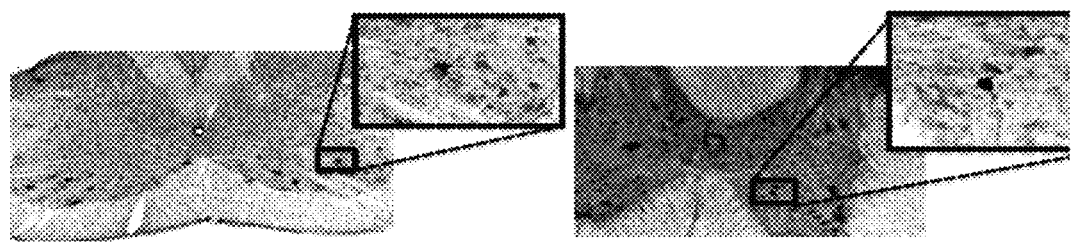
FIG. 32 shows detection of AAV-reporter in the cervical and thoracic spinal cord. Anti-GFP immunohistochemical staining detects positive phrenic (left) and costal (right) motor neuron staining demonstrating intrathoracic administration of AAV2/9 results in retrograde transduction.
Figure 33A:
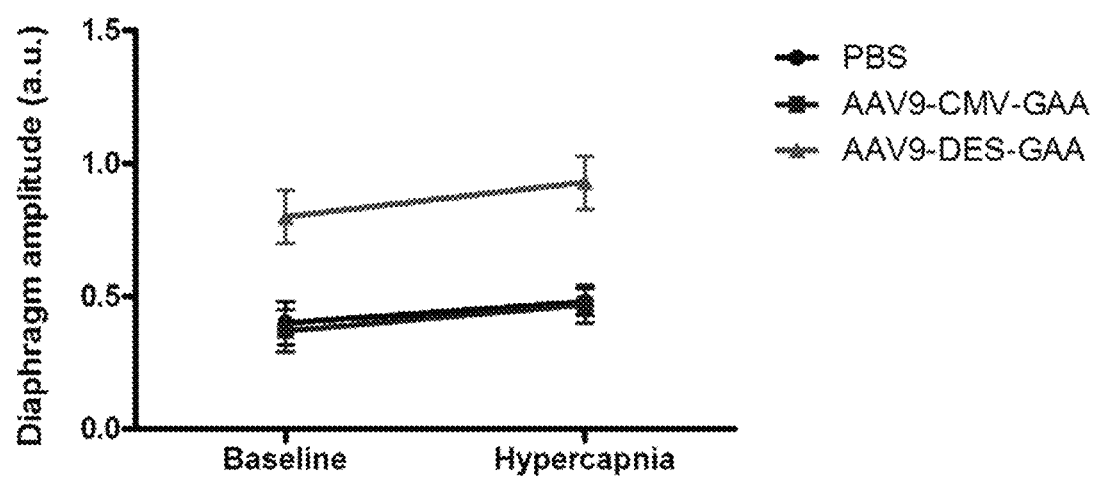
FIG. 33A, FIG. 33B and FIG. 33C show diaphragm EMG (FIG. 33A), copies of AAV genome vectors (FIG. 33B), and improvement in phrenic nerve signal propagation (FIG. 33C) following intrathoracic administration of rAAV2/9-CMV-GAA or rAAV2/9-DES-GAA vectors into Gaa$^{-/-}$ animals.
Figure 33B:
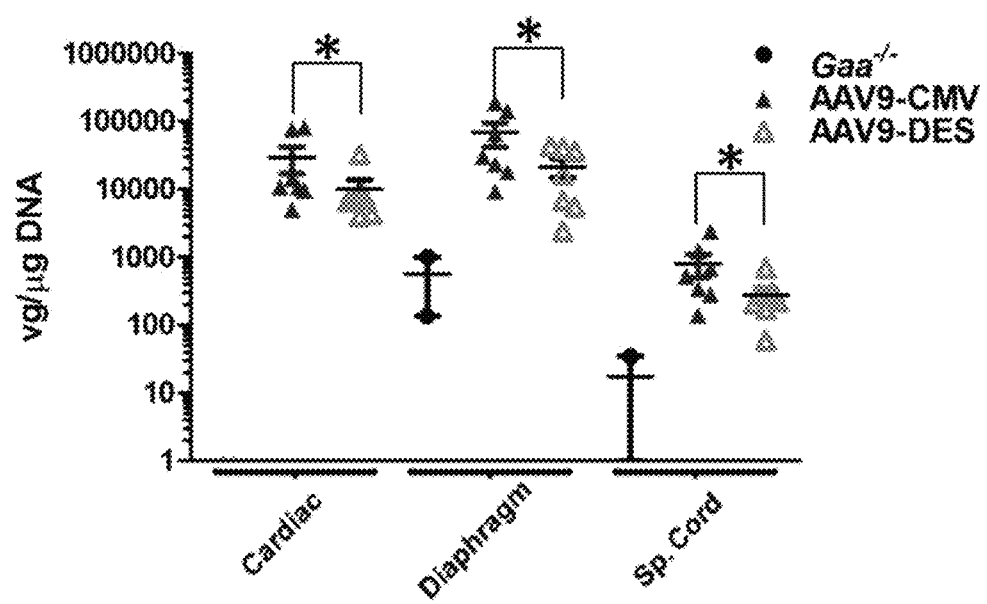
Figure 33C:
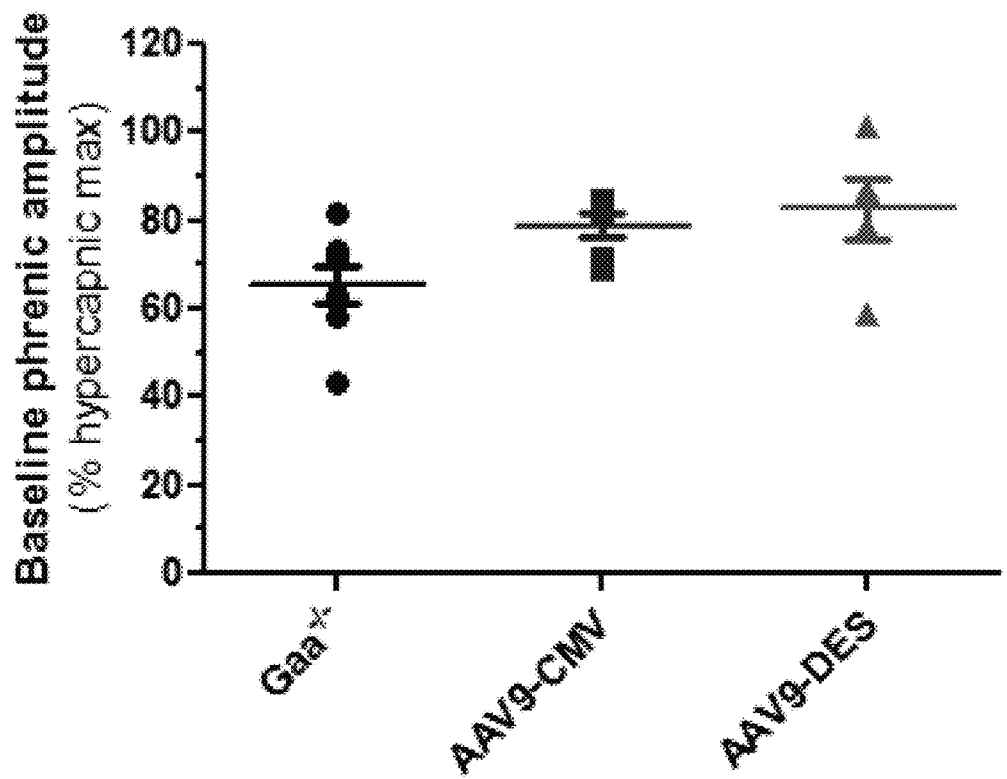

As shown in FIG. 32, positive staining for GFP was detected in the C3-C5 and T2-T5 regions of the spinal cord. The inset in each area is indicative of positive staining for the phrenic (left) and costal (right) motor pool, respectively. FIG. 33 shows that the administration of rAAV-CMV-GAA and rAAV-DES-GAA improves phrenic nerve signal propagation.

(D) Intravenous Administration

Intravenous administration of rAAV-GAA vectors provides treatment of Pompe disease, including correction of cardiac and respiratory muscle dysfunction. Briefly, $4\times10^8$ vg of rAAV2/9-CMV-hGAA vectors were administered to one-day-old $Gaa^{-/-}$ mice via intravenously (IV) injection. Assessment of cardiac measurements (e.g., P-R interval, cardiac output, and ejection fraction) revealed a significant improvement in treated $Gaa^{-/-}$ mice as compared to untreated animals out to 6 months post-injection. Additionally, as a result of restored GAA activity, glycogen deposition was dramatically reduced in cardiac and diaphragm tissues of the treated animals.

Figure 34A:
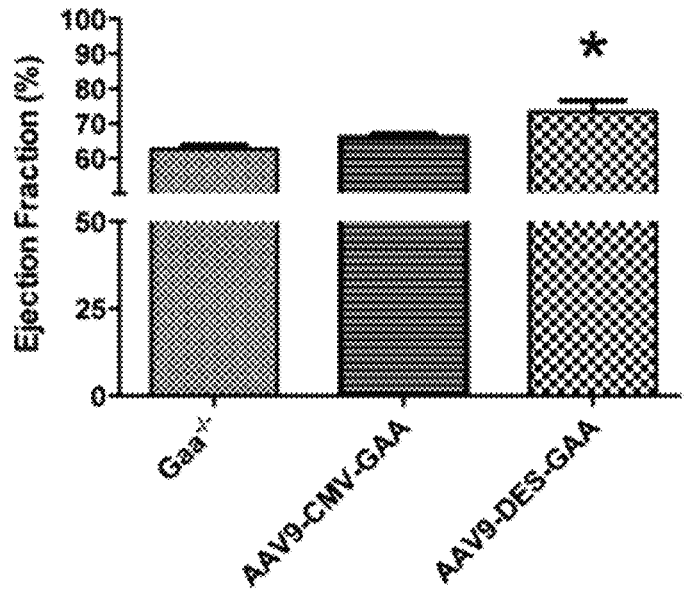
FIG. 34A, FIG. 34B, FIG. 34C, FIG. 34D, FIG. 34E, FIG. 34F, FIG. 34G, FIG. 34H and FIG. 34I show correction of pathological symptoms in Gaa$^{-/-}$ animals after intravenous administration of AAV2/9-CMV-GAA or AAV2/9-DES-GAA vectors.
Figure 34B:
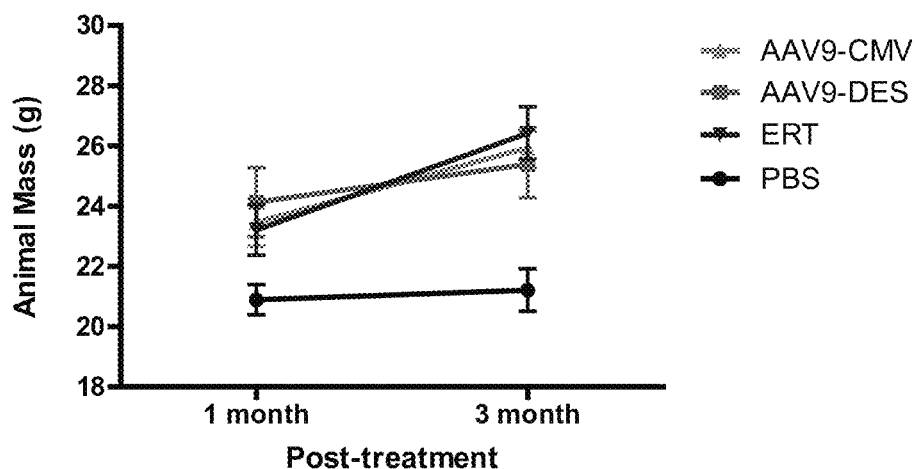
Figure 34C:
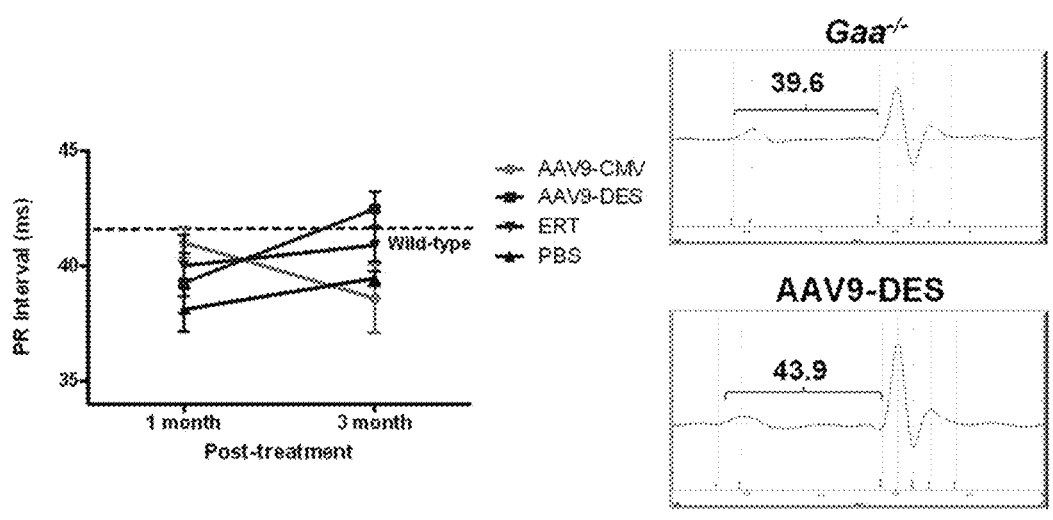
Figure 34D:
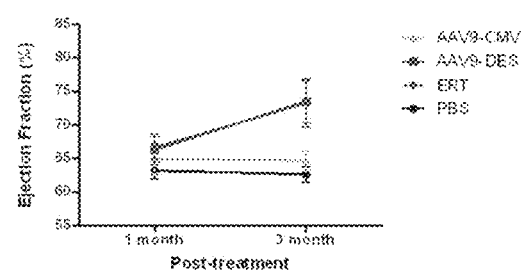
Figure 34D:
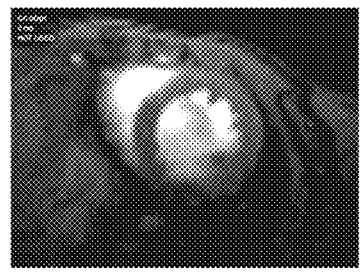
Figure 34D:
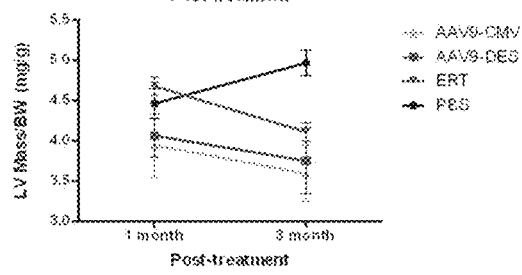
Figure 34E:
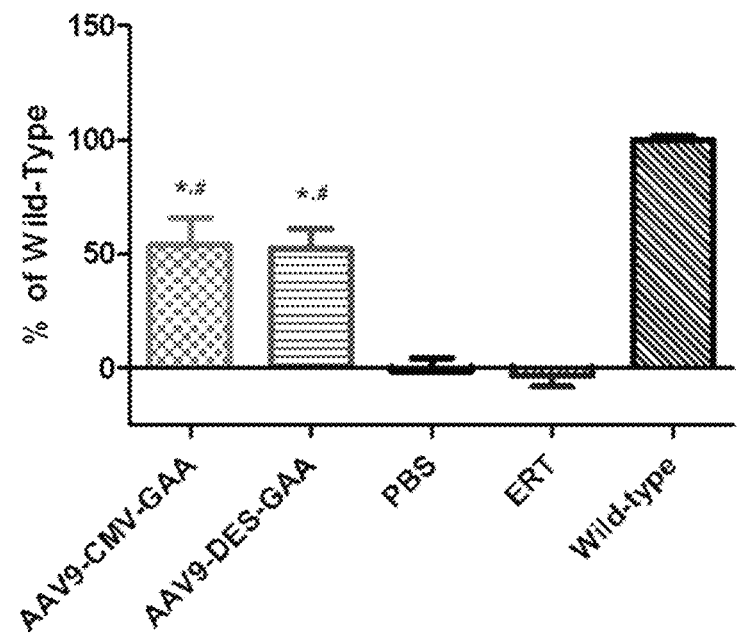
Figure 34F:
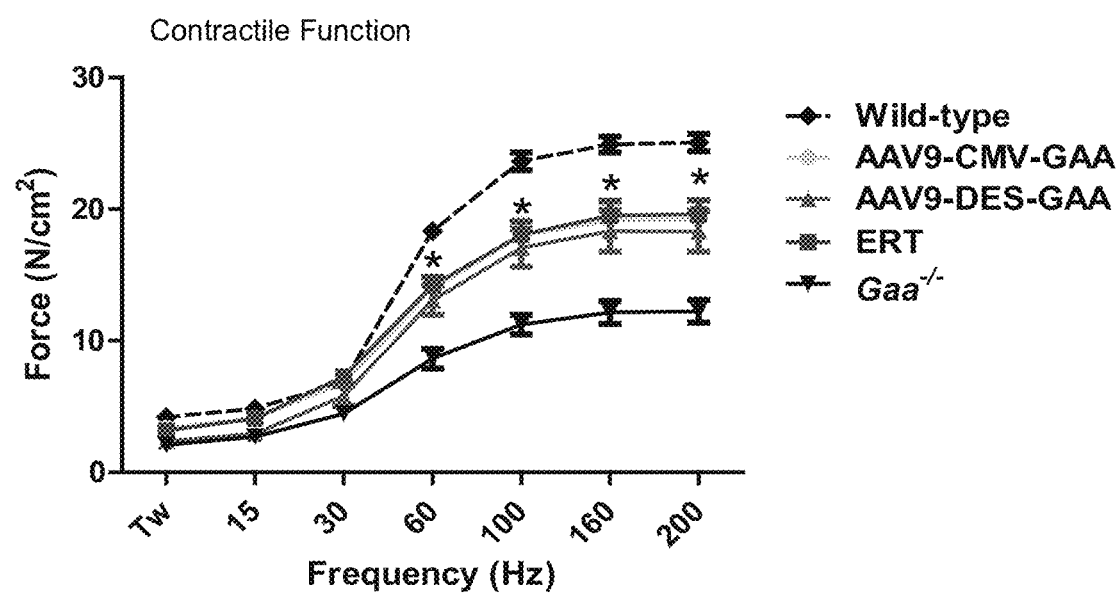
Figure 34G:
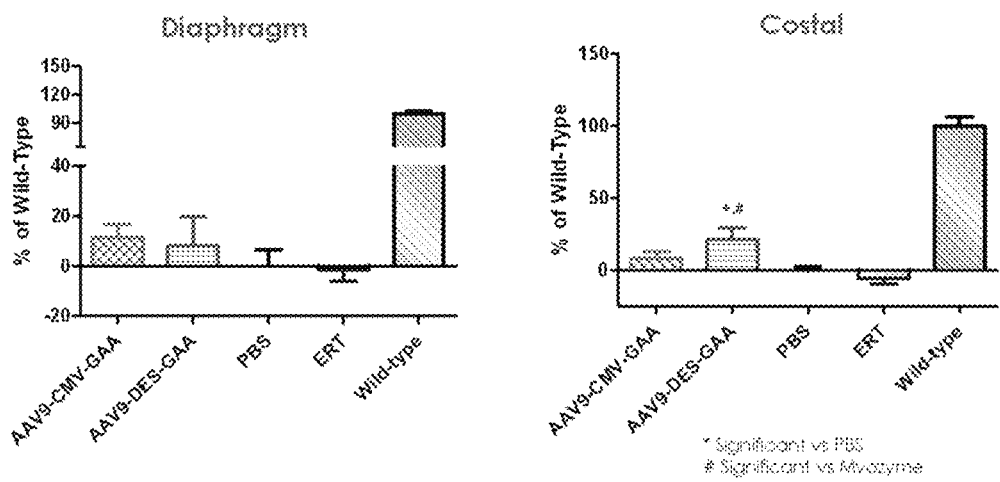
Figure 34H:
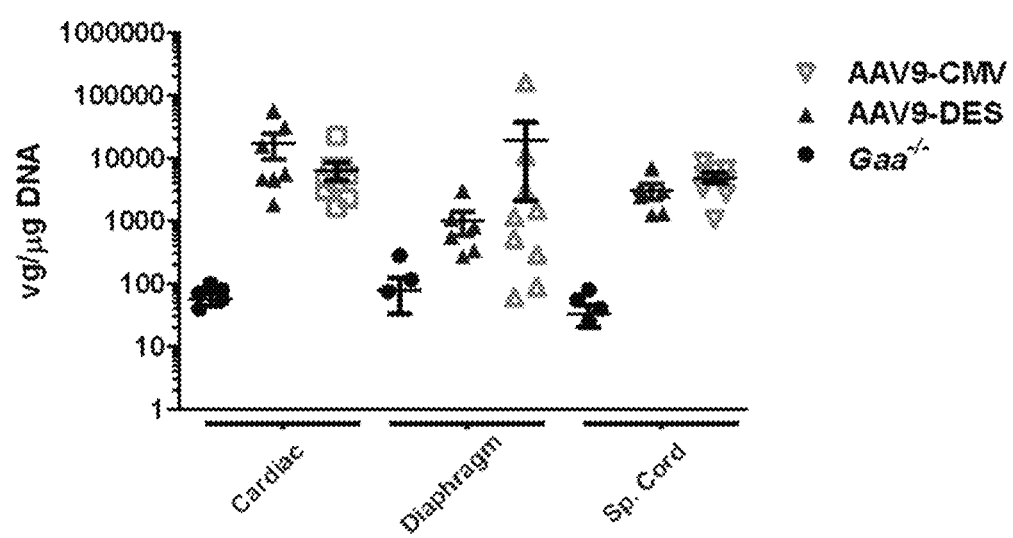
Figure 34I:
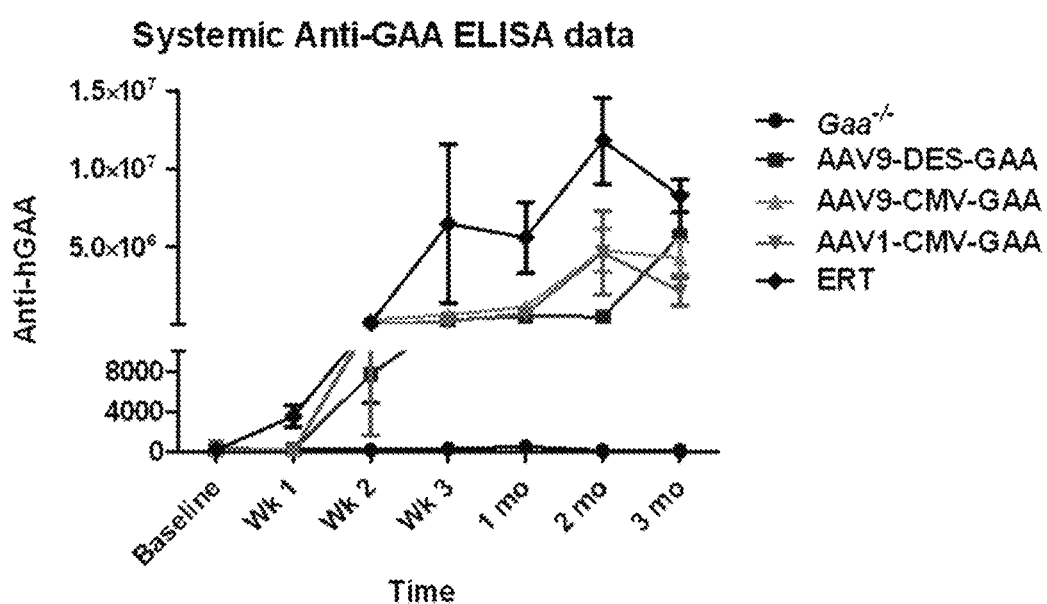

In another experiment, three-month-old $Gaa^{-/-}$ mice received a single intravenous injection of $1\times10^{11}$ vg ($\sim 5\times10^6$ vg/kg) AAV2/9-(CMV or DES)-GAA. Cardiac and diaphragm functional measurements were conducted at 3 months post-treatment (6 months of age) in parallel to age-matched untreated $Gaa^{-/-}$ and wild-type 129SVe (WT) mice. DES-GAA treated animals showed a marked improvement in cardiac function with levels similar to WT (FIG. 34A) and reduction of left ventricular mass. Contractile function of diaphragm strips from untreated $Gaa^{-/-}$, AAV2/9-CMV, AAV2/9-DES, and WT was measured, and the results show improved function in AAV2/9/-CMV-GAA and AAV2/9-DES-GAA treated groups (FIG. 34F). The results also show that the DES-driven GAA is more efficacious in systemically treated animals.

Example 10

Production of rAAV Vectors Using an HSV-based System

One major hurdle for the use of rAAV in gene therapy applications is the lack of capability to generate high yield of vector at high titer and high purity. Manufacturing amounts in the range of $1\times10^{14}$ to $1\times10^{15}$ vector genomes using the transfection-based production system remains cumbersome, time-consuming and costly.

This Example pertains to the production of large amount of rAAV vectors (e.g., rAAV2/9-hGAA) using a production platform based on the Herpes Simplex virus type I System (HSV). The current system utilizes two recombinant HSV: one carrying the AAV rep and cap, or "helper" and the other one carrying the recombinant AAV genome containing the transgene expression cassette. AAV production is initiated upon co-infection of cells with the two recombinant HSV and harvest typically occurs within 52 hours. Producer cells (HEK293 or BHK21) can be grown on adherent support (flask or cell factory) or in suspension in a Wave Bioreactor type technology.

An additional challenge for the use of rAAV in gene therapy applications is the lack of efficient, high recovery streamline purification method for AAV vectors (e.g., AAV2/9). This Example also provides a streamline protocol to purify rAAV9 particles from crude cell extracts that can be applied to large-scale production protocols.

Establishment of a scalable and flexible platform based on the HSV system is required for generating sufficient amounts of highly pure and concentrated rAAV vectors (e.g., rAAV2/9-GAA). rAAV9 vector stocks prepared using the HSV system or the standard co-transfection protocol in 293 cells are compared based on the following parameters: i) the biochemical purity of the preparation (i.e., absence of contaminant proteins) ii) the ratio of infectious-to-physical particles; iii) the ratio of VP1:VP2:VP3 capsid proteins; and iv) the ratio full-versus-empty particles.

Implementation of scalable production method based on the HSV system and a streamline purification protocol for AAV9 enables the preparation of large amounts of highly pure and potent rAAV vectors (e.g., rAAV2/9-GAA) in a time and cost effective manner. rAAV vectors (e.g., rAAV2/9-GAA) manufactured using the HSV system are characterized based on purity and biological potency levels comparable to, or exceeding, the vectors prepared in HEK293 cells using transfection method.

Figure 35:
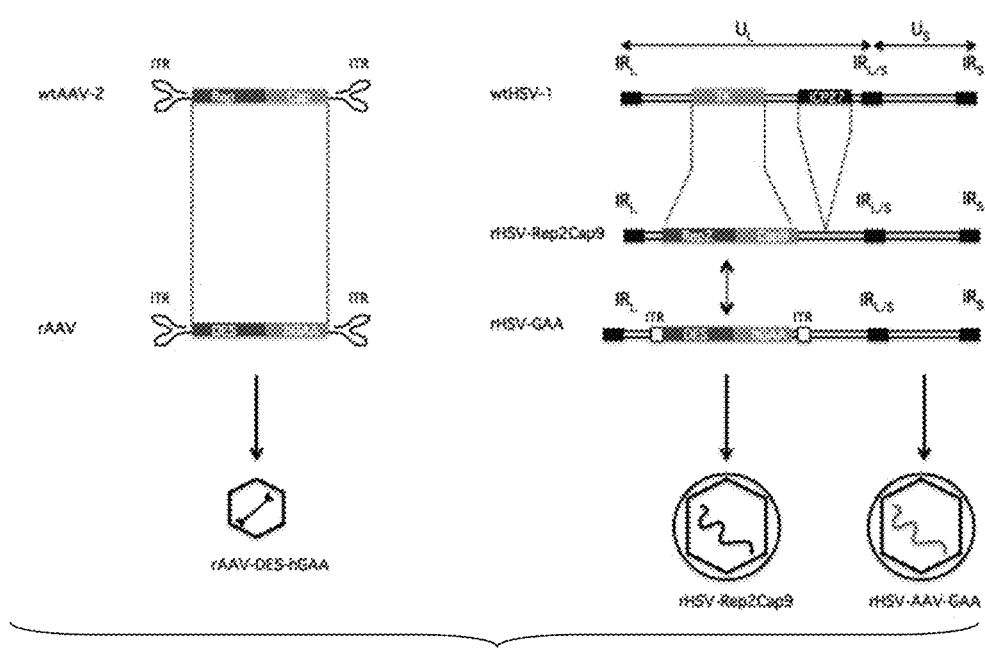
FIG. 35 is a schematic representation of AAV and HSV viruses. Wild-type and recombinant genomes are shown with major genetic elements.
Figure 36:
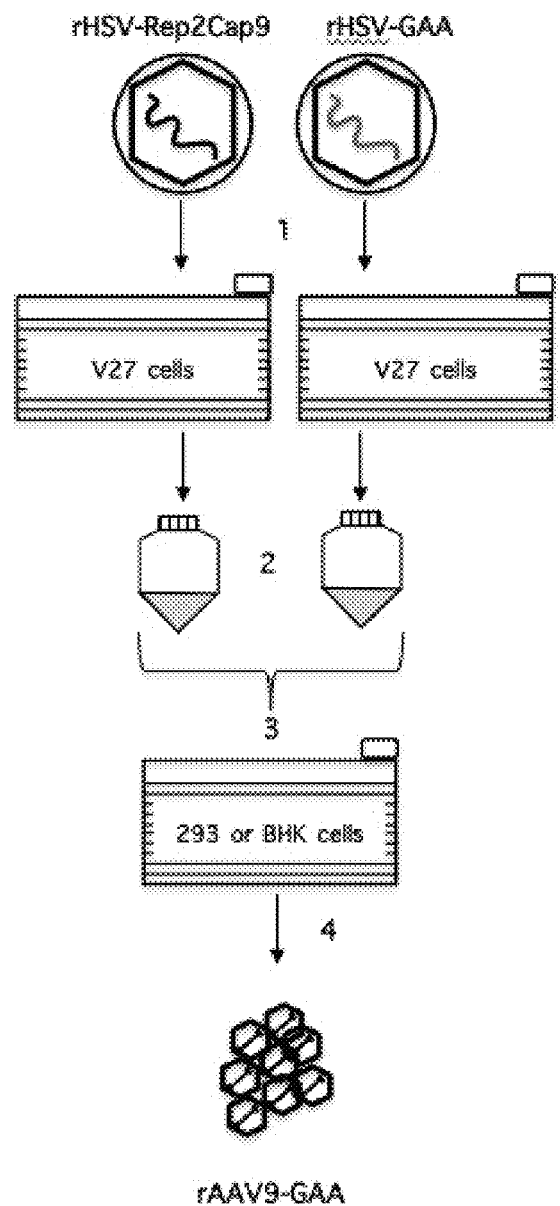
FIG. 36 illustrates the production of AAV by HSV coinfection method using adherent cells. 1 and 2) generation of rHSV stocks; 3) coinfection with rHSV; 4) harvest and recovery of rAAV.
Figures 37A, 37B:
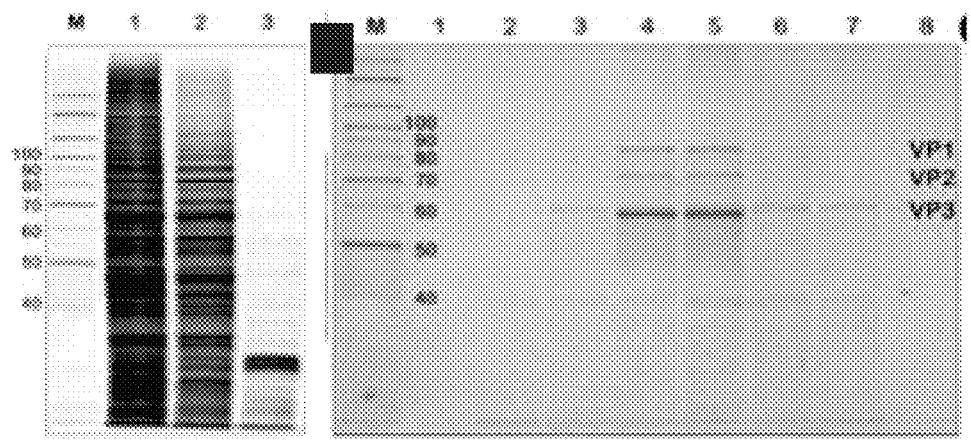
FIG. 37A and FIG. 37B show streamlined purification of rAAV2/9 by pI precipitation and column chromatography.

FIG. 35 is a schematic representation of vector constructs of the HSV-based production system. FIG. 36 shows streamlined purification of rAAV vectors by pI precipitation and column chromatography. FIG. 37 shows AAV production by HSV coinfection method using adherent cells.

Preparation of HSV-AAV-hGAA and HSV-AAV/rep2cap9 Helper

Two recombinant HSV-AAV-hGAAs (HSV-hGAA and HSV-coGAA) are engineered by homologous recombination into the thymidine kinase (tk) locus of the replication-defective rHSV-1 vector, ICP27-deleted (infected cell protein 27). AAV-DES-hGAA contains the human GAA ORF downstream of the desmin promoter and bracketed by AAV serotype 2 terminal repeats (ITRs). The AAV-DES-cohGAA contains a codon-optimized version of the human GAA ORF for higher expression in eukaryotic cells (GeneArt, Invitrogen).

The HSV-AAV9 helper is generated by inserting the PCR generated sequence of AAV2 rep, and AAV9 cap from plasmid pRep2Cap9 (obtained from Dr. Jim Wilson, UPenn Recombinant viruses is screened and isolated by plaque assay and further amplified by clonal propagation on V27 cells, Vero-derived cells which supply ICP27.

Methods for Generating rHSV.

HSV viruses are recovered from cell supernatant and are further filtered and concentrated prior to titering. Small and medium scale rAAV productions are conducted in either HEK293 grown in flasks (T225 or cell factory) or in suspension-adapted BHK cells in spinner cultures (up to 1 L or $1\times10^9$ cells). Cells are coinfected with rHSV-hGAA (or rHSV-cohGAA) and rHSV-rep2/cap9 WVBs at appropriate MOIs. Cells are harvested at ~52 hours post-infection. AAV9 are purified using our standard purification method using freeze-thaws and iodixanol gradient, followed by concentration using Apollo centrifugal device. Stocks are analyzed for vector genome titer by Q-PCR and for purity by silver stained SDS-PAGE.

An alternative purification method for mid-scale production ($>1\times10^9$ cells) involves preparing cell crude lysates by microfluidization and purifying AAV9 particles by pI precipitation and column chromatography. During Process & Development, methods described above as well as small batches of AAV9 prepared in HEK293 by conventional $CaPO_4$ transfection are evaluated with respect to yield/cell, ratio empties/full, purity and ratio particle-to-infectious units.

Scale-up of the suspension-based format is necessary for large scale rAAV9 production. Briefly, sBHK cells are grown in either spinner cultures (1 L and up) or disposable bioreactor type Wave 10 L and up (Wave™, GE Healthcare) and coinfected with rHSV-hGAA and rHSV-rep2/cap9 WVBs. The advantages of the suspension BHK system is an increased cell density (up to $2\times10^9$ cell/L) and lower HSV input (or MOI), which typically results in a net increase of rAAV yield. After approximately 52 hrs, cells and supernatant are lysed in situ and clarified by depth filtration and absolute filtration. The clarified lysate is then be concentrated and formulated to an appropriate buffer by Tangential Flow Filtration (TFF) prior to further purification.

Progress in the purification of AAV9 vectors.

The inventors have developed a novel AAV (e.g., AAV9) purification protocol based on isoelectric point (pI) precipitation. The purification protocol is applicable to larger scale crude lysates ($>1\times10^9$ cells). Using empirically established conditions, the majority of proteins in crude cell lysates generated from transfected HEK293 cells are selectively precipitated, while more than 95% rAAV9 in solution are retained. A pre-purified rAAV9 is then subjected to a 5 mL SP Sepharose ion-exchange chromatography (HiTrap SP HP, GE Healthcare), and the fractions from the elution peak are spun through Apollo 150 kD cut-off filter. High molecular weight particles of AAV9 of are retained and concentrated, while smaller size proteins present after SP-chromatography are removed. This streamlined protocol results in highly purified vector, and almost 80% of the virus originally present in the crude lysate is retained.

Quality Control Assays.

Identity, purity, vector genome titers and infectivity titers of rAAV9 preparations are assessed. Biochemical identity and purity are determined using polyacrylamide gel electrophoresis technique. AAV capsid proteins VP1, 2 and 3 are visualized by silver staining or Coomassie Blue in the presence of appropriate controls. Level of impurities is quantified by gel imaging utilizing Quantity-One software (Bio-Rad). Vector genome titers are determined using an established Real-Time Quantitative PCR (Q-PCR) protocol that utilizes primers for the SV40 polyadenylation signal sequence specific to the vector genome. Infectious Titer Assay is performed by co-infecting C12 cells (HeLa cells expressing AAV2 Rep and Cap) with rAAV9 preparations and WT Adenovirus. Infected cells are subsequently trapped on nitrocellulose filters and probed for transgene (GAA cDNA) and only cells that have been productively infected with rAAV produce a visible spot on film. The ratio between full and empty capsids is determined by electron microscopy.

OTHER EMBODIMENTS

Any improvement may be made in part or all of the compositions and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

We claim:

1. A method of treating Pompe disease in a human patient having Pompe disease, said method comprising administering to said patient a therapeutically effective amount of a pseudotyped recombinant adeno-associated virus (rAAV) rAAV2/9, wherein said pseudotyped rAAV comprises a nucleic acid encoding a human alpha-glucosidase (GAA) polypeptide operably linked to a promoter,
   wherein said promoter mediates expression of said GAA polypeptide in a muscle cell, wherein said promoter is selected from a desmin promoter and a creatine kinase promoter.

2. The method of claim 1, said method comprising administering said pseudotyped rAAV to said patient intravenously.

3. The method of claim 1, said method comprising administering said pseudotyped rAAV to said patient intramuscularly.

4. The method of claim 3, said method comprising administering said pseudotyped rAAV directly to an intrathoracic muscle in said patient.

5. The method of claim 4, wherein said intrathoracic muscle is myocardial tissue.

6. The method of claim 1, wherein said pseudotyped rAAV is administered directly to the diaphragm of said patient.

7. The method of claim 1, wherein said promoter is a desmin promoter.

8. The method of claim 1, wherein said promoter is a muscle creatine kinase promoter.

* * * * *